United States Patent
Feng et al.

(10) Patent No.: US 12,012,390 B2
(45) Date of Patent: *Jun. 18, 2024

(54) FLAVONE COMPOUNDS FOR THE TREATMENT AND PROPHYLAXIS OF HEPATITIS B VIRUS DISEASE

(71) Applicant: Hoffmann-La Roche Inc., Little Falls, NJ (US)

(72) Inventors: Song Feng, Shanghai (CN); Chungen Liang, Shanghai (CN); Yongfu Liu, Shanghai (CN); Hong Shen, Shanghai (CN); Xuefei Tan, Shanghai (CN); Jun Wu, Basel (CN); Dongdong Chen, Shanghai (CN); Chao Li, Shanghai (CN); Li Wang, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 284 days.

This patent is subject to a terminal disclaimer.

(21) Appl. No.: 17/275,502

(22) PCT Filed: Sep. 11, 2019

(86) PCT No.: PCT/EP2019/074173
§ 371 (c)(1),
(2) Date: Mar. 11, 2021

(87) PCT Pub. No.: WO2020/053249
PCT Pub. Date: Mar. 19, 2020

(65) Prior Publication Data
US 2022/0363657 A1    Nov. 17, 2022

(30) Foreign Application Priority Data

Sep. 14, 2018    (WO) ................. PCT/EP2018/074851

(51) Int. Cl.
C07D 311/30    (2006.01)
A61P 31/20    (2006.01)
C07D 335/06    (2006.01)
C07D 405/04    (2006.01)

(52) U.S. Cl.
CPC ............ C07D 311/30 (2013.01); A61P 31/20 (2018.01); C07D 335/06 (2013.01); C07D 405/04 (2013.01)

(58) Field of Classification Search
CPC .................. C07D 311/30; C07D 405/04
See application file for complete search history.

(56) References Cited

U.S. PATENT DOCUMENTS

| | | | |
|---|---|---|---|
| 8,710,097 B2 * | 4/2014 | Chan | A61P 43/00 549/403 |
| 9,611,256 B2 | 4/2017 | Chow et al. | |
| 10,045,961 B2 | 8/2018 | Chang et al. | |
| 10,208,025 B2 * | 2/2019 | Chow | A61K 47/55 |
| 11,708,344 B2 * | 7/2023 | Chen | C07D 311/32 549/355 |

FOREIGN PATENT DOCUMENTS

| | | |
|---|---|---|
| CN | 101454305 A | 6/2009 |
| CN | 101708182 A | 5/2010 |
| CN | 102617536 A | 8/2012 |
| CN | 103275051 A | 9/2013 |
| CN | 104169267 A | 11/2014 |
| CN | 105640933 A | 6/2016 |
| CN | 105744837 A | 7/2016 |
| TW | I332001 | 10/2010 |
| TW | 201542202 A | 11/2011 |
| WO | 01/03681 A2 | 1/2001 |
| WO | 2007/135592 A1 | 11/2007 |
| WO | 2013/127361 A1 | 9/2013 |
| WO | 2015/061294 A2 | 4/2015 |
| WO | 2016/035808 A1 | 3/2016 |
| WO | 2017/202798 A1 | 11/2016 |

OTHER PUBLICATIONS

Daskiewicz, J et al., "Effects of Flavonoids on Cell Proliferation and Caspase Activation in a Human Colonic Cell Line HT29: An SAR Study" J Med Chem 48(8):2790-2804 (Mar. 30, 2005).
Fukai, T. et al., "Revised Structure of Albanins D and E, Geranylated Flavones from Morus Alba" Heterocycles 32(3):499-510 ( 1991).
International Preliminary Report on Patentability for PCT/EP2018/074851 dated Mar. 9, 2021.
International Preliminary Report on Patentability for PCT/EP2019/074173 dated Mar. 9, 2021.
International Search Report for PCT/EP2018/074851 dated Apr. 25, 2019.
International Search Report for PCT/EP2019/074173 dated Oct. 24, 2019.

(Continued)

*Primary Examiner* — Golam M Shameem

(57) ABSTRACT

The present invention provides flavone derivatives having the general formula (I) which are useful for the treatment of Hepatitis B Virus infection (HBV). The compounds act as cccDNA (covalently closed circular DMA) inhibitors.

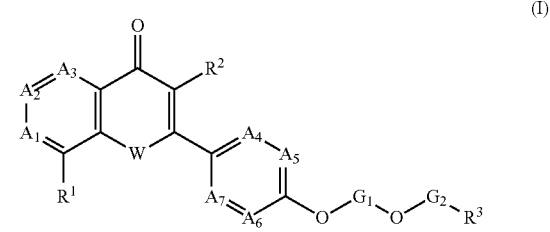

(I)

19 Claims, 1 Drawing Sheet
Specification includes a Sequence Listing.

(56) References Cited

OTHER PUBLICATIONS

Shih, T. L. et al., "Copper-mediated trimethylsilyl azide in amination of bromoflavonoids to synthesize unique aminoflavonoids" Tetrahedron 70(23):3657-3664 (Jun. 10, 2014).
Xiao, J.B. et al., "Anti-Hepatitis B Virus Activity of Flavonoids from marchantia Convoluta" IJPT 1:128 (Aug. 8, 2006).

* cited by examiner

Novel flavone compounds for the treatment and prophylaxis of Hepatitis B Virus disease
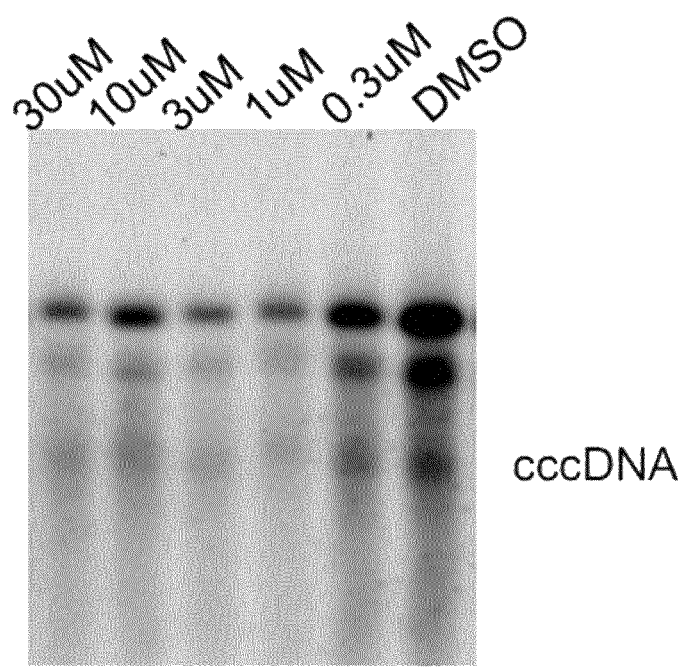

FLAVONE COMPOUNDS FOR THE TREATMENT AND PROPHYLAXIS OF HEPATITIS B VIRUS DISEASE

The present invention relates to organic compounds useful for therapy and/or prophylaxis of HBV infection in a mammal, and in particular to cccDNA (covalently closed circular DNA) inhibitors useful for treating HBV infection.

FIELD OF THE INVENTION

The present invention relates to novel flavone derivatives having pharmaceutical activity, their manufacture, pharmaceutical compositions containing them and their potential use as medicaments.

The present invention relates to compounds of formula (I)

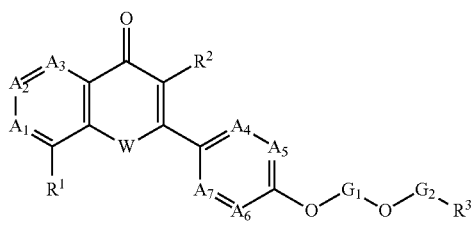

wherein $R^1$ to $R^3$, $G_1$, $G_2$, $A_1$ to $A_7$ and W are as described below, or pharmaceutically acceptable salt, or enantiomer, or diastereomer thereof.

Hepatitis B virus (HBV) infection is one of the most prevalent viral infections and is a leading cause of chronic hepatitis. It is estimated that worldwide, around 2 billion people have evidence of past or present infection with HBV. Over 250 million individuals are currently chronically infected with HBV and are therefore at high risk to develop liver fibrosis, cirrhosis and hepatocellular carcinoma (HCC). There are data to indicate ~800,000 deaths per year are directly linked to HBV infection (Lozano, R. et al., Lancet (2012), 380 (9859), 2095-2128; Goldstein, S. T. et al., Int J Epidemiol (2005), 34 (6), 1329-1339).

Many countries in the world administer hepatitis B vaccine starting at birth or in early childhood, which has greatly reduced the incidence and prevalence of hepatitis B in most endemic regions over the past few decades. However the vaccine has no impact on people who were infected before the widely use of the vaccine in developing end-stage liver disease or HCC (Chen, D. S., J Hepatol (2009), 50 (4), 805-816). Vaccination at birth of infants born to HBV positive mothers is usually not sufficient for protecting vertical transmission and combination with hepatitis B immune globulin is needed (Li, X. M. et al., World J Gastroenterol (2003), 9 (7), 1501-1503).

Currently FDA-approved treatments for chronic hepatitis B include two type 1 interferons (IFN) which are IFNalfa-2b and pegylated IFN alfa-2a and six nucleos(t)ide analogues (NAs) which are lamivudine (3TC), tenofovir disoproxil fumarate (TDF), adefovir (ADV), telbivudine (LdT), entecavir (ETV), and vemlidy (tenofovir alafenamide (TAF)). IFN treatment is finite, but it is known to have severe side effects, and only a small percentage of patients showed a sustained virological response, measured as loss of hepatitis B surface antigen (HBsAg). NAs are inhibitors of the HBV reverse transcriptase, profoundly reduce the viral load in vast majority of treated patients, and lead to improvement of liver function and reduced incidence of liver failure and hepatocellular carcinoma. However, the treatment of NAs is infinite (Ahmed, M. et al., Drug Discov Today (2015), 20 (5), 548-561; Zoulim, F. and Locarnini, S., Gastroenterology (2009), 137 (5), 1593-1608 e1591-1592).

HBV chronic infection is caused by persistence of covalently closed circular (ccc)DNA, which exists as an episomal form in hepatocyte nuclei. cccDNA serves as the template for viral RNA transcription and subsequent viral DNA generation. Only a few copies of cccDNA per liver cell can establish or re-initiate viral replication. Therefore, a complete cure of chronic hepatitis B will require elimination of cccDNA or permanently silencing of cccDNA. However, cccDNA is intrinsically very stable and currently available therapeutics could not eliminate cccDNA or permanently silence cccDNA (Nassal, M., Gut (2015), 64 (12), 1972-1984; Gish, R. G. et al., Antiviral Res (2015), 121, 47-58; Levrero, M. et al., J Hepatol (2009), 51 (3), 581-592.). The current SoC could not eliminate the cccDNA which are already present in the infected cells. There is an urgent need to discover and develop new anti-HBV reagents to eliminate or permanently silence cccDNA, the source of chronicity (Ahmed, M. et al., Drug Discov Today (2015), 20 (5), 548-561; Nassal, M., Gut (2015), 64 (12), 1972-1984).

SUMMARY OF THE INVENTION

Objects of the present invention are novel compounds of formula (I), their manufacture, medicaments based on a compound in accordance with the invention and their production as well as the use of compounds of formula (I) as cccDNA inhibitors and for the treatment or prophylaxis of HBV infection. The compounds of formula (I) show superior anti-HBV activity. In addition, the compounds of formula (I) also show good PK profiles.

The present invention relates to a compound of formula (I)

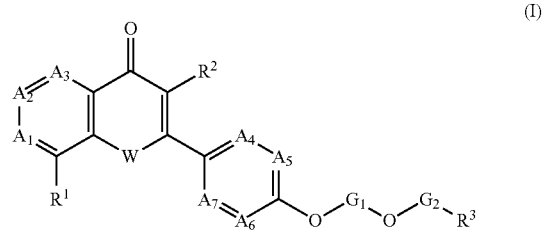

wherein,
W is O or S;
$A_1$ is CH or $CR^4$;
$A_2$ is CH or $CR^4$;
$A_3$ is CH or $CR^4$;
$A_4$ is N, CH or $CR^4$;
$A_5$ is N, CH or $CR^4$;
$A_6$ is CH;
$A_7$ is N or CH;
$R^1$ is halogen, $C_{1-6}$alkyl or $C_{3-7}$cycloalkyl;
$R^2$ is H, OH, halogen or $C_{1-6}$alkoxy;
$R^3$ is carboxy or $C_{1-6}$alkoxycarbonyl;
$R^4$ is halogen, OH, CN, $C_{1-6}$alkyl, $C_{3-7}$cycloalkyl or $C_{1-6}$alkoxy;

G$_1$ is C$_{1-6}$alkyl, hydroxyC$_{1-6}$alkyl or C$_{3-7}$cycloalkyl C$_{1-6}$alkyl;

G$_2$ is C$_{1-6}$alkyl, C$_{3-7}$cycloalkyl or phenyl;

or pharmaceutically acceptable salt, or enantiomer, or diastereomer thereof.

DETAILED DESCRIPTION OF THE INVENTION

Definitions

As used herein, the term "C$_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "C$_{1-6}$alkyl" groups are methyl, ethyl, isopropyl and tert-butyl. More particularly, "C$_{1-6}$alkyl" group is methyl.

The term "C$_{3-7}$cycloalkyl" denotes to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "C$_{3-7}$cycloalkyl" group is cyclopropyl, cyclobutyl or cyclopentyl.

The term "C$_{1-6}$alkoxy" alone or in combination signifies a group C$_{1-6}$alkyl-O—, wherein the "C$_{1-6}$alkyl" is as defined above; for example methoxy, ethoxy, propoxy, iso-propoxy, n-butoxy, iso-butoxy, 2-butoxy, tert-butoxy, pentoxy, hexyloxy and the like. Particular "C$_{1-6}$alkoxy" groups are methoxy, ethoxy and propoxy. More particularly, "C$_{1-6}$alkoxy" group is methoxy or ethoxy.

The term "halogen" means fluorine, chlorine, bromine or iodine.

The term "carbonyl" alone or in combination refers to the group —C(O)—.

The term "enantiomer" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435. Particular are the sodium salts of the compounds of formula (I).

Compounds of the general formula (I) which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

cccDNA Inhibitors

The present invention provides (i) a compound having the general formula (I):

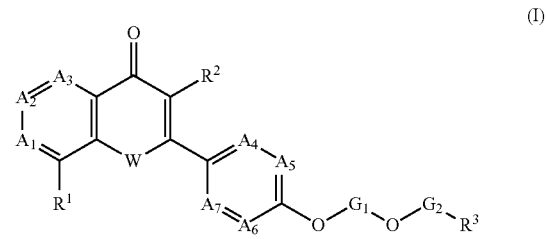

(I)

wherein,

W is O or S;

A$_1$ is CH or CR$^4$;

A$_2$ is CH or CR$^4$;

A$_3$ is CH or CR$^4$;

A$_4$ is N, CH or CR$^4$;

A$_5$ is N, CH or CR$^4$;

A$_6$ is CH;

A$_7$ is N or CH;

R$^1$ is halogen, C$_{1-6}$alkyl or C$_{3-7}$cycloalkyl;

R$^2$ is H, OH, halogen, C$_{1-6}$alkoxy, haloC$_{1-6}$alkoxy or phenylC$_{1-6}$alkoxy;

R$^3$ is carboxy or C$_{1-6}$alkoxycarbonyl;

R$^4$ is halogen, OH, CN, C$_{1-6}$alkyl, C$_{3-7}$cycloalkyl, C$_{1-6}$alkoxy, oxopyrrolidinyl, morpholinyl or haloC$_{1-6}$alkyl;

G$_1$ is C$_{1-6}$alkyl, hydroxyC$_{1-6}$alkyl or C$_{3-7}$cycloalkyl C$_{1-6}$alkyl;

G$_2$ is C$_{1-6}$alkyl, C$_{3-7}$cycloalkyl or phenyl;

or pharmaceutically acceptable salt, or enantiomer, or diastereomer thereof.

A another embodiment of the present invention is a compound of formula (I), wherein W is O or S;

A$_1$ is CH or CR$^4$;

A$_2$ is CH or CR$^4$;

A$_3$ is CH or CR$^4$;

A$_4$ is N, CH or CR$^4$;

A$_5$ is N, CH or CR$^4$;

A$_6$ is CH;

A$_7$ is N or CH;

R$^1$ is halogen, C$_{1-6}$alkyl or C$_{3-7}$cycloalkyl;

R$^2$ is H, OH, halogen or C$_{1-6}$alkoxy;

R$^3$ is carboxy or C$_{1-6}$alkoxycarbonyl;

R$^4$ is halogen, OH, CN, C$_{1-6}$alkyl, C$_{3-7}$cycloalkyl or C$_{1-6}$alkoxy;

G$_1$ is C$_{1-6}$alkyl, hydroxyC$_{1-6}$alkyl or C$_{3-7}$cycloalkyl C$_{1-6}$alkyl;

G$_2$ is C$_{1-6}$alkyl, C$_{3-7}$cycloalkyl or phenyl;

or pharmaceutically acceptable salt, or enantiomer, or diastereomer thereof.

A further embodiment of the present invention is (ii) a compound of formula (I) according to (i), wherein
  W is O or S;
  $A_1$ is CH or $CR^4$;
  $A_2$ is CH or $CR^4$;
  $A_3$ is CH or $CR^4$;
  $A_4$ is N, CH or $CR^4$;
  $A_5$ is N, CH or $CR^4$;
  $A_6$ is CH;
  $A_7$ is N or CH;
  $R^1$ is Cl, Br, methyl or cyclopropyl;
  $R^2$ is H, OH, Cl, Br, methoxy, trifluoromethoxy or benzyloxy;
  $R^3$ is carboxy, methoxycarbonyl or ethoxycarbonyl;
  $R^4$ is F, Cl, Br, OH, CN, methyl, isopropyl, cyclopropyl, methoxy, ethoxy, isopropoxy, oxopyrrolidinyl, morpholinyl or trifluoromethyl;
  $G_1$ is cyclobutylmethyl, ethyl, hydroxypropyl, methylethyl or propyl;
  $G_2$ is cyclobutyl, cyclohexyl, cyclopentyl, cyclopropyl, dimethylethyl, ethyl, methyl and phenyl;
  or pharmaceutically acceptable salt, or enantiomer, or diastereomer thereof.

A further embodiment of the present invention is a compound of formula (I), wherein
  W is O or S;
  $A_1$ is CH or $CR^4$;
  $A_2$ is CH or $CR^4$;
  $A_3$ is CH or $CR^4$;
  $A_4$ is N, CH or $CR^4$;
  $A_5$ is N, CH or $CR^4$;
  $A_6$ is CH;
  $A_7$ is N or CH;
  $R^1$ is Cl, Br, methyl or cyclopropyl;
  $R^2$ is H, OH, Cl or methoxy;
  $R^3$ is carboxy, methoxycarbonyl or ethoxycarbonyl;
  $R^4$ is F, Cl, Br, OH, CN, methyl, isopropyl, cyclopropyl, methoxy, ethoxy or isopropoxy;
  $G_1$ is cyclobutylmethyl, ethyl, hydroxypropyl, methylethyl or propyl;
  $G_2$ is cyclobutyl, cyclohexyl, cyclopentyl, cyclopropyl, dimethylethyl, ethyl, methyl and phenyl;
  or pharmaceutically acceptable salt, or enantiomer, or diastereomer thereof.

A further embodiment of the present invention is (iii) a compound of formula (I) or pharmaceutically acceptable salt, or enantiomer, or diastereomer thereof, wherein $A_1$ is CH.

A further embodiment of the present invention is (iv) a compound of formula (I) or pharmaceutically acceptable salt, or enantiomer, or diastereomer thereof, wherein $A_4$ is CH or $CR^4$.

A further embodiment of the present invention is (v) a compound of formula (I) or pharmaceutically acceptable salt, or enantiomer, or diastereomer thereof, wherein $A_5$ is CH or $CR^4$.

A further embodiment of the present invention is (vi) a compound of formula (I), or pharmaceutically acceptable salt, or enantiomer, or diastereomer thereof, wherein $A_7$ is CH.

A further embodiment of the present invention is (vii) a compound of formula (I), or pharmaceutically acceptable salt, or enantiomer, or diastereomer thereof, wherein $R^1$ is halogen.

A further embodiment of the present invention is (viii) a compound of formula (I), or pharmaceutically acceptable salt, or enantiomer, or diastereomer thereof, wherein $R^2$ is H.

A further embodiment of the present invention is (ix) a compound of formula (I), or pharmaceutically acceptable salt, or enantiomer, or diastereomer thereof, wherein $R^3$ is carboxy.

A further embodiment of the present invention is (x) a compound of formula (I), or pharmaceutically acceptable salt, or enantiomer, or diastereomer thereof, wherein $R^4$ is halogen, $C_{1-6}$alkyl or $C_{1-6}$alkoxy.

A further embodiment of the present invention is (xi) a compound of formula (I), or pharmaceutically acceptable salt, or enantiomer, or diastereomer thereof, wherein $G_1$ is $C_{1-6}$alkyl.

A further embodiment of the present invention is (xii) a compound of formula (I), or pharmaceutically acceptable salt, or enantiomer, or diastereomer thereof, wherein $G_2$ is $C_{1-6}$alkyl or $C_{3-7}$cycloalkyl.

Another further embodiment of the present invention is (xiii) a compound of formula (I), wherein
  W is O or S;
  $A_1$ is CH;
  $A_2$ is CH or $CR^4$;
  $A_3$ is CH or $CR^4$;
  $A_4$ is CH or $CR^4$;
  $A_5$ is CH or $CR^4$;
  $A_6$ is CH;
  $A_7$ is CH;
  $R^1$ is halogen;
  $R^2$ is H;
  $R^3$ is carboxy;
  $R^4$ is halogen, $C_{1-6}$alkyl or $C_{1-6}$alkoxy;
  $G_1$ is $C_{1-6}$alkyl;
  $G_2$ is $C_{1-6}$alkyl or $C_{3-7}$cycloalkyl;
  or pharmaceutically acceptable salt, or enantiomer, or diastereomer thereof.

Another further embodiment of the present invention is (xiv) a compound of formula (I), wherein
  W is O or S;
  $A_1$ is CH;
  $A_2$ is CH or $CR^4$;
  $A_3$ is CH or $CR^4$;
  $A_4$ is CH or $CR^4$;
  $A_5$ is CH or $CR^4$;
  $A_6$ is CH;
  $A_7$ is CH;
  $R^1$ is Cl, Br;
  $R^2$ is H;
  $R^3$ is carboxy;
  $R^4$ is F, Cl, Br, methyl, ethoxy or methoxy;
  $G_1$ is ethyl or methylethyl;
  $G_2$ is cyclobutyl or methyl;
  or pharmaceutically acceptable salt, or enantiomer, or diastereomer thereof.

In another embodiment (xv) of the present invention, particular compounds of the present invention are selected from:
3-[2-[4-(8-chloro-4-oxo-chromen-2-yl)phenoxy]ethoxy]cyclobutanecarboxylic acid;
Ethyl 3-[2-[4-(8-chloro-4-oxo-chromen-2-yl)phenoxy]ethoxy]cyclobutanecarboxylate;
3-[2-[4-(8-chloro-4-oxo-chromen-2-yl)phenoxy]ethoxy]benzoic acid;
Ethyl 2-[2-[4-(8-chloro-4-oxo-chromen-2-yl)phenoxy]ethoxy]cyclopropanecarboxylate;
cis-2-[2-[4-(8-chloro-4-oxo-chromen-2-yl)phenoxy]ethoxy]cyclopropanecarboxylic acid;
trans-2-[2-[4-(8-chloro-4-oxo-chromen-2-yl)phenoxy]ethoxy]cyclopropanecarboxylic acid;

3-[2-[4-(8-chloro-4-oxo-chromen-2-yl)phenoxy]ethoxy]cyclopentanecarboxylic acid;
cis-4-[2-[4-(8-chloro-4-oxo-chromen-2-yl)phenoxy]ethoxy]cyclohexanecarboxylic acid;
trans-4-[2-[4-(8-chloro-4-oxo-chromen-2-yl)phenoxy]ethoxy]cyclohexanecarboxylic acid;
2-[3-[[4-(8-chloro-4-oxo-chromen-2-yl)phenoxy]methyl]cyclobutoxy]acetic acid;
2-[2-[4-(8-chloro-4-oxo-chromen-2-yl)phenoxy]ethoxy]acetic acid;
3-[2-[4-(8-chloro-4-oxo-chromen-2-yl)phenoxy]ethoxy]propanoic acid;
3-[2-[4-(8-chloro-4-oxo-chromen-2-yl)phenoxy]ethoxy]-2,2-dimethyl-propanoic acid;
3-[2-[4-(8-chloro-4-oxo-chromen-2-yl)phenoxy]-1-methyl-ethoxy]cyclobutanecarboxylic acid;
3-[3-[4-(8-chloro-4-oxo-chromen-2-yl)phenoxy]propoxy]cyclobutanecarboxylic acid;
3-[3-[4-(8-chloro-4-oxo-chromen-2-yl)phenoxy]-2-hydroxy-propoxy]benzoic acid;
3-[2-[4-(8-chloro-7-fluoro-4-oxo-chromen-2-yl)phenoxy]ethoxy]cyclobutanecarboxylic acid;
3-[2-[4-(8-chloro-7-methoxy-4-oxo-chromen-2-yl)phenoxy]ethoxy]cyclobutanecarboxylic acid;
3-[2-[4-(8-chloro-6-fluoro-4-oxo-chromen-2-yl)phenoxy]ethoxy]cyclobutanecarboxylic acid;
3-[2-[4-(7,8-dichloro-4-oxo-chromen-2-yl)phenoxy]ethoxy]cyclobutanecarboxylic acid;
3-[2-[4-(8-chloro-6-cyano-4-oxo-chromen-2-yl)phenoxy]ethoxy]cyclobutanecarboxylic acid;
3-[2-[4-(8-chloro-7-cyano-4-oxo-chromen-2-yl)phenoxy]ethoxy]cyclobutanecarboxylic acid;
cis-3-[2-[4-(8-chloro-5-hydroxy-4-oxo-chromen-2-yl)phenoxy]ethoxy]cyclobutanecarboxylic acid;
cis-3-[2-[4-(8-chloro-5-methoxy-4-oxo-chromen-2-yl)phenoxy]ethoxy]cyclobutanecarboxylic acid;
cis-3-[2-[4-(8-chloro-5-isopropoxy-4-oxo-chromen-2-yl)phenoxy]ethoxy]cyclobutanecarboxylic acid;
cis-3-[2-[4-(5-bromo-8-chloro-4-oxo-chromen-2-yl)phenoxy]ethoxy]cyclobutanecarboxylic acid;
cis-3-[2-[4-(5,8-dichloro-4-oxo-chromen-2-yl)phenoxy]ethoxy]cyclobutanecarboxylic acid;
cis-3-[2-[4-(8-chloro-5-cyclopropyl-4-oxo-chromen-2-yl)phenoxy]ethoxy]cyclobutanecarboxylic acid;
cis-3-[2-[4-(8-chloro-5-methyl-4-oxo-chromen-2-yl)phenoxy]ethoxy]cyclobutanecarboxylic acid;
cis-3-[2-[4-(8-bromo-4-oxo-chromen-2-yl)phenoxy]ethoxy]cyclobutanecarboxylic acid;
cis-3-[2-[4-(8-cyclopropyl-4-oxo-chromen-2-yl)phenoxy]ethoxy]cyclobutanecarboxylic acid;
cis-3-[2-[4-(8-methyl-4-oxo-chromen-2-yl)phenoxy]ethoxy]cyclobutanecarboxylic acid;
2-[2-[4-(8-chloro-5-fluoro-4-oxo-chromen-2-yl)phenoxy]ethoxy]acetic acid;
cis-3-[2-[[5-(8-chloro-4-oxo-chromen-2-yl)-2-pyridyl]oxy]ethoxy]cyclobutanecarboxylic acid;
trans-3-[2-[[5-(8-chloro-4-oxo-chromen-2-yl)-2-pyridyl]oxy]ethoxy]cyclobutanecarboxylic acid;
cis-3-[2-[5-(8-chloro-4-oxo-chromen-2-yl)pyrazin-2-yl]oxyethoxy]cyclobutanecarboxylic acid;
cis-methyl 3-[2-[5-(8-chloro-4-oxo-chromen-2-yl)pyrazin-2-yl]oxyethoxy]cyclobutanecarboxylate;
cis-methyl 3-[2-[6-(8-chloro-4-oxo-chromen-2-yl)pyridazin-3-yl]oxyethoxy]cyclobutanecarboxylate;
cis-3-[2-[4-(8-chloro-4-oxo-chromen-2-yl)-2-fluoro-phenoxy]ethoxy]cyclobutanecarboxylic acid;
cis-3-[2-[2-chloro-4-(8-chloro-4-oxo-chromen-2-yl)phenoxy]ethoxy]cyclobutanecarboxylic acid;
cis-3-[2-[2-bromo-4-(8-chloro-4-oxo-chromen-2-yl)phenoxy]ethoxy]cyclobutanecarboxylic acid;
cis-3-[2-[4-(8-chloro-4-oxo-chromen-2-yl)-2-cyclopropyl-phenoxy]ethoxy]cyclobutanecarboxylic acid;
3-[2-[4-(8-chloro-4-oxo-chromen-2-yl)-2-cyano-phenoxy]ethoxy]cyclobutanecarboxylic acid;
3-[2-[4-(8-chloro-4-oxo-chromen-2-yl)-2-methyl-phenoxy]ethoxy]cyclobutanecarboxylic acid;
3-[2-[4-(8-chloro-4-oxo-chromen-2-yl)-2-isopropyl-phenoxy]ethoxy]cyclobutanecarboxylic acid;
3-[2-[4-(8-chloro-4-oxo-chromen-2-yl)-3-methoxy-phenoxy]ethoxy]cyclobutanecarboxylic acid;
3-[2-[4-(8-chloro-4-oxo-chromen-2-yl)-3-ethoxy-phenoxy]ethoxy]cyclobutanecarboxylic acid;
3-[2-[4-(3,8-dichloro-4-oxo-chromen-2-yl)phenoxy]ethoxy]cyclobutanecarboxylic acid;
cis-3-[2-[4-(8-chloro-3-hydroxy-4-oxo-chromen-2-yl)phenoxy]ethoxy]cyclobutanecarboxylic acid;
cis-3-[2-[4-(8-chloro-3-methoxy-4-oxo-chromen-2-yl)phenoxy]ethoxy]cyclobutanecarboxylic acid;
3-[2-[4-(8-chloro-4-oxo-thiochromen-2-yl)phenoxy]ethoxy]cyclobutanecarboxylic acid;
2-[2-[4-(8-chloro-4-oxo-thiochromen-2-yl)phenoxy]ethoxy]acetic acid; and
2-[2-[4-(8-chloro-3-hydroxy-4-oxo-chromen-2-yl)phenoxy]ethoxy]acetic acid;
  or pharmaceutically acceptable salt, or enantiomer, or diastereomer thereof.

In a further embodiment (xvi) of the present invention, more particular compounds of the present invention are selected from:
3-[2-[4-(8-chloro-4-oxo-chromen-2-yl)phenoxy]ethoxy]cyclobutanecarboxylic acid;
cis-3-[2-[4-(8-chloro-4-oxo-chromen-2-yl)phenoxy]ethoxy]cyclobutanecarboxylic acid;
trans-3-[2-[4-(8-chloro-4-oxo-chromen-2-yl)phenoxy]ethoxy]cyclobutanecarboxylic acid;
3-[2-[4-(8-chloro-4-oxo-chromen-2-yl)phenoxy]-1-methyl-ethoxy]cyclobutanecarboxylic acid;
3-[2-[4-(8-chloro-6-fluoro-4-oxo-chromen-2-yl)phenoxy]ethoxy]cyclobutanecarboxylic acid;
cis-3-[2-[4-(8-chloro-5-methoxy-4-oxo-chromen-2-yl)phenoxy]ethoxy]cyclobutanecarboxylic acid;
cis-3-[2-[4-(5,8-dichloro-4-oxo-chromen-2-yl)phenoxy]ethoxy]cyclobutanecarboxylic acid;
cis-3-[2-[4-(8-bromo-4-oxo-chromen-2-yl)phenoxy]ethoxy]cyclobutanecarboxylic acid;
cis-3-[2-[4-(8-chloro-4-oxo-chromen-2-yl)-2-fluoro-phenoxy]ethoxy]cyclobutanecarboxylic acid;
cis-3-[2-[2-chloro-4-(8-chloro-4-oxo-chromen-2-yl)phenoxy]ethoxy]cyclobutanecarboxylic acid;
cis-3-[2-[2-bromo-4-(8-chloro-4-oxo-chromen-2-yl)phenoxy]ethoxy]cyclobutanecarboxylic acid;
3-[2-[4-(8-chloro-4-oxo-chromen-2-yl)-2-methyl-phenoxy]ethoxy]cyclobutanecarboxylic acid;
3-[2-[4-(8-chloro-4-oxo-chromen-2-yl)-3-ethoxy-phenoxy]ethoxy]cyclobutanecarboxylic acid;
3-[2-[4-(8-chloro-4-oxo-thiochromen-2-yl)phenoxy]ethoxy]cyclobutanecarboxylic acid;
2-[2-[4-(8-chloro-4-oxo-thiochromen-2-yl)phenoxy]ethoxy]acetic acid;
3-[2-[4-(8-chloro-4-oxo-chromen-2-yl)-3-morpholino-phenoxy]ethoxy]cyclobutanecarboxylic acid;
2-[2-[4-(8-chloro-4-oxo-chromen-2-yl)phenoxy]ethoxy]acetamide;

Methyl 3-[2-[4-[8-chloro-6-fluoro-4-oxo-3-(trifluoromethoxy)chromen-2-yl]phenoxy]ethoxy]cyclobutanecarboxylate;
3-[2-[4-[8-chloro-6-fluoro-4-oxo-3-(trifluoromethoxy)chromen-2-yl]phenoxy]ethoxy]cyclobutanecarboxylic acid;
3-[2-[4-(3-bromo-8-chloro-4-oxo-chromen-2-yl)phenoxy]ethoxy]cyclobutanecarboxylic acid;
3-[2-[4-(3-benzyloxy-8-chloro-4-oxo-chromen-2-yl)phenoxy]ethoxy]cyclobutanecarboxylic acid;
3-[2-[4-[8-chloro-4-oxo-6-(trifluoromethyl)chromen-2-yl]phenoxy]ethoxy]cyclobutanecarboxylic acid;
3-[2-[4-(8-chloro-6-cyclopropyl-4-oxo-chromen-2-yl)phenoxy]ethoxy]cyclobutanecarboxylic acid;
3-[2-[4-[8-chloro-4-oxo-6-(2-oxopyrrolidin-1-yl)chromen-2-yl]phenoxy]ethoxy]cyclobutanecarboxylic acid;
3-[2-[4-[8-chloro-4-oxo-7-(trifluoromethyl)chromen-2-yl]phenoxy]ethoxy]cyclobutanecarboxylic acid;
3-[2-[4-(8-chloro-7-cyclopropyl-4-oxo-chromen-2-yl)phenoxy]ethoxy]cyclobutanecarboxylic acid;
ethyl 2-[2-[4-(7-bromo-8-chloro-4-oxo-chromen-2-yl)phenoxy]ethoxy]acetate;
3-[2-[4-[8-chloro-4-oxo-7-(trifluoromethyl)chromen-2-yl]-2-methyl-phenoxy]ethoxy]cyclobutanecarboxylic acid; and
Cis-3-[2-[2-chloro-4-[8-chloro-4-oxo-7-(trifluoromethyl)chromen-2-yl]phenoxy]ethoxy]cyclobutanecarboxylic acid;
or pharmaceutically acceptable salt, or enantiomer, or diastereomer thereof.

Similar flavone compounds, 6,4'-dimethoxyflavone (compound F-1), 4'-methoxyflavone (compound F-2) disclosed in patent WO2015061294 for treating HBV infection as STING agonist and 4-(7-methoxy-4-oxo-chromen-3-yl)benzoic acid (compound F-3) was disclosed in patent (CN102617536) for treating HBV infection, were chosen as reference compounds in present invention.

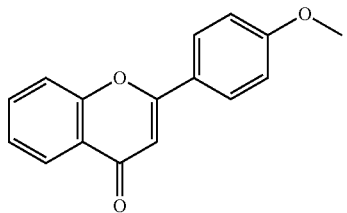

(compound F-1)

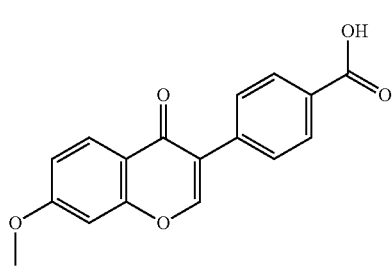

(compound F-2)

(compound F-3)

Synthesis

The compounds of the present invention can be prepared by any conventional means. Suitable processes for synthesizing these compounds as well as their starting materials are provided in the schemes below and in the subsequent examples. All substituents, in particular, $R^1$ to $R^3$, X, $G_1$, $G_2$, $A^1$ to $A^7$ are defined as below unless otherwise indicated. Furthermore, and unless explicitly otherwise stated, all reactions, reaction conditions, abbreviations and symbols have the meanings well known to a person of ordinary skill in the art.

Scheme 1

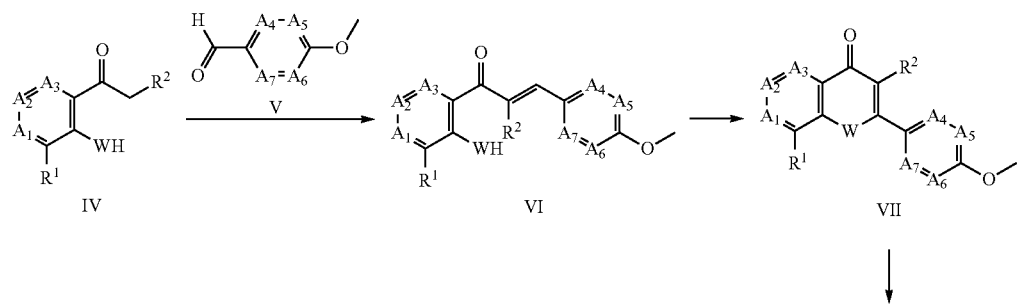

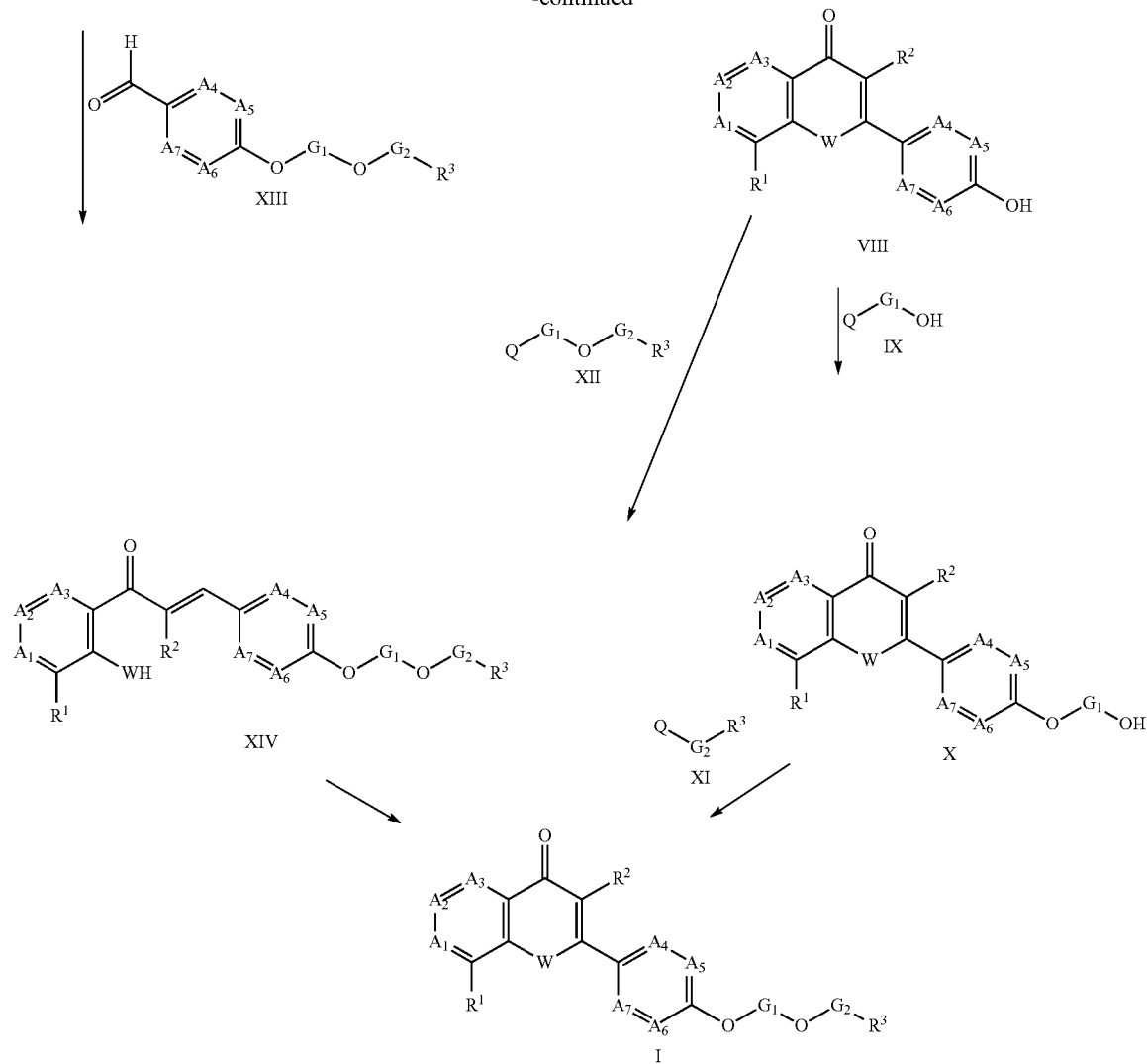

wherein Q is halogen, OTs, OTf or OMs; W is O or S.

Condensation of substituted ketone IV with substituted aldehyde V in the presence of a base, such as KOH, in a suitable solvent, such as ethanol, affords α,β-unsaturated carbonyl intermediate VI. Cyclization of intermediate VI in the presence of a suitable Lewis acid such as $I_2$, KI or NaI, in a suitable solvent, such as DMSO, affords flavone derivatives VII. Demethylation of intermediate VII with a suitable Lewis acid, such as $BBr_3$, in a suitable solvent, such as dichloromethane, affords compound of formula VIII. Substitution of compound of formula VIII with compound of formula IX in the presence of a suitable base, such as $K_2CO_3$, in a suitable solvent, such as DMF, affords compound of formula X. Substitution of compound of formula X with compound of formula XI in the presence of a suitable base, such as NaH, in a suitable solvent, such as DMSO, affords final compound of formula I. Alternatively, Substitution of compound of formula VIII with compound of formula XII in the presence of a suitable base such as $K_2CO_3$ in a suitable solvent such as DMF also affords compound of formula I.

The final compound of formula I can also be prepared by starting with condensation of substituted ketone IV with substituted aldehyde XIII in the presence of a base, such as KOH, in a suitable solvent, such as ethanol, affords α,β-unsaturated carbonyl compound of formula XIV. Cyclization of compound of formula XIV in the presence of a suitable Lewis acid, such as $I_2$, in a suitable solvent, such as DMSO, affords final compound of formula I.

Scheme 2

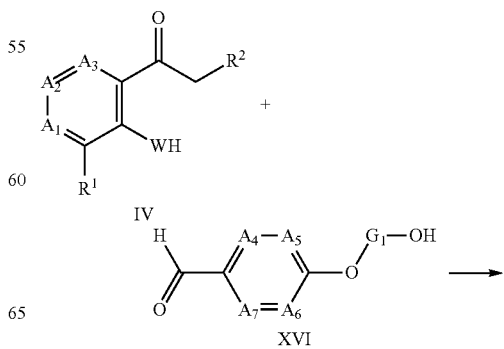

-continued

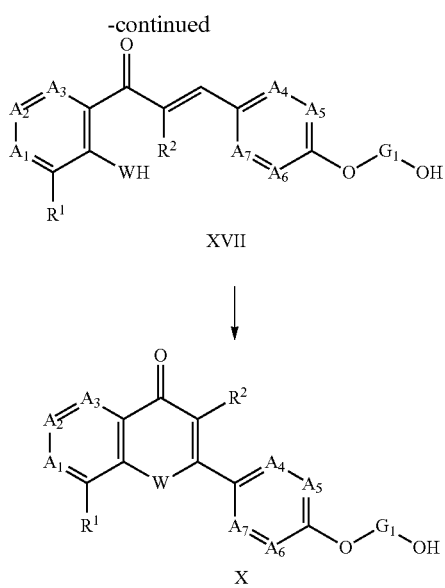

XVII

↓

X wherein W is O or S.

The intermediate X can also be prepared according to the Scheme 2. Condensation of substituted ketone IV with substituted aldehyde XVI in the presence of a base, such as KOH, in a suitable solvent, such as ethanol, affords α,β-unsaturated ketone intermediate XVII. Cyclization of intermediate XVII in the presence of a suitable Lewis acid, such as $I_2$, in a suitable solvent, such as DMSO, affords intermediates X.

This invention also relates to a process for the preparation of a compound of formula (I) comprising the following step:

(a) substitution of a compound of formula (X),

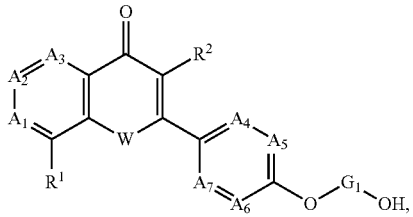
(X)

with a compound of formula (XI) in the presence of a base;

(b) substitution of a compound of formula (IX),

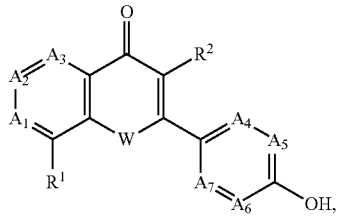
(IX)

with a compound of formula (XII) in the presence of a base;

(c) cyclization of compound of formula (XIV),

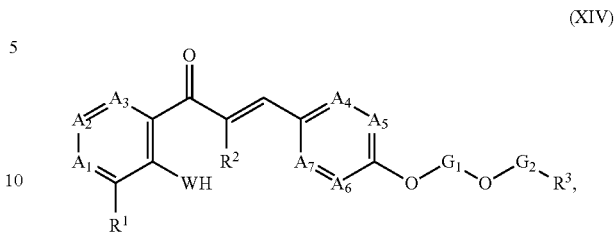
(XIV)

in the presence of a suitable Lewis acid;
wherein $R^1$, $R^2$, $R^3$, W, $A_1$ to $A_7$, $G_1$ and $G_2$ are defined as above;
the base in step (a) can be for example NaH;
the base in step (b) can be for example $K_2CO_3$;
the Lewis acid in step (c) can be for example $I_2$.

A compound of formula (I) when manufactured according to the above process is also an object of the invention.

Pharmaceutical Compositions and Administration

The invention also relates to a compound of formula (I) for use as therapeutically active substance. Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit cccDNA in HBV patients, consequently lead to the reduction of HBsAg and HBeAg (HBV e antigen) in serum. For example, such amount may be below the amount that is toxic to normal cells, or the mammal as a whole.

In one example, the pharmaceutically effective amount of the compound of the invention administered parenterally per dose will be in the range of about 0.1 to 100 mg/kg, alternatively about 0.1 to 50 mg/kg of patient body weight per day, with the typical initial range of compound used being 0.3 to 15 mg/kg/day. In another embodiment, oral unit dosage forms, such as tablets and capsules, preferably contain from about 25 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 25 to 500 mg of the compound of the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 5 to 400 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula (I), or pharmaceutically acceptable salt or enantiomer or diastereomer thereof.

In a further embodiment includes a pharmaceutical composition comprising a compound of formula (I), or pharmaceutically acceptable salt or enantiomer or diastereomer thereof, together with a pharmaceutically acceptable carrier or excipient.

Another embodiment includes a pharmaceutical composition comprising a compound of formula (I), or pharmaceutically acceptable salt or enantiomer or diastereomer thereof for use in the treatment of HBV infection.

Indications and Methods of Treatment

The compounds of the invention can inhibit cccDNA and have anti-HBV activity. Accordingly, the compounds of the invention are useful for the treatment or prophylaxis of HBV infection.

The invention relates to the use of a compound of formula (I) for the inhibition of cccDNA.

The invention also relates to the use of a compound of formula (I) for the inhibition of HBeAg.

The invention further relates to the use of a compound of formula (I) for the inhibition of HBsAg.

The invention relates to the use of a compound of formula (I) for the inhibition of HBV DNA.

The invention relates to the use of a compound of formula (I) for the treatment or prophylaxis of HBV infection.

The use of a compound of formula (I) for the preparation of medicaments useful in the treatment or prophylaxis diseases that are related to HBV infection is an object of the invention.

The invention relates in particular to the use of a compound of formula (I) for the preparation of a medicament for the treatment or prophylaxis of HBV infection.

Another embodiment includes a method for the treatment or prophylaxis of HBV infection, which method comprises administering an effective amount of a compound of Formula (I), or enantiomers, diastereomers, prodrugs or pharmaceutically acceptable salts thereof.

BRIEF DESCRIPTION OF THE FIGURE(S)

FIG. 1: the result of Example 1 in cccDNA Southern Blot assay, it indicates that Example 1 dose-dependently reduced cccDNA level in HepDES19 cells.

EXAMPLES

The invention will be more fully understood by reference to the following examples. They should not, however, be construed as limiting the scope of the invention.

Abbreviations used herein are as follows:
ACN: acetonitrile
$BBr_3$: boron tribromide
DMAP: 4-dimethylaminopyridine
DME: dimethoxyethane
DMF: N,N-dimethylformamide
$EC_{50}$: the molar concentration of an inhibitor, which produces 50% of the maximum possible response for that inhibitor.
FBS: fetal bovine serum
$H_2O_2$: hydrogen peroxide
HPLC: high performance liquid chromatography
hr(s): hour(s)
min: minute
MS (ESI): mass spectroscopy (electron spray ionization)
Ms: methylsulfonyl
NCS: N-chlorosuccinimide
NMP: N-methyl-2-pyrrolidone
obsd.: observed
PE: petroleum ether
PPA: polyphosphoric acid
$PPh_3$: triphenylphosphine
Py: pyridine
rt: room temperature
Sphos: 2-dicyclohexylphosphino-2',6'-dimethoxybiphenyl
Tf: trifluoromethanesulfonyl
TFA: trifluoroacetic acid
TFAA: trifluoroacetic anhydride TMS: trimethylsilyl
Ts: p-tolylsulfonyl
δ: chemical shift General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μm; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp $C_{18}$ (5 μm, OBD™ 30×100 mm) column or SunFire™ Perp $C_{18}$ (5 μm, OBD™ 30×100 mm) column.

LC/MS spectra were obtained using a Waters UPLC-SQD Mass. Standard LC/MS conditions were as follows (running time 3 minutes):

Acidic condition: A: 0.1% formic acid and 1% acetonitrile in $H_2O$; B: 0.1% formic acid in acetonitrile;

Basic condition: A: 0.05% $NH_3 \cdot H_2O$ in $H_2O$; B: acetonitrile.

Mass spectra (MS): generally only ions which indicate the parent mass are reported, and unless otherwise stated the mass ion quoted is the positive mass ion $(M+H)^+$.

NMR Spectra were obtained using Bruker Avance 400 MHz.

All reactions involving air-sensitive reagents were performed under an argon atmosphere. Reagents were used as received from commercial suppliers without further purification unless otherwise noted.

Preparative Examples

Intermediate 1: methyl 3-(2-hydroxyethoxy)cyclobutanecarboxylate

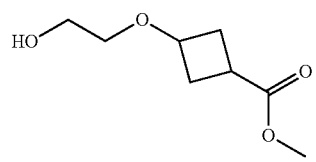

Int-1

Step 1: Preparation of 2-benzyloxyethoxy(trimethyl)silane

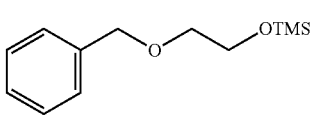

Int-1a

To a solution of 2-benzyloxyethanol (20.0 g, 131.4 mmol) and TEA (20.0 g, 197.1 mmol) in dichloromethane (200 mL) cooled at 0° C. was added trimethylsilyl chloride (17.1 g, 157.7 mmol) and the mixture was then stirred at 25° C. for 16 hours. After the reaction was completed, the mixture was concentrated in vacuo and the residue was purified by column chromatography on silica gel (elution with PE:EtOAc=50:1 to 10:1) to give the 2-benzyloxyethoxy(trimethyl)silane (25.0 g, 84.9%) as a colorless oil.

Step 2: Preparation of methyl 3-(2-benzyloxyethoxy)cyclobutanecarboxylate

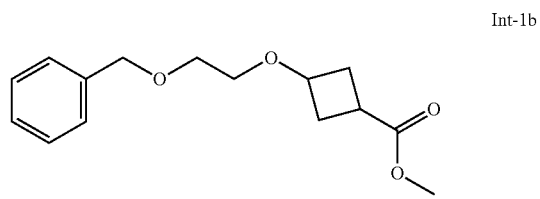 [SMILES: COC(=O)C1CC(OCCOCc2ccccc2)C1]

Int-1b

To a solution of 2-benzyloxyethoxy(trimethyl)silane (25.0 g, 111.4 mmol) and methyl 3-oxocyclobutanecarboxylate (CAS #: 4934-99-0, Cat. #: PB01390, from PharmaBlock (Nanjing) R&D Co. Ltd, 15.0 g, 117.0 mmol) in dichloromethane (200 mL) was added trimethylsilyl trifluoromethanesulfonate (12.4 g, 55.7 mmol) dropwise at −78° C. After addition, the mixture was stirred at −78° C. for additional 1 hour and then to the resulting mixture was added triethylsilane (14.25 g, 122.57 mmol). After addition, the resulting mixture was warmed to room temperature and stirred at room temperature for 1 hour. After the reaction was completed, the mixture was washed with saturated $NH_4Cl$ solution, brine, dried over anhydrous sodium sulfate, and concentrated in vacuo. The residue was purified by column chromatography on silica gel (elution with PE/EtOAc=100:1-50:1) to give methyl 3-(2-benzyloxyethoxy)cyclobutanecarboxylate (28 g, 95.1%) as a colorless oil. MS obsd. $(ESI^+)$ $[(M+H)^+]$: 265.1.

Step 3: Preparation of methyl 3-(2-hydroxyethoxy)cyclobutanecarboxylate

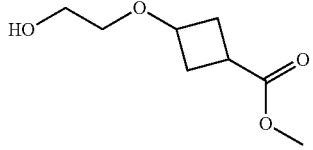

Int-1

To a solution of methyl 3-(2-benzyloxyethoxy)cyclobutanecarboxylate (28.0 g, 105.9 mmol) in MeOH (300.0 mL) was added $Pd(OH)_2$(wet) (1.48 g, 10.6 mmol) at room temperature and the mixture was then hydrogenated under $H_2$ atmosphere at room temperature overnight. After the reaction was completed, the reaction was filtered through silica gel pad and the filtrate was concentrated in vacuo to give 18 g crude methyl 3-(2-hydroxyethoxy)cyclobutanecarboxylate (18 g, 97.6%) as a colorless oil.

Intermediate 2: methyl 3-[2-(p-tolylsulfonyloxy) ethoxy]cyclobutanecarboxylate

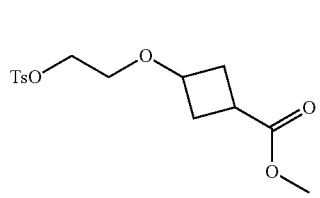

Int-2

To a solution of methyl 3-(2-hydroxyethoxy)cyclobutanecarboxylate (5 g, 28.7 mmol) and DMAP (5.26 g, 43.1 mmol) in dichloromethane (80 mL) was added 4-methylbenzene-1-sulfonyl chloride (6.02 g, 31.6 mmol) at room temperature and the mixture was then stirred at room temperature overnight. After the reaction was completed, the mixture was washed with 1N HCl (25 mL), water (15 mL), saturated NaHCO$_3$ solution, brine and concentrated in vacuo to give the crude methyl 3-[2-(p-tolylsulfonyloxy)ethoxy]cyclobutanecarboxylate (8.1 g, 85.6%) as a colorless oil, which was used in next step directly without further purification. MS obsd. (ESI$^+$) [(M+H)$^+$]: 329.2.

Intermediate 3: methyl 3-[2-(4-formylphenoxy) ethoxy]cyclobutanecarboxylate

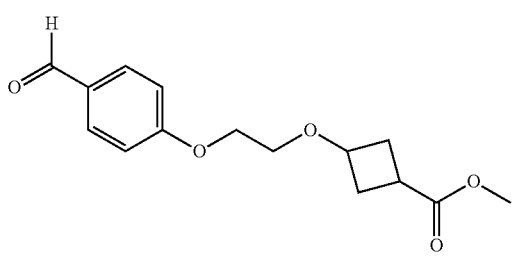

Int-3

To a solution of 4-hydroxybenzaldehyde (5.0 g, 16.38 mmol) and methyl 3-[2-(p-tolylsulfonyloxy)ethoxy]cyclobutanecarboxylate (5.38 g, 16.38 mmol) in DMF (50 mL) was added K$_2$CO$_3$ (4.53 g, 32.75 mmol). The mixture was stirred at 60° C. for 12 hours. The resulting mixture was then poured into water (200 mL) and extracted with EtOAc (200 mL) three times. The combined organic layer was washed with brine, dried over Na$_2$SO$_4$ and concentrated in vacuo. The residue was purified by column chromatography on silica gel (elution with PE:EtOAc=50:1~10:1) to give methyl 3-[2-(4-formylphenoxy)ethoxy]cyclobutanecarboxylate (3.6 g 78.99%) as a yellow solid. MS obsd. (ESI$^+$) [(M+H)$^+$]: 279.1.

Intermediate 4: cis-ethyl 3-[2-(4-formylphenoxy) ethoxy]cyclobutanecarboxylate

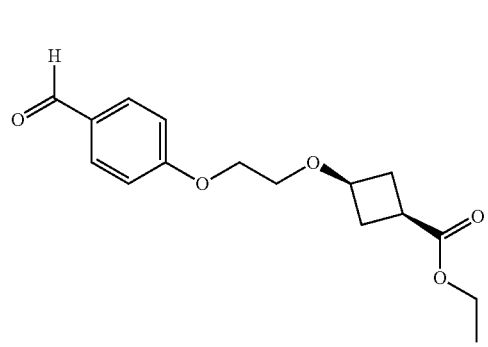

Int-4

Step 1: Preparation of 2-(4-formylphenoxy)ethyl trifluoromethanesulfonate

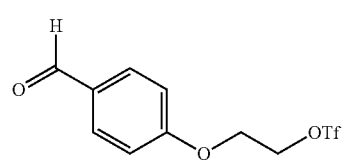

Int-4a

To a solution of 4-(2-hydroxyethoxy)benzaldehyde (3 g, 18.1 mmol) and 2,6-dimethylpyridine (3.87 g, 4.21 mL, 36.1 mmol) in dichloromethane (40 mL) was added trifluoromethanesulfonic anhydride (9.17 g, 5.33 mL, 32.5 mmol) at −30° C. and the mixture was then stirred at 0° C. for 1 hour. The mixture was then washed with 1 N HCl (20 mL) twice, water (20 mL) twice, brine (20 mL), dried over anhydrous Na$_2$SO$_4$ and concentrated in vacuo to give the crude 2-(4-formylphenoxy)ethyl trifluoromethanesulfonate (5.4 g, 100%), which was used in the next step directly without further purification. MS obsd. (ESI$^+$) [(M+H)$^+$]: 299.1.

Step 2: Preparation of cis-ethyl 3-[2-(4-formylphenoxy)ethoxy]cyclobutanecarboxylate

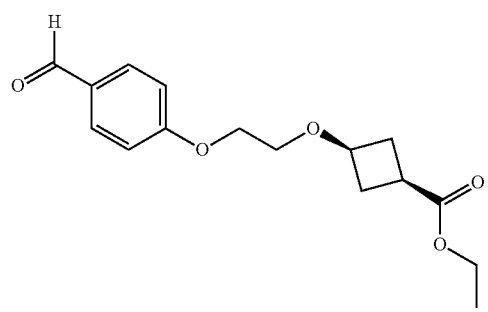

Int-4

To a solution of ethyl 3-hydroxycyclobutanecarboxylate (CAS #: 17205-02-6, Cat. #: PBN20120730, from PharmaBlock (Nanjing) R&D Co. Ltd, 2.6 g, 18 mmol, the ratio of cis isomer:trans isomer=10:1) in THF (20 mL) was added NaH (793 mg, 19.8 mmol) portion wise at 0° C. and the mixture was then stirred at 0° C. for 30 minutes. Then to the resulting mixture was added the solution of 2-(4-formylphenoxy)ethyl trifluoromethanesulfonate (5.4 g, 18.1 mmol, crude) in THF (40 mL) dropwise at 0° C. After addition, the mixture was poured into ice-water (50 mL) and extracted with dichloromethane (50 mL) three times. The combined organic layer was washed with brine, dried over anhydrous Na$_2$SO$_4$ and concentrated in vacuo. The residue was purified by column chromatography on silica gel (elution with PE:EtOAc=100:1 to 3:1) to give cis-ethyl 3-[2-(4-formylphenoxy)ethoxy]cyclobutanecarboxylate as a yellow solid (1.7 g, 32% yield). $^1$H NMR (DMSO-d$_6$, 400 MHz): δ ppm 9.78-9.94 (m, 1H), 7.74-7.91 (m, 2H), 7.07-7.19 (m, 2H), 4.19 (dd, J=3.85, 5.32 Hz, 2H), 4.02-4.10 (m, 2H), 3.90-4.00 (m, 1H), 3.66 (dd, J=3.79, 5.26 Hz, 2H), 2.60-2.73 (m, 1H), 2.41-2.48 (m, 2H), 1.93-2.05 (m, 2H), 1.10-1.23 (m, 3H). The trans isomer was not collected in the purification.

Intermediate 5: methyl 3-methylsulfonyloxycyclobutanecarboxylate

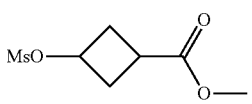
Int-5

To a solution of methyl 3-hydroxycyclobutanecarboxylate (1 g, 7.68 mmol) and TEA (1.17 g, 1.61 mL, 11.5 mmol) in dichloromethane (10 mL) was added methanesulfonyl chloride (1.14 g, 778 μL, 9.99 mmol) at 0° C. and the mixture was then stirred at room temperature overnight. The mixture was then diluted with dichloromethane (50 mL), the resulting solution was then washed with water (20 mL) twice, saturated NaHCO$_3$ (20 mL) twice, brine (20 mL), dried over anhydrous Na$_2$SO$_4$ and concentrated in vacuo to give the crude methyl 3-methylsulfonyloxycyclobutanecarboxylate (1.6 g, 100%) as a colorless oil. MS obsd. (ESI$^+$) [(M+H)$^+$]: 209.2.

Example 1

3-[2-[4-(8-chloro-4-oxo-chromen-2-yl)phenoxy]ethoxy]cyclobutanecarboxylic acid

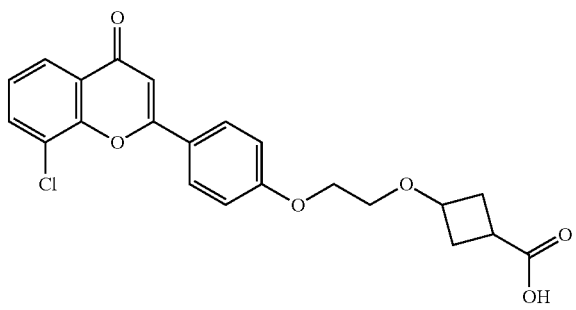
1

Step 1: Preparation of (E)-1-(3-chloro-2-hydroxyphenyl)-3-[4-(2-hydroxyethoxy)phenyl]prop-2-en-1-one

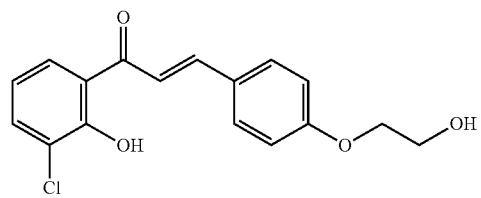
1a

To a solution of 1-(3-chloro-2-hydroxy-phenyl) ethanone (8 g, 46.9 mmol) and 4-(2-hydroxyethoxy) benzaldehyde (7.79 g, 46.9 mmol) in EtOH (150 ml) was added KOH (5.26 g, 93.8 mmol) at room temperature and the mixture was then stirred at 100° C. for 3 hours. After the reaction was completed, the resulting mixture was adjusted to pH~4 by 2N HCl to yield a suspension. The solid was collected by filtration and dried in vacuo to give the crude (E)-1-(3-chloro-2-hydroxy-phenyl)-3-[4-(2-hydroxyethoxy)phenyl] prop-2-en-1-one (14 g, 93.7%) as a light yellow solid. MS obsd. (ESI$^+$) [(M+H)$^+$]: 329.2.

Step 2: Preparation of 8-chloro-2-[4-(2-hydroxyethoxy)phenyl]chromen-4-one

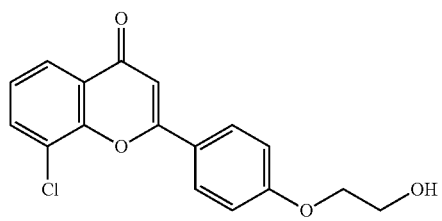
1b

To a solution of (E)-1-(3-chloro-2-hydroxy-phenyl)-3-[4-(2-hydroxyethoxy)phenyl]prop-2-en-1-one (14 g, 43.9 mmol) in DMSO (50 mL) was added I$_2$ (557 mg, 2.2 mmol) at room temperature and the mixture was then stirred at 140° C. for 3 hours. After the reaction was completed, to the mixture was added saturated NaHSO$_3$ solution (10 mL) and water (40 mL). The resulting suspension was filtered, the solid was collected and dried in vacuo to give the crude 8-chloro-2-[4-(2-hydroxyethoxy)phenyl]chromen-4-one (12 g, 86.3%) as a yellow solid. MS obsd. (ESI$^+$) [(M+H)$^+$]: 317.2.

Step 3: Preparation of 3-[2-[4-(8-chloro-4-oxo-chromen-2-yl)phenoxy]ethoxy]cyclobutanecarboxylic acid

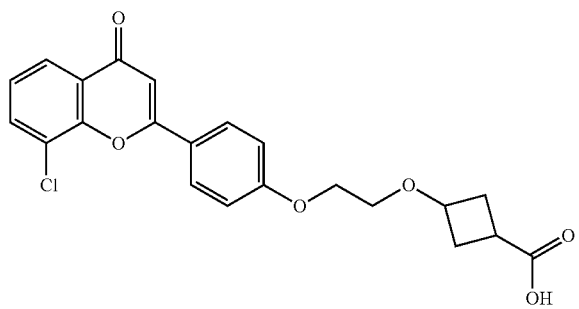

To a solution of 8-chloro-2-[4-(2-hydroxyethoxy)phenyl]chromen-4-one (2 g, 6.31 mmol) in DMSO (20 mL) was added sodium hydride (1.14 g, 28.4 mmol) at room temperature. The mixture was stirred at room temperature for 30 minutes and then to the resulting mixture was added methyl 3-((methylsulfonyl)oxy)cyclobutanecarboxylate (5.26 g, 25.3 mmol) within 1 hour. After addition, the mixture was stirred at room temperature for another 4 hours. After the reaction was completed, the reaction was adjusted to pH~4 by addition of 1N HCl and diluted with water (60 mL). The resulting mixture was extracted by EtOAc (60 mL) three times. The combined organic layer was washed with brine, dried over anhydrous $Na_2SO_4$ and concentrated in vacuo. The residue was purified by preparative HPLC to give 3-[2-[4-(8-chloro-4-oxo-chromen-2-yl)phenoxy]ethoxy]cyclobutanecarboxylic acid (1.67 g, 62.7%) as a white solid. The solid was further purified by supercritical fluid chromatography (SFC) to give cis-3-[2-[4-(8-chloro-4-oxo-chromen-2-yl)phenoxy]ethoxy]cyclobutanecarboxylic acid (Example 1-A) and trans-3-[2-[4-(8-chloro-4-oxo-chromen-2-yl)phenoxy]ethoxy]cyclobutanecarboxylic acid (Example 1-B). The configuration of Example 1-A and Example 1-B were determined by NOESY.

Example 1: $^1$H NMR (DMSO-$d_6$, 400 MHz): δ ppm 12.17-12.07 (m, 1H), 8.12-8.05 (m, 2H), 8.00 (d, J=7.8 Hz, 2H), 7.49 (t, J=7.8 Hz, 1H), 7.18 (d, J=9.0 Hz, 2H), 7.07 (s, 1H), 4.23-4.15 (m, 2H), 4.06-3.90 (m, 1H), 3.70-3.64 (m, 2H), 2.64-2.54 (m, 1H), 2.48-2.36 (m, 2H), 2.21-1.96 (m, 2H). MS obsd. (ESI$^+$) [(M+H)$^+$]: 415.1.

Example 1-A: $^1$H NMR (DMSO-$d_6$, 400 MHz): δ ppm 12.13 (s, 1H), 8.12-8.05 (m, 2H), 8.00 (d, J=7.8 Hz, 2H), 7.49 (t, J=7.9 Hz, 1H), 7.20-7.15 (m, 2H), 7.07 (s, 1H), 4.22-4.16 (m, 2H), 3.99-3.88 (m, 1H), 3.67 (dd, J=3.8, 5.3 Hz, 2H), 2.64-2.54 (m, 1H), 2.48-2.40 (m, 2H), 2.04-1.95 (m, 2H). MS obsd. (ESI$^+$) [(M+H)$^+$]: 415.1.

Example 1-B: $^1$H NMR (DMSO-$d_6$, 400 MHz): δ ppm 12.12 (br. s., 1H), 8.09 (d, J=9.0 Hz, 2H), 8.00 (d, J=8.1 Hz, 2H), 7.49 (t, J=7.8 Hz, 1H), 7.18 (d, J=9.0 Hz, 2H), 7.07 (s, 1H), 4.23-4.17 (m, 2H), 3.70-3.63 (m, 2H), 2.97-2.87 (m, 1H), 2.39 (ddd, J=3.5, 7.0, 13.2 Hz, 2H), 2.21-2.11 (m, 2H). MS obsd. (ESI$^+$) [(M+H)$^+$]: 415.1.

Example 1-A

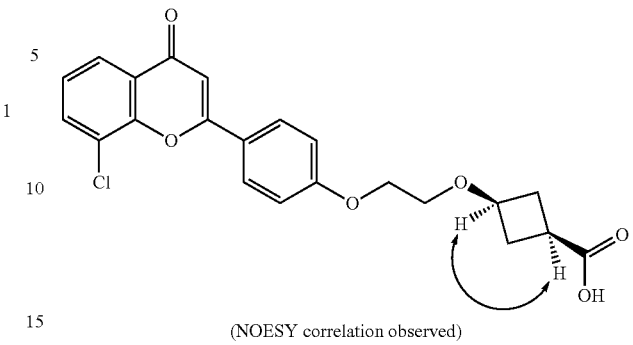

(NOESY correlation observed)

Example 1-B

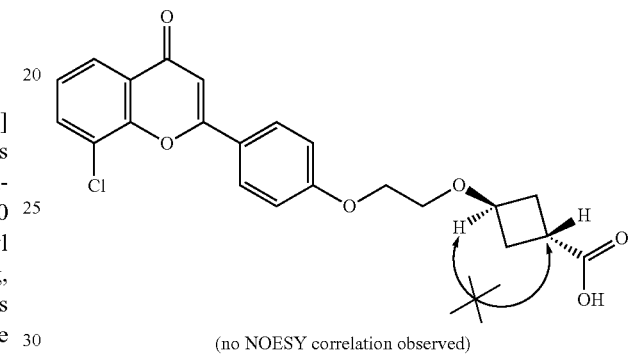

(no NOESY correlation observed)

Example 2

Ethyl 3-[2-[4-(8-chloro-4-oxo-chromen-2-yl)phenoxy]ethoxy]cyclobutanecarboxylate

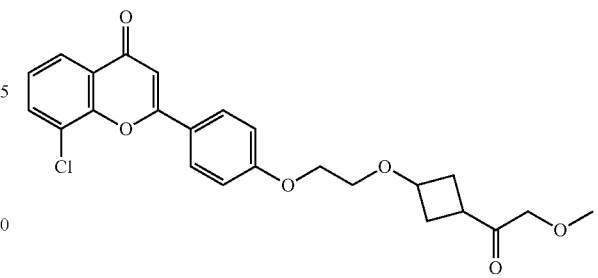

To a mixture of 3-[2-[4-(8-chloro-4-oxo-chromen-2-yl)phenoxy]ethoxy]cyclobutanecarboxylic acid (0.4 g, 0.96 mmol) in EtOH (10 mL) was added $H_2SO_4$ (0.2 mL) and the mixture was then stirred at 60° C. for 12 hours. After the reaction was completed, the mixture was poured into water (50 mL) and the resulting mixture was extracted with EtOAc (50 mL) three times. The combined organic layer was washed with brine, dried over anhydrous $Na_2SO_4$ and concentrated in vacuo, the residue was then purified by preparative HPLC to give ethyl 3-[2-[4-(8-chloro-4-oxo-chromen-2-yl)phenoxy]ethoxy]cyclobutanecarboxylate (305.0 mg, 71.7%) as a yellow solid. $^1$H NMR (DMSO-$d_6$, 400 MHz): δ ppm 8.15-8.12 (m, 1H), 7.98-7.96 (d, J=8.0 Hz, 2H), 7.76-7.74 (d, J=8.0 Hz, 2H), 7.08-7.06 (m, 2H), 6.79 (s, 1H), 4.32-4.14 (m, 5H), 3.78-3.76 (m, 2H), 2.57-2.55 (m, 3H), 2.31-2.29 (m, 2H), 1.3-1.25 (m, 3H). MS obsd. (ESI⁺) [(M+H)⁺]: 443.1.

Example 3

3-[2-[4-(8-chloro-4-oxo-chromen-2-yl)phenoxy]ethoxy]benzoic acid

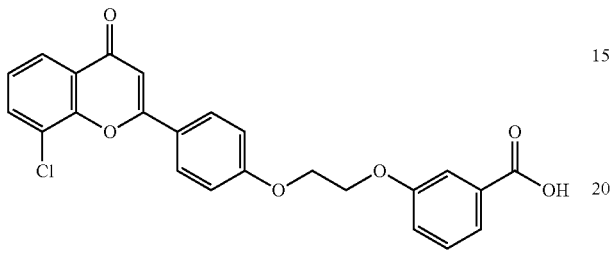

3

Step 1: Preparation of (E)-1-(3-chloro-2-hydroxy-phenyl)-3-(4-methoxyphenyl)prop-2-en-1-one

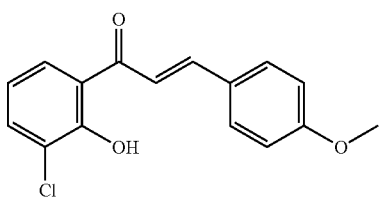

3a

A mixture of 1-(3-chloro-2-hydroxy-phenyl)ethanone (2.5 g, 14.7 mmol), 4-methoxybenzaldehyde (2 g, 14.7 mmol) and KOH (1.64 g, 29.3 mmol) in the EtOH (25 mL) was stirred at 100° C. for 3 hours. The mixture was then adjusted to PH~4 by addition of 2N HCl and the resulting suspension was filtered. The solid was collected and dried in vacuo to give the crude (E)-1-(3-chloro-2-hydroxy-phenyl)-3-(4-methoxyphenyl)prop-2-en-1-one (3.3 g, 78%) as a yellow solid, which was used in the next step directly without further purification. MS obsd. (ESI⁺) [(M+H)⁺]: 289.1.

Step 2: Preparation of 8-chloro-2-(4-methoxyphenyl)chromen-4-one

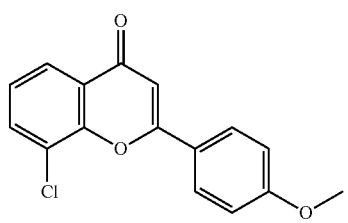

3b

To a solution of (E)-1-(3-chloro-2-hydroxy-phenyl)-3-(4-methoxyphenyl)prop-2-en-1-one (5.3 g, 18.4 mmol) in DMSO (60 mL) was added I₂ (466 mg, 1.84 mmol) and then the mixture was stirred at 140° C. for 3 hours. After the reaction was completed, the reaction was cooled to room temperature, quenched with saturated NaHSO₃ solution (10 mL) and diluted with water 100 mL. The resulting suspension was filtered and the solid was collected and dried in vacuo to give the 8-chloro-2-(4-methoxyphenyl)chromen-4-one (5 g, 95% yield) as a yellow solid, which was used in the next step directly without further purification. MS obsd. (ESI⁺) [(M+H)⁺]: 287.2.

Step 3: Preparation of 8-chloro-2-(4-hydroxyphenyl)chromen-4-one

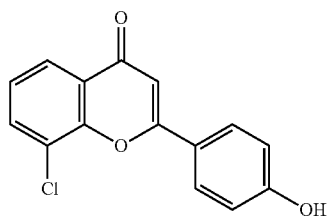

3c

To a solution of 8-chloro-2-(4-methoxyphenyl)chromen-4-one (5 g, 17.4 mmol) in dichloromethane (40 mL) was added BBr₃ (1 M solution in dichloromethane, 69.8 mL, 69.8 mmol) at room temperature, the mixture was stirred at room temperature overnight. After the reaction was completed, the mixture was concentrated in vacuo and the residue was suspended in saturated NH₄Cl solution (30 mL). The solid was collected by filtration and dried in vacuo to give the crude 8-chloro-2-(4-hydroxyphenyl)chromen-4-one, which was used in the next step directly without further purification. MS obsd. (ESI⁺) [(M+H)⁺]: 272.1.

Step 4: Preparation of 2-[4-(2-bromoethoxy)phenyl]-8-chloro-chromen-4-one

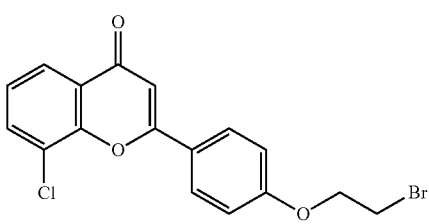

3d

To a solution of 8-chloro-2-(4-hydroxyphenyl)chromen-4-one (800.0 mg, 2.94 mmol) and K₂CO₃ (1.2 g, 8.82 mmol) in DMF (20 mL) was added 1,2-dibromoethane (2.76 g, 14.7 mmol) at room temperature and the mixture was then stirred at 80° C. for 12 hours. After the reaction was completed, the mixture was diluted with water (30 mL) and extracted with EtOAc (50 mL) three times. The combined organic layer was washed with brine, dried over anhydrous Na₂SO₄ and concentrated in vacuo to give crude 2-[4-(2-bromoethoxy)phenyl]-8-chloro-chromen-4-one (1.0 g, 89.7%) as a yellow solid, which was used in next step directly without further purification. MS obsd. (ESI⁺) [(M+H)⁺]: 379.0.

Step 5: Preparation of methyl 3-[2-[4-(8-chloro-4-oxo-chromen-2-yl)phenoxy]ethoxy]benzoate

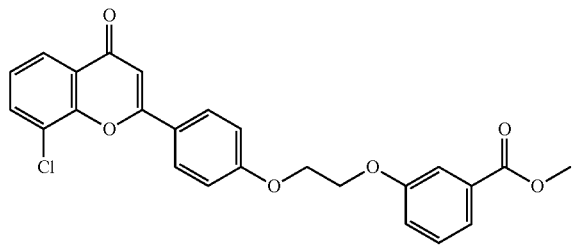

3e

To a solution of 2-[4-(2-bromoethoxy)phenyl]-8-chloro-chromen-4-one (100.0 mg, 0.26 mmol) and methyl 3-hydroxybenzoate (48.0 mg, 0.32 mmol) in DMSO (3.0 mL) was added K$_2$CO$_3$ (107.6 mg, 0.78 mmol) at room temperature. Then the mixture was stirred at room temperature under N$_2$ for 10 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give crude methyl 3-[2-[4-(8-chloro-4-oxo-chromen-2-yl)phenoxy]ethoxy]benzoate (117 mg, 100%) as a yellow solid, which was used in next step directly without further purification. MS obsd. (ESI$^+$) [(M+H)$^+$]: 451.2.

Step 6: Preparation of 3-[2-[4-(8-chloro-4-oxo-chromen-2-yl)phenoxy]ethoxy]benzoic acid

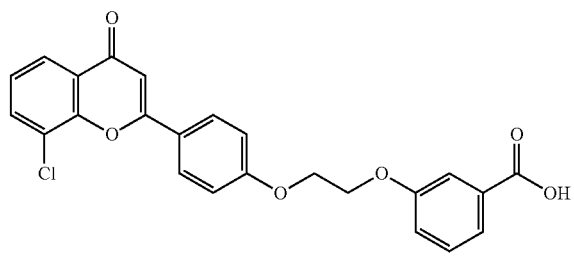

3

To a solution of methyl 3-[2-[4-(8-chloro-4-oxo-chromen-2-yl)phenoxy]ethoxy]benzoate (117.0 mg, 0.26 mmol) in the mixed solvent of MeOH (20 mL) and H$_2$O (3 mL) was added LiOH·H$_2$O (70.0 mg, 1.67 mmol) at room temperature. The mixture was then stirred at room temperature for 48 hours. After the reaction was completed, the reaction was adjusted to pH~4 by addition of 4N HCl. The resulting mixture was then concentrated in vacuo, the residue was purified by preparative HPLC to give 3-[2-[4-(8-chloro-4-oxo-chromen-2-yl)phenoxy]ethoxy]benzoic acid (8.0 mg, 7.0%) as a white solid. $^1$H NMR (DMSO-d$_6$, 400 MHz): δ ppm 8.07-8.15 (m, 2H), 8.00 (d, J=7.8 Hz, 2H), 7.39-7.59 (m, 4H), 7.24 (d, J=8.8 Hz, 3H), 7.08 (s, 1H), 4.45 ppm (dd, J=18.3, 4.5 Hz, 4H). MS obsd. (ESI$^+$) [(M+H)$^+$]: 437.2.

Example 4

Ethyl 2-[2-[4-(8-chloro-4-oxo-chromen-2-yl)phenoxy]ethoxy]cyclopropanecarboxylate

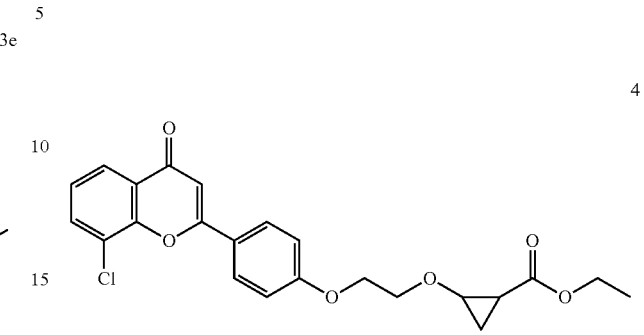

4

Step 1: Preparation of 2-vinyloxyethyl 4-methylbenzenesulfonate

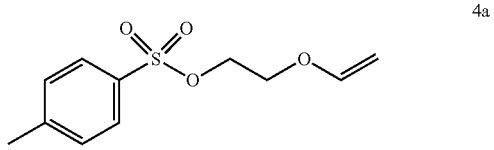 [SMILES: C=COCCOS(=O)(=O)c1ccc(C)cc1]

4a

To a solution of 2-vinyloxyethanol (4.0 g, 45.4 mmol) and TEA (12.66 mL, 90.8 mmol) in dichloromethane (50 mL) was added 4-methylbenzene-1-sulfonyl chloride (12.98 g, 68.1 mmol) at 0° C. and the mixture was then stirred at room temperature for 4 hour. After the reaction was completed, the mixture was concentrated in vacuo. The residue was purified by column chromatography on silica gel (elution with petroleum ether:EtOAc=50:1~5:1) to give 2-vinyloxyethyl 4-methylbenzenesulfonate (10.5 g, 95.46%). MS obsd. (ESI$^+$) [(M+H)$^+$]:243.1.

Step 2: Preparation of ethyl 2-[2-(p-tolylsulfonyloxy)ethoxy]cyclopropanecarboxylate

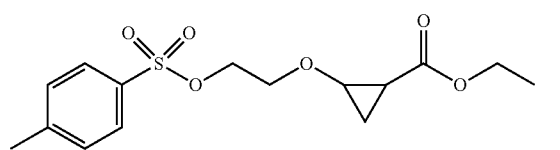

4b

To a solution of 2-vinyloxyethyl 4-methylbenzenesulfonate (1.0 g, 4.13 mmol) and rhodium acetate (0.1 g, 0.230 mmol) cooled at 0° C. in dichloromethane (10 mL) was added ethyl 2-diazoacetate (0.57 g, 4.95 mmol) dropwise. After addition, the mixture was stirred at room temperature for 12 hours. After the reaction was completed, the resulting mixture was filtered and the filtrate was concentrated in vacuo. The residue was purified by column chromatography on silica gel (elution with petroleum ether: EtOAc=50:1~5:1) to give ethyl 2-[2-(p-tolylsulfonyloxy)ethoxy]cyclopropanecarboxylate (1.1 g, 81.16%). MS obsd. (ESI$^+$) [(M+H)$^+$]:329.1.

Step 3: Preparation of ethyl 2-[2-[4-(8-chloro-4-oxo-chromen-2-yl)phenoxy]ethoxy]cyclopropanecarboxylate

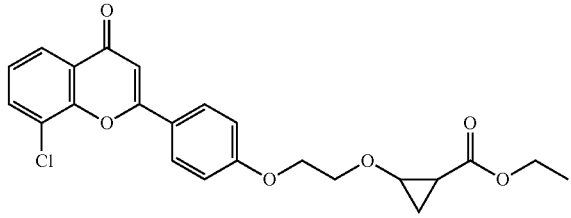

To a mixture of ethyl 2-[2-(p-tolylsulfonyloxy)ethoxy]cyclopropanecarboxylate (145.72 mg, 0.44 mmol) and 8-chloro-2-(4-hydroxyphenyl)chromen-4-one (110.0 mg, 0.40 mmol) in DMF (5 mL) was added $K_2CO_3$ (167.2 mg, 1.2 mmol) at room temperature and the mixture was then stirred at 80° C. for 12 hours. After the reaction was completed, to the mixture was added $H_2O$ (10 mL) and the resulting mixture was extracted with ethyl acetate (10 mL) three times. The combined organic layer was washed with brine, dried over anhydrous $Na_2SO_4$, and concentrated in vacuo to give the crude ethyl 2-[2-[4-(8-chloro-4-oxo-chromen-2-yl)phenoxy]ethoxy]cyclopropanecarboxylate. The crude was further purified by preparative HPLC to give two diastereomers with cis- and trans-configuration, one of which is characterized as Example 4-A (40 mg, 20.4%) and the other is Example 4-B (60 mg, 35%).

Example 4-A: $^1$H NMR (DMSO-$d_6$, 400 MHz): δ ppm 8.15-8.06 (m, J=8.9 Hz, 2H), 8.00 (d, J=7.9 Hz, 2H), 7.49 (t, J=7.8 Hz, 1H), 7.21-7.14 (m, J=8.9 Hz, 2H), 7.06 (s, 1H), 4.23 (t, J=4.4 Hz, 2H), 4.05 (dq, J=1.8, 7.1 Hz, 2H), 3.95-3.81 (m, 2H), 3.70 (dt, J=2.1, 4.4 Hz, 1H), 1.84-1.76 (m, 1H), 1.34-1.23 (m, 1H), 1.22-1.12 (m, 4H). MS obsd. (ESI$^+$) [(M+H)$^+$]: 429.1.

Example 4-B: $^1$H NMR (DMSO-$d_6$, 400 MHz): δ ppm 8.09 (d, J=9.0 Hz, 2H), 8.00 (d, J=7.8 Hz, 2H), 7.50 (t, J=7.9 Hz, 1H), 7.16 (d, J=9.0 Hz, 2H), 7.07 (s, 1H), 4.19 (br d, J=3.3 Hz, 2H), 4.08-4.01 (m, 2H), 3.87-3.80 (m, 1H), 3.79-3.60 (m, 2H), 1.80-1.73 (m, 1H), 1.35 (d, J=4.8 Hz, 1H), 1.21-1.15 (m, 4H). MS obsd. (ESI$^+$) [(M+H)$^+$]: 429.1.

Example 5-A and Example 5-B

Cis-2-[2-[4-(8-chloro-4-oxo-chromen-2-yl)phenoxy]ethoxy]cyclopropanecarboxylic acid and trans-2-[2-[4-(8-chloro-4-oxo-chromen-2-yl)phenoxy]ethoxy]cyclopropanecarboxylic acid

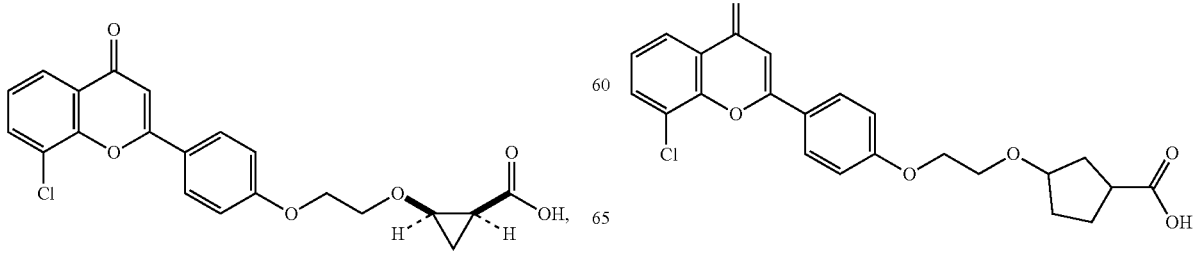

To a solution of ethyl 2-[2-[4-(8-chloro-4-oxo-chromen-2-yl)phenoxy]ethoxy]cyclopropanecarboxylate (520.0 mg, 1.2 mmol) in the mixed solvent of THF (2 mL) and water (2 mL) was added LiOH·$H_2O$ (96 mg, 2.43 mmol). The mixture was stirred at room temperature for 4 hours. After the reaction was completed, the mixture was adjusted to pH~5 by addition of 1N HCl. The resulting mixture was extracted by EtOAc (20 mL) three times. The combined organic layer was washed with brine, dried with anhydrous $Na_2SO_4$ and concentrated in vacuo. The residue was purified by preparative HPLC to give two diastereomers of 2-[2-[4-(8-chloro-4-oxo-chromen-2-yl)phenoxy]ethoxy]cyclopropanecarboxylic acid with cis- and trans-configuration, one of which is characterized as Example 5-A (2.9 mg, 3.6%) and the other is Example 5-B (17 mg, 35.3%).

Example 5-A: $^1$H NMR (DMSO-$d_6$, 400 MHz): δ ppm 8.05 (br d, J=8.5 Hz, 2H), 7.97 (d, J=7.9 Hz, 2H), 7.47 (t, J=7.8 Hz, 1H), 7.15 (br d, J=8.5 Hz, 2H), 7.02 (s, 1H), 4.20-4.11 (m, 2H), 3.86-3.70 (m, 2H), 3.65-3.56 (m, 1H), 1.59 (q, J=7.1 Hz, 1H), 1.31-1.18 (m, 1H), 0.97-0.81 (m, 1H). MS obsd. (ESI$^+$) [(M+H)$^+$]: 401.0.

Example 5-B: $^1$H NMR (DMSO-$d_6$, 400 MHz): δ ppm 8.13 (d, J=8.8 Hz, 2H), 8.04 (d, J=7.9 Hz, 2H), 7.54 (t, J=7.8 Hz, 1H), 7.22 (d, J=8.8 Hz, 2H), 7.10 (s, 1H), 4.27 (br t, J=4.3 Hz, 2H), 3.99-3.85 (m, 2H), 3.63 (br d, J=4.3 Hz, 1H), 1.68 (br t, J=6.9 Hz, 1H), 1.15-1.07 (m, 2H). MS obsd. (ESI$^+$) [(M+H)$^+$]: 401.0.

Example 6

3-[2-[4-(8-chloro-4-oxo-chromen-2-yl)phenoxy]ethoxy]cyclopentanecarboxylic acid

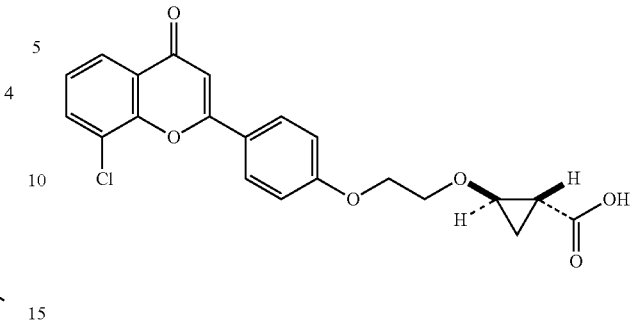

Step 1: Preparation of methyl 3-(2-hydroxyethoxy)cyclopentanecarboxylate

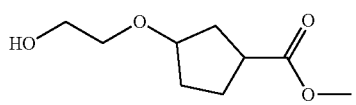

Compound 6a was prepared in analogy to the procedure described for the preparation of Int-1 by using methyl 3-oxocyclopentanecarboxylate as the starting materials instead of methyl 3-oxocyclobutanecarboxylate in Step 2.

Step 2: Preparation of methyl 3-[2-(p-tolylsulfonyloxy)ethoxy]cyclopentanecarboxylate

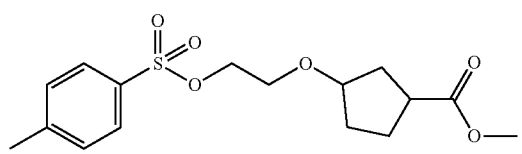

Compound 6b was prepared in analogy to the procedure described for the preparation of Int-2 by using methyl 3-(2-hydroxyethoxy)cyclopentanecarboxylate as the starting materials instead of methyl 3-(2-hydroxyethoxy)cyclobutanecarboxylate in Step 2.

Step 3: Preparation of methyl 3-[2-[4-(8-chloro-4-oxo-chromen-2-yl)phenoxy]ethoxy]cyclopentanecarboxylate

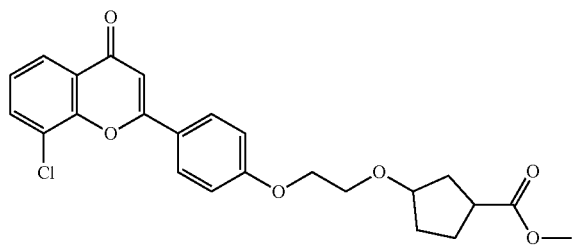

To a solution of methyl 3-[2-(p-tolylsulfonyloxy)ethoxy]cyclopentanecarboxylate (1.0 g, 3.67 mmol) and K$_2$CO$_3$ (1.02 g, 7.33 mmol) in DMF (20 mL) was added 8-chloro-2-(4-hydroxyphenyl)chromen-4-one (compound 3c, 1.38 g, 4.03 mmol). The mixture was then stirred at 80° C. for 4 hours. After the reaction was completed, to the mixture was added H$_2$O (50 mL) and the resulting mixture was extracted with EtOAc (30 mL) three times. The combined organic layer was washed with brine, dried over anhydrous Na$_2$SO$_4$ and concentrated in vacuo to give the crude methyl 3-[2-[4-(8-chloro-4-oxo-chromen-2-yl)phenoxy]ethoxy]cyclopentanecarboxylate (1.6 g, 98.4%) as a yellow solid, which was used in the next step directly without further purification. MS obsd. (ESI$^+$) [(M+H)$^+$]: 443.1.

Step 4: Preparation of 3-[2-[4-(8-chloro-4-oxo-chromen-2-yl)phenoxy]ethoxy]cyclopentanecarboxylic acid

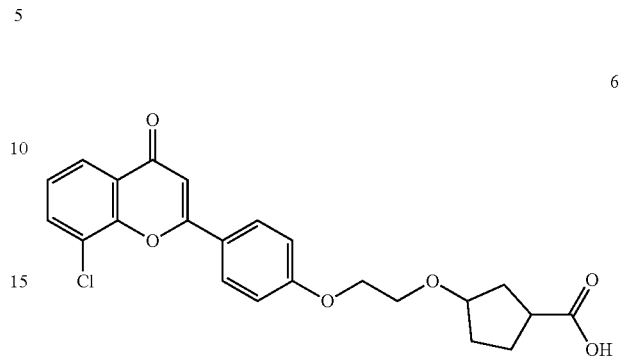

To a solution of methyl 3-[2-[4-(8-chloro-4-oxo-chromen-2-yl)phenoxy]ethoxy]cyclopentanecarboxylate (1.6 g, 3.61 mmol) in the mixed solvent of THF (10 mL) and H$_2$O (10 mL) was added LiOH·H$_2$O (259.55 mg, 10.84 mmol). The mixture was stirred at room temperature for 4 hours. After the reaction was completed, the mixture was adjusted to pH~5 by addition of 1N HCl. The resulting mixture was extracted by EtOAc (20 mL) three times. The combined organic layer was washed with brine, dried with anhydrous Na$_2$SO$_4$ and concentrated in vacuo to give the crude 3-[2-[4-(8-chloro-4-oxo-chromen-2-yl)phenoxy]ethoxy]cyclopentanecarboxylic acid (1.2 g, 77.7%) as a solid.

Example 6: $^1$H NMR (DMSO-d$_6$, 400 MHz): δ ppm 12.07 (br s, 1H), 8.12-8.05 (m, J=8.9 Hz, 2H), 7.99 (d, J=7.9 Hz, 2H), 7.49 (t, J=7.8 Hz, 1H), 7.21-7.14 (m, J=8.9 Hz, 2H), 7.06 (s, 1H), 4.25-4.13 (m, 2H), 4.09-3.88 (m, 1H), 3.76-3.66 (m, 2H), 2.80-2.78 (m, 1H), 1.99-1.78 (m, 4H), 1.75-1.61 (m, 2H). MS obsd. (ESI$^+$) [(M+H)$^+$]: 429.1.

Example 7-A and Example 7-B

Cis-4-[2-[4-(8-chloro-4-oxo-chromen-2-yl)phenoxy]ethoxy]cyclohexanecarboxylic acid and trans-4-[2-[4-(8-chloro-4-oxo-chromen-2-yl)phenoxy]ethoxy]cyclohexanecarboxylic acid

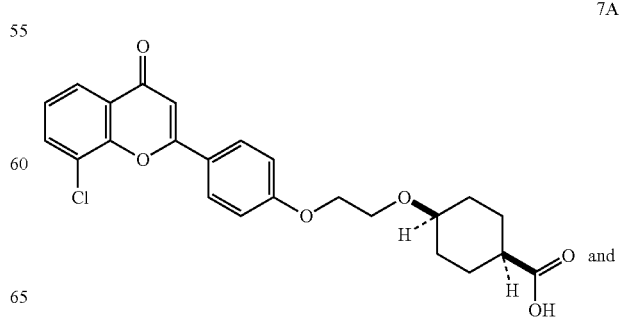

-continued

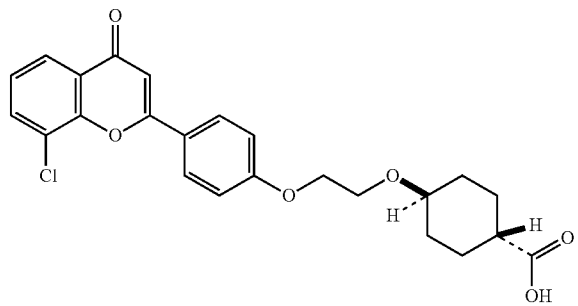

7-B

Step 1: Preparation of methyl 4-(2-hydroxyethoxy)cyclohexanecarboxylate

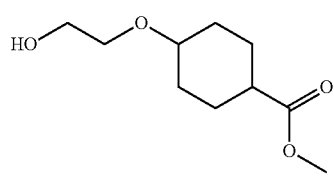

7a

Compound 7a was prepared in analogy to the procedure described for the preparation of Int-1 by using methyl 4-oxocyclohexanecarboxylate as the starting materials instead of methyl 3-oxocyclobutanecarboxylate in Step 2.

Step 2: Preparation of methyl 4-[2-(p-tolylsulfonyloxy)ethoxy]cyclohexanecarboxylate

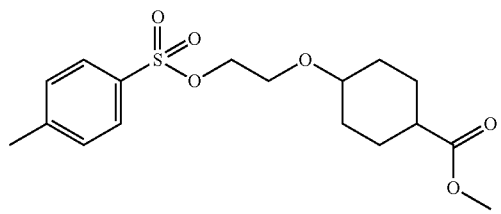

7b

Compound 7b was prepared in analogy to the procedure described for the preparation of Int-2 by using methyl 4-(2-hydroxyethoxy)cyclohexanecarboxylate as the starting materials instead of methyl 3-(2-hydroxyethoxy)cyclobutanecarboxylate in Step 2.

Step 3: Preparation of methyl 4-[2-[4-(8-chloro-4-oxo-chromen-2-yl)phenoxy]ethoxy]cyclohexanecarboxylate 7c To a solution of methyl 4-[2-(p-tolylsulfonyloxy)ethoxy] cyclohexanecarboxylate (1.0 g, 3.67 mmol) and K₂CO₃ (1.02 g, 7.33 mmol) in DMF (20 mL) was added 2-[4-(2-bromoethoxy)phenyl]-8-chloro-chromen-4-one (1.44 g, 4.03 mmol). The mixture was then stirred at 80° C. for 4 hours. After the reaction was completed, to the mixture was added H₂O (50 mL) and the resulting mixture was extracted with EtOAc (30 mL) three times. The combined organic layer was washed with brine, dried over anhydrous Na₂SO₄ and concentrated in vacuo to give the crude methyl 4-[2-[4-(8-chloro-4-oxo-chromen-2-yl)phenoxy]ethoxy]cyclohexanecarboxylate (1.45 g, 86.4%) as a yellow solid, which was used in the next step directly without further purification. MS obsd. (ESI⁺) [(M+H)⁺]: 457.1.

Step 4: Preparation of 4-[2-[4-(8-chloro-4-oxo-chromen-2-yl)phenoxy]ethoxy]cyclohexanecarboxylic acid

7

To a solution of methyl 4-[2-[4-(8-chloro-4-oxo-chromen-2-yl)phenoxy]ethoxy]cyclohexanecarboxylate (1.45 g, 3.17 mmol) in the mixed solvent of THF (10 mL) and H₂O (10 mL) was added LiOH·H₂O (259.55 mg, 10.84 mmol). The mixture was stirred at room temperature for 4 hours. After the reaction was completed, the mixture was adjusted to pH~5 by addition of 1N HCl. The resulting mixture was extracted by EtOAc (20 mL) three times. The combined organic layer was with brine, dried with anhydrous Na₂SO₄ and concentrated in vacuo. The residue was purified by preparative HPLC to give two diastereomers of the 4-[2-[4-(8-chloro-4-oxo-chromen-2-yl)phenoxy]ethoxy]cyclohexanecarboxylic acid with cis- and trans-configuration, one of which is characterized as Example 7-A (720 mg, 51.2%) and the other is Example 7-B (30 mg, 2.1%).

Example 7-A: $^1$H NMR (DMSO-$d_6$, 400 MHz): δ ppm 12.06 (s, 1H), 8.08 (d, J=8.9 Hz, 2H), 8.00 (d, J=7.9 Hz, 2H), 7.49 (t, J=7.9 Hz, 1H), 7.18 (dd, J=2.8, 9.0 Hz, 2H), 7.06 (s, 1H), 4.26-4.17 (m, 2H), 3.78 (td, J=4.5, 16.4 Hz, 2H), 3.31-3.24 (m, 1H), 2.22-2.10 (m, 1H), 2.01 (br d, J=8.9 Hz, 2H), 1.98 (br d, J=13.1 Hz, 2H), 1.39-1.37 (m, 2H), 1.22-1.18 (m, 2H). MS obsd. (ESI$^+$) [(M+H)$^+$]: 443.0.

Example 7-B: $^1$H NMR (DMSO-$d_6$, 400 MHz): δ ppm 12.06 (s, 1H), 8.08 (d, J=8.9 Hz, 2H), 8.00 (d, J=7.9 Hz, 2H), 7.49 (t, J=7.9 Hz, 1H), 7.18 (dd, J=2.8, 9.0 Hz, 2H), 7.06 (s, 1H), 4.26-4.17 (m, 2H), 3.78 (td, J=4.5, 16.4 Hz, 2H), 3.59-3.51 (m, 1H), 2.29-2.27 (m, 1H), 1.68-1.74 (m, 4H), 1.40-1.60 (m, 4H). MS obsd. (ESI$^+$) [(M+H)$^+$]: 443.0.

Example 8

2-[3-[[4-(8-chloro-4-oxo-chromen-2-yl)phenoxy]methyl]cyclobutoxy]acetic acid

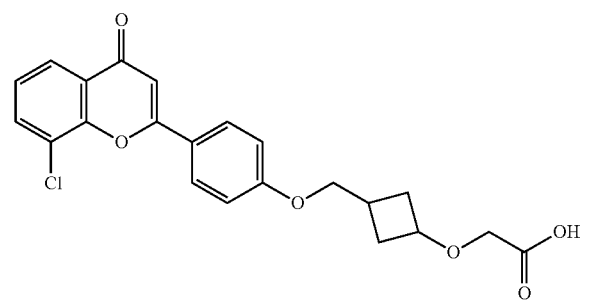

Step 1: Preparation of 3-(hydroxymethyl)cyclobutanol

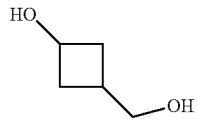

The mixture of methyl 3-oxocyclobutanecarboxylate (3.0 g, 26.3 mmol) in THF (20.0 mL) at −78° C. was added B$_2$H$_6$·Me$_2$S (2.0 mL) at room temperature and the mixture was then stirred at room temperature for 12 hours. After the reaction was completed, the mixture was concentrated in vacuo, the residue was partitioned between dichloromethane (40 mL) and water (50 mL). The mixture was concentrated and extracted with dichloromethane (40.0 mL) and water (50.0 mL). The organic layer was then separated out and the aquatic phase was extracted with dichloromethane (50 mL) twice. The combined organic layer was washed with brine, dried over Na2SO4 and concentrated in vacuo to yield the crude 3-(hydroxymethyl)cyclobutanol (2.0 g, 74.5%) as an oil.

Step 2: Preparation of (3-hydroxycyclobutyl)methyl 4-methylbenzenesulfonate

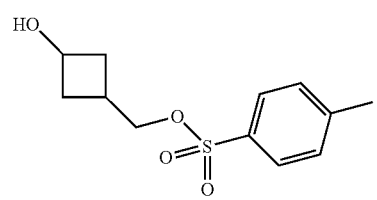

To a solution of 3-(hydroxymethyl)cyclobutanol (2.0 g, 20.0 mmol) and TEA (2.0 g, 20.0 mmol) in dichloromethane (50 mL) was added 4-methylbenzene-1-sulfonyl chloride (4.8 g, 20.0 mmol) at room temperature and the mixture was then stirred at room temperature for 5 hours. After the reaction was completed, the mixture was washed with 1N HCl (25 mL), water (15 mL), saturated NaHCO$_3$ solution, brine and concentrated in vacuo to give the crude (3-hydroxycyclobutyl)methyl 4-methylbenzenesulfonate (1.0 g, 19.4%) as colorless oil, which was used in next step directly without further purification. MS obsd. (ESI$^+$) [(M+H)$^+$]: 257.1.

Step 3: Preparation of 8-chloro-2-[4-[(3-hydroxycyclobutyl)methoxy]phenyl]chromen-4-one

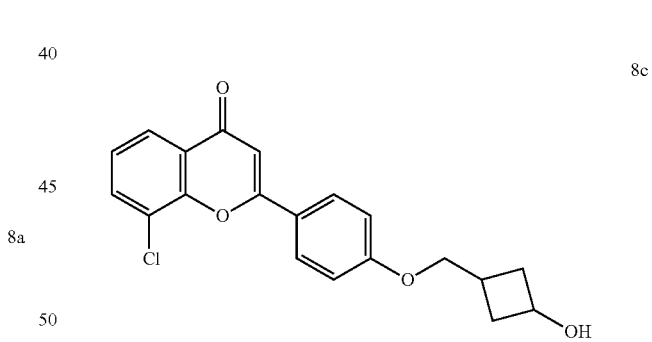

To a solution of 8-chloro-2-(4-hydroxyphenyl)chromen-4-one (1.0 g, 3.7 mmol) and (3-hydroxycyclobutyl)methyl 4-methylbenzenesulfonate (1.0 g, 5.0 mmol) in DMF (10 mL) was added K$_2$CO$_3$ (1.0 g, 10.0 mmol) and the mixture was then stirred at 80° C. for 12 hours. After the reaction was completed, the mixture was diluted with water (50 mL) and extracted with EtOAc (50 mL) three times. The combined organic layer was washed with brine, dried over Na$_2$SO$_4$ and concentrated in vacuo to give the crude 8-chloro-2-[4-[(3-hydroxycyclobutyl)methoxy]phenyl]chromen-4-one (1.0 g, 75.6%) as a yellow solid, which was used in next step directly without further purification. MS obsd. (ESI$^+$) [(M+H)$^+$]:357.1.

Step 4: Preparation of ethyl 2-[3-[[4-(8-chloro-4-oxo-chromen-2-yl)phenoxy]methyl]cyclobutoxy]acetate

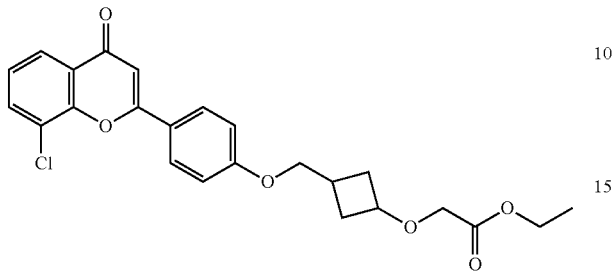

8d

To a mixture of 8-chloro-2-[4-[(3-hydroxycyclobutyl)methoxy]phenyl]chromen-4-one (0.1 g, 0.3 mmol) and ethyl 2-diazoacetate (0.11 g, 1.0 mmol) in THF (10 mL) at 0° C. was added BF$_3$·Et$_2$O (0.1 mL) and the mixture was then stirred at room temperature for 2 hours. After the reaction was completed, the reaction was quenched with 1N HCl and extracted with EtOAc (50 mL) three times. The combined organic layer was washed with brine, dried over anhydrous Na$_2$SO$_4$ and concentrated in vacuo to give the crude ethyl 2-[3-[[4-(8-chloro-4-oxo-chromen-2-yl)phenoxy]methyl]cyclobutoxy]acetate (0.1 g, 75.2%) as a yellow solid, which was used in next step directly without further purification. MS obsd. (ESI$^+$) [(M+H)$^+$]:443.1.

Step 5: Preparation of 2-[3-[[4-(8-chloro-4-oxo-chromen-2-yl)phenoxy]methyl]cyclobutoxy]acetic acid

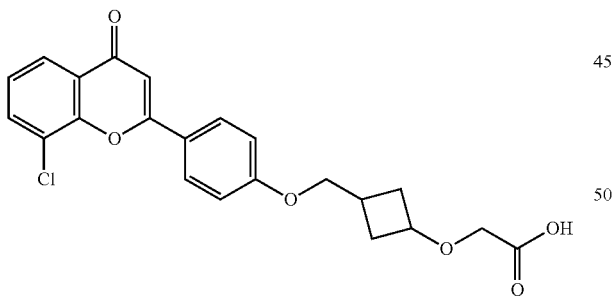

8

The solution of ethyl 2-[3-[[4-(8-chloro-4-oxo-chromen-2-yl)phenoxy]methyl]cyclobutoxy]acetate (0.1 g, 0.26 mmol, crude) in the mixed solvent of THF (10 mL) and H$_2$O (10 mL) was added LiOH·H$_2$O (259.55 mg, 10.84 mmol). The mixture was stirred at room temperature for 4 hours. After the reaction was completed, the mixture was adjusted to pH~5 by addition of 1N HCl. The resulting mixture was extracted by EtOAc (20 mL) three times. The combined organic layer was with brine, dried with anhydrous Na2SO4 and concentrated in vacuo. The residue was purified by preparative HPLC to give 2-[3-[[4-(8-chloro-4-oxo-chromen-2-yl)phenoxy]methyl]cyclobutoxy]acetic acid (45.0 mg, 41.7%) as a light yellow solid. $^1$H NMR (DMSO-d$_6$, 400 MHz): δ ppm 8.08 (d, J=8.9 Hz, 2H), 8.00 (d, J=7.9 Hz, 2H), 7.50 (t, J=7.8 Hz, 1H), 7.12-7.22 (m, 2H), 7.06 (s, 1H), 4.05-4.13 (m, 2H), 3.89-4.03 (m, 3H), 2.59-2.65 (m, 1H), 2.35-2.41 (m, 1H), 2.20-2.30 (m, 1H), 2.10-2.15 (m, 1H), 1.71-1.83 (m, 1H). MS obsd. (ESI$^+$) [(M+H)$^+$]:415.2.

Example 9

2-[2-[4-(8-chloro-4-oxo-chromen-2-yl)phenoxy]ethoxy]acetic acid

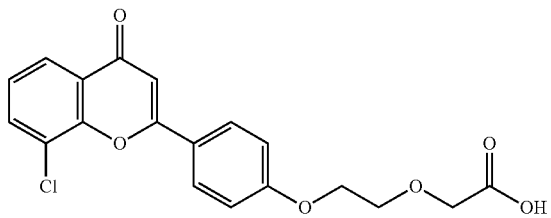

9

Step 1: Preparation of methyl 2-[2-[4-(8-chloro-4-oxo-chromen-2-yl)phenoxy]ethoxy]acetate

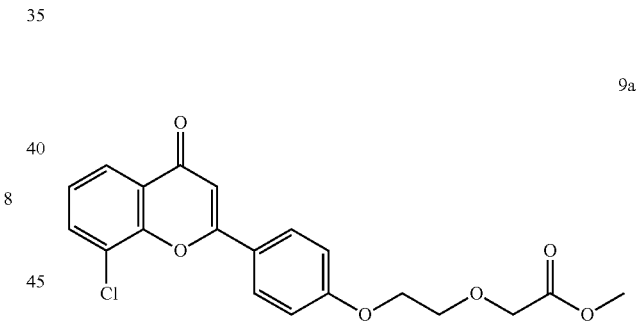

9a

To the solution of 8-chloro-2-[4-(2-hydroxyethoxy)phenyl]chromen-4-one (0.3 g, 0.1 mmol) in DMF (2.5 mL) was added NaH (0.1 g, 60% in oil) and the mixture was stirred at room temperature for 1 hour. Then to the resulting mixture was added methyl 2-chloroacetate (0.3 g, 2.84 mmol) and the mixture was stirred at room temperature for additional 3 hours. After the reaction was completed, the reaction was quenched with water (50 mL) and extracted with dichloromethane (40 mL) three times. The combined organic layer was washed with brine, dried over anhydrous Na$_2$SO$_4$ and concentrated in vacuo to give the crude methyl 2-[2-[4-(8-chloro-4-oxo-chromen-2-yl)phenoxy]ethoxy]acetate (0.38 g, 100%) as yellow solid, which was used in the next step without further purification. MS obsd. (ESI$^+$) [(M+H)$^+$]: 389.2.

Step 2: Preparation of 2-[2-[4-(8-chloro-4-oxo-chromen-2-yl)phenoxy]ethoxy]acetic acid

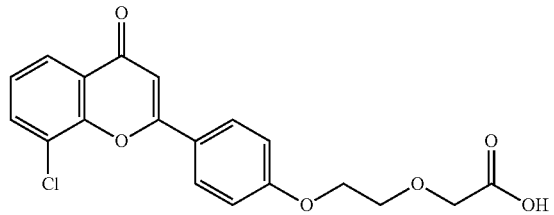

9

To a solution of methyl 2-[2-[4-(8-chloro-4-oxo-chromen-2-yl)phenoxy]ethoxy]acetate (0.38 g, 0.1 mmol, crude) in the mixed solvent of THF (2 mL) and water (2 mL) was added LiOH·H$_2$O (96 mg, 2.43 mmol). The mixture was stirred at room temperature for 4 hours. After the reaction was completed, the mixture was adjusted to pH~5 by addition of 1N HCl. The resulting mixture was extracted by EtOAc (20 mL) three times. The combined organic layer was washed with brine, dried with anhydrous Na$_2$SO$_4$ and concentrated in vacuo. The residue was purified by preparative HPLC to give 2-[2-[4-(8-chloro-4-oxo-chromen-2-yl)phenoxy]ethoxy]acetic acid (153 mg, 40.8%) as a yellow solid. $^1$H NMR (DMSO-d$_6$, 400 MHz): δ ppm 8.10-8.08 (d, J=8.0 Hz, 2H), 8.00-7.98 (d, J=8.0 Hz, 2H), 7.51-7.47 (t, J=7.8 Hz, 1H), 7.19-7.17 (d, J=8.0 Hz, 2H), 7.06 (s, 1H), 4.25-4.23 (m, 2H), 4.11 (s, 2H), 3.87-3.85 (m, 2H). MS obsd. (ESI$^+$) [(M+H)$^+$]:375.0.

Example 10

3-[2-[4-(8-chloro-4-oxo-chromen-2-yl)phenoxy]ethoxy]propanoic acid

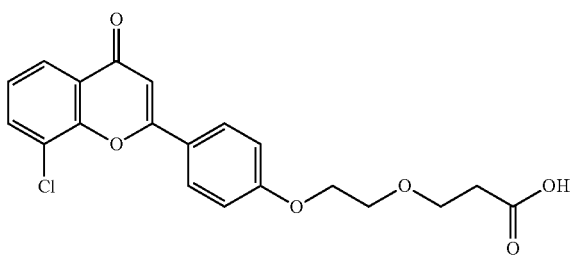

10

Example 10 was prepared in analogy to the procedure described for the preparation of example 9 by using ethyl 3-chloropropanoate as the starting material instead of methyl 2-chloroacetate in Step 1.

Example 10: $^1$H NMR (DMSO-d$_6$, 400 MHz): δ ppm 8.10-8.08 (d, J=9.0 Hz, 2H), 8.01-7.99 (d, J=8.0 Hz, 2H), 7.52-7.48 (t, J=7.8 Hz, 1H), 7.19-7.17 (d, J=8.0 Hz, 2H), 7.07 (s, 1H), 4.25 (s, 2H), 3.77 (s, 2H), 3.72-3.69 (m, 2H), 2.48-2.47 (d, J=4.0 Hz, 2H). MS obsd. (ESI$^+$) [(M+H)$^+$]: 389.0.

Example 11

3-[2-[4-(8-chloro-4-oxo-chromen-2-yl)phenoxy]ethoxy]-2,2-dimethyl-propanoic acid

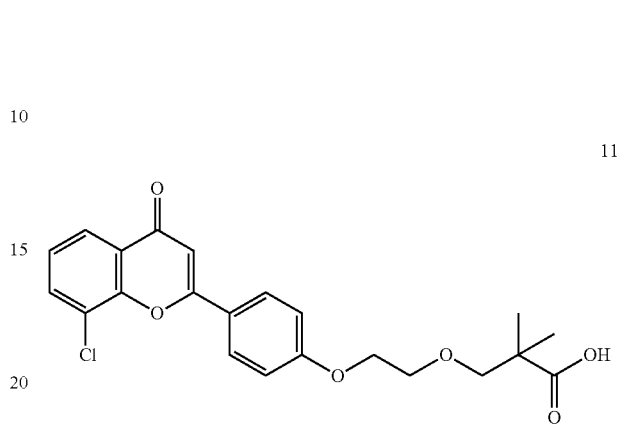

11

To a solution of 8-chloro-2-[4-(2-hydroxyethoxy)phenyl]chromen-4-one (100.0 mg, 0.32 mmol) and 3-chloro-2,2-dimethyl-propanoic acid (172.5 mg, 1.26 mmol) in DMF (2 mL) was added NaH (75.8 mg, 1.89 mmol) at room temperature and the mixture was stirred at 80° C. for 16 hours. Then the mixture was poured into water (20 mL) and adjusted to pH~4 by addition of conc. HCl. The resulting mixture was extracted with EtOAc (30 mL) three times. The combined organic layer was washed with brine, dried over Na$_2$SO$_4$ and concentrated in vacuo. The residue was then purified by preparative HPLC to give 3-[2-[4-(8-chloro-4-oxo-chromen-2-yl)phenoxy]ethoxy]-2,2-dimethyl-propanoic acid (5 mg, 3.7%) as a white solid. $^1$H NMR (DMSO-d$_6$, 400 MHz): δ ppm 8.08-8.05 (m, 3H), 7.91-7.89 (m, 1H), 7.48-7.44 (m, 1H), 7.16-7.14 (d, J=8.8 Hz, 2H), 6.89 (s, 1H), 4.50-4.48 (m, 2H), 4.36-4.34 (m, 2H), 3.59 (s, 2H), 1.19 (s, 6H). MS obsd. (ESI$^+$) [(M+H)$^+$]: 417.1.

Example 12

3-[2-[4-(8-chloro-4-oxo-chromen-2-yl)phenoxy]-1-methyl-ethoxy]cyclobutanecarboxylic acid

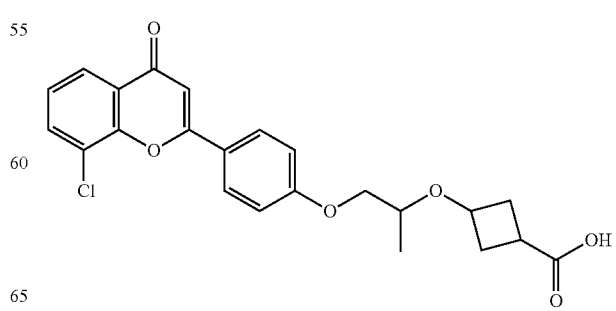

12

Step 1: Preparation of (2-chloro-1-methyl-ethoxy)-trimethyl-silane

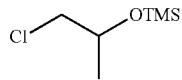

To a solution of 1-chloropropan-2-ol (6.0 g, 63.47 mmol) and TEA (13.27 mL, 95.2 mmol) in dichloromethane (50 mL) was added trimethylsilyl chloride (7.51 g, 69.81 mmol) at 0° C. and the mixture was then stirred at 0° C. for 4 hours. After the reaction was completed, the mixture was filtered and the filtrate was concentrated in vacuo. The residue was purified by column chromatography on silica gel (elution with PE:EtOAc=50:1 to 10:1) to give the (2-chloro-1-methyl-ethoxy)-trimethyl-silane (7.2 g, 68.0%) as colorless oil.

Step 2: Preparation of methyl 3-(2-chloro-1-methyl-ethoxy)cyclobutanecarboxylate

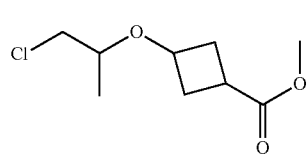

To a solution of (2-chloro-1-methyl-ethoxy)-trimethyl-silane (7.2 g, 43.2 mmol) and methyl 3-oxocyclobutanecarboxylate (5.8 g, 45.4 mmol) in dichloromethane (100 mL) was added trimethylsilyl trifluoromethanesulfonate (4.8 g, 21.6 mmol) at −78° C. After addition, the mixture was stirred at −78° C. for another 1 hour and then to the resulting mixture was added triethylsilane (14.25 g, 122.57 mmol). After addition, the resulting mixture was warmed to room temperature and stirred for 1 hour. After the reaction was completed, the mixture was washed with saturated NH$_4$Cl solution, brine, dried over anhydrous Na$_2$SO$_4$ and concentrated in vacuo. The residue was purified by column chromatography on silica gel (elution with PE/EtOAc=100:1-50:1) to give methyl 3-(2-chloro-1-methyl-ethoxy) cyclobutanecarboxylate (5.6 g, 62.7% yield). MS obsd. (ESI$^+$) [(M+H)$^+$]: 207.2.

Step 3: Preparation of 3-[2-[4-(8-chloro-4-oxo-chromen-2-yl)phenoxy]-1-methyl-ethoxy]cyclobutanecarboxylic acid

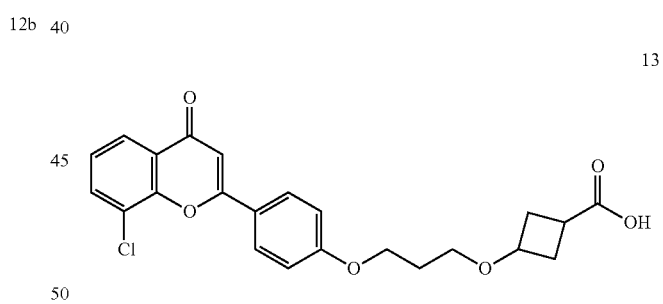

Example 12 was prepared in analogy to the procedure described for the preparation of Example 7 by using methyl 3-(2-chloro-1-methyl-ethoxy)cyclobutanecarboxylate as the starting material instead of methyl 4-[2-(p-tolylsulfonyloxy) ethoxy]cyclohexanecarboxylate in Step 3. $^1$H NMR (DMSO-d$_6$, 400 MHz): δ ppm 12.18 (br s, 1H), 8.12-8.06 (m, J=8.9 Hz, 2H), 8.00 (d, J=7.9 Hz, 2H), 7.50 (t, J=7.9 Hz, 1H), 7.21-7.14 (m, J=8.9 Hz, 2H), 7.07 (s, 1H), 4.07-3.97 (m, 3H), 3.87-3.74 (m, 1H), 2.94-2.82 (m, 0.5H), 2.58-2.55 (m, 0.5H), 2.48-2.38 (m, 2H), 2.22-2.07 (m, 1H), 1.99-1.94 (m, 1H), 1.19 (d, J=6.2 Hz, 3H). MS obsd. (ESI$^+$) [(M+H)$^+$]: 429.2.

Example 13

3-[3-[4-(8-chloro-4-oxo-chromen-2-yl)phenoxy] propoxy]cyclobutanecarboxylic acid

Step 1: Preparation of 8-chloro-2-[4-(3-hydroxypropoxy)phenyl]chromen-4-one

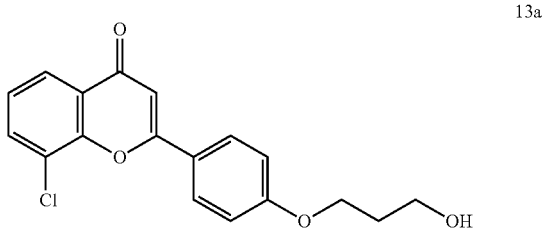 [SMILES: O=c1cc(-c2ccc(OCCCO)cc2)oc2c(Cl)cccc12]

To a solution of 8-chloro-2-(4-hydroxyphenyl)chromen-4-one (400.0 mg, 1.3 mmol) and K$_2$CO$_3$ (1.0 g, 7.2 mmol) in DMF (20 mL) was added 3-bromopropan-1-ol (500 mg, 1.3 mmol) at room temperature and the mixture was then stirred at 80° C. for 12 hours. After the reaction was completed, the mixture was diluted with water (30 mL) and extracted with EtOAc (50 mL) three times. The combined organic layer was washed with brine, dried over anhydrous Na$_2$SO$_4$ and concentrated in vacuo to give the crude 8-chloro-2-[4-(3-hydroxypropoxy)phenyl]chromen-4-one (400 mg, 93.1%) as a yellow solid, which was used in next step directly without further purification. MS obsd. (ESI$^+$) [(M+H)$^+$]: 330.1.

Step 2: Preparation of 3-[3-[4-(8-chloro-4-oxo-chromen-2-yl)phenoxy]propoxy]cyclobutanecarboxylic acid

13

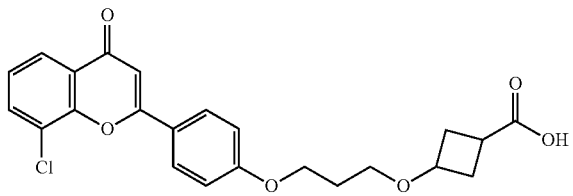

Example 13 was prepared in analogy to the procedure described for the preparation of Example 1 by using 8-chloro-2-[4-(3-hydroxypropoxy)phenyl]chromen-4-one as the starting material instead of 8-chloro-2-[4-(2-hydroxyethoxy)phenyl]chromen-4-one in Step 3.

Example 13: $^1$H NMR (DMSO-d$_6$, 400 MHz): δ ppm 8.08-8.06 (d, J=6.0 Hz, 2H), 8.00-7.97 (d, J=9.0 Hz, 2H), 7.51-7.46 (t, J=5.8 Hz, 1H), 7.17-7.14 (d, J=9.0 Hz, 2H), 7.04 (s, 1H), 4.15-4.11 (m, 2H), 3.88-3.83 (m, 1H), 3.54-3.50 (m, 2H), 2.59-2.56 (m, 1H), 2.78-2.65 (m, 2H), 2.03-1.98 (m, 4H). MS obsd. (ESI$^+$) [(M+H)$^+$]: 428.9.

Example 14

3-[3-[4-(8-chloro-4-oxo-chromen-2-yl)phenoxy]-2-hydroxy-propoxy]benzoic acid

14

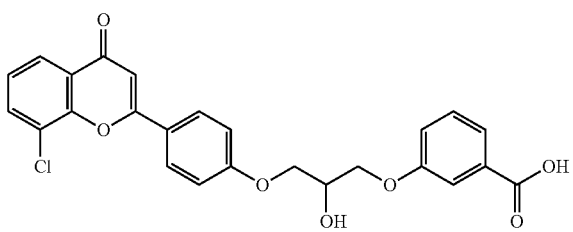

Step 1: Preparation of 8-chloro-2-[4-(oxiran-2-ylmethoxy)phenyl]chromen-4-one

14a

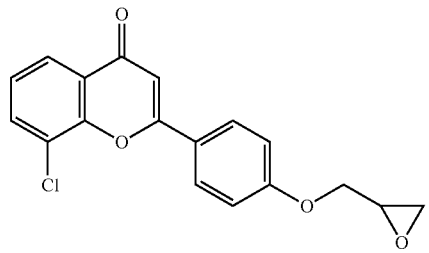

To a mixture of 8-chloro-2-(4-hydroxyphenyl)chromen-4-one (800 mg, 2.93 mmol) and 2-(chloromethyl)oxirane (814 mg, 8.8 mmol) in DMF (20 mL) was added K$_2$CO$_3$ (405 mg, 2.93 mmol) at room temperature and the mixture was then was stirred at room temperature overnight. After the reaction was completed, to the mixture was added water (100 mL), the resulting suspension was filtered. The solid was collected and further purified by recrystallization (MeOH, 20 mL) to give 8-chloro-2-[4-(oxiran-2-ylmethoxy)phenyl]chromen-4-one (650 mg, 67.4%) as a yellow solid. MS obsd. (ESI$^+$) [(M+H)$^+$]: 329.2.

Step 2: Preparation of methyl 3-[3-[4-(8-chloro-4-oxo-chromen-2-yl)phenoxy]-2-hydroxy-propoxy]benzoate 14b

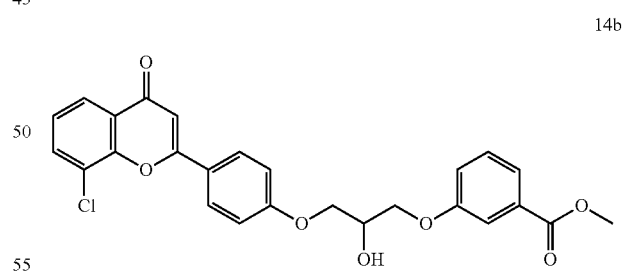

To a solution of 8-chloro-2-[4-(oxiran-2-ylmethoxy)phenyl]chromen-4-one (100 mg, 0.3 mmol), methyl 3-hydroxybenzoate (46.3 mg, 0.3 µmol) in THF (5 mL) was added NaH (40 mg, 60% in mineral oil, 1 µmol), the mixture was then stirred at room temperature overnight. After the reaction was completed, the mixture was concentrated in vacuo to give the crude methyl 3-[3-[4-(8-chloro-4-oxo-chromen-2-yl)phenoxy]-2-hydroxy-propoxy]benzoate (146 mg, 99.8%), which was used in the next step directly without further purification. MS obsd. (ESI$^+$) [(M+H)$^+$]: 481.3.

Step 3: Preparation of 3-[3-[4-(8-chloro-4-oxo-chromen-2-yl)phenoxy]-2-hydroxy-propoxy]benzoic acid

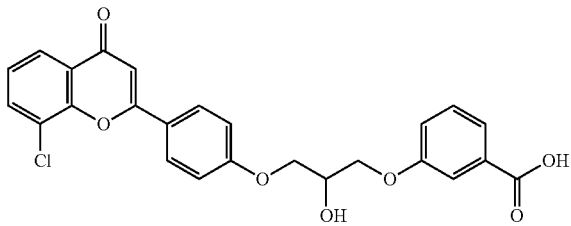

14

To a solution of methyl 3-[3-[4-(8-chloro-4-oxo-chromen-2-yl)phenoxy]-2-hydroxy-propoxy]benzoate (146 mg, 0.3 mmol, crude, prepared above) in the mixed solvent of MeOH (5 mL), THF (5 mL) and water (1 mL) was added LiOH (10 mg, 0.4 μmol). The mixture was then stirred at room temperature overnight. After the reaction was completed, to the mixture was added AcOH (60 mg, 1 mmol) and the resulting mixture was then concentrated in vacuo. The residue was then purified by preparative HPLC to give 3-[3-[4-(8-chloro-4-oxo-chromen-2-yl)phenoxy]-2-hydroxy-propoxy]benzoic acid (40 mg, 27.9%) as a white solid. $^1$H NMR (DMSO-d$_6$, 400 MHz): δ ppm 12.95-13.03 (m, 1H), 8.06-8.13 (m, 2H), 8.00 (d, J=8.07 Hz, 2H), 7.47-7.57 (m, 3H), 7.39-7.44 (m, 1H), 7.18-7.26 (m, 3H), 7.05-7.08 (m, 1H), 5.50 (d, J=4.89 Hz, 1H), 4.20-4.26 (m, 2H), 4.14-4.20 (m, 2H), 4.07-4.13 (m, 1H). MS obsd. (ESI$^+$) [(M+H)$^+$]: 467.2.

Example 15

3-[2-[4-(8-chloro-7-fluoro-4-oxo-chromen-2-yl)phenoxy]ethoxy]cyclobutanecarboxylic acid

15

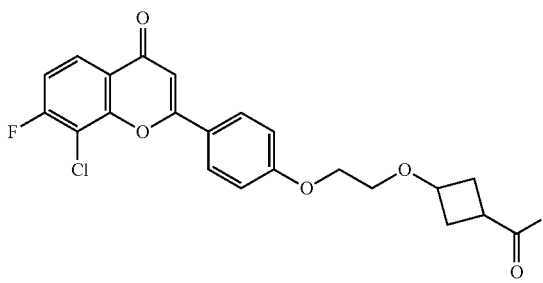

Step 1: Preparation of (2-chloro-3-fluoro-phenyl) acetate

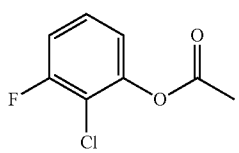

15a

To a mixture of 2-chloro-3-fluoro-phenol (10.0 g, 68.24 mmol) and TEA (7.6 g, 75.06 mmol) in dichloromethane (150 mL) was added acetyl chloride (5.36 g, 68.24 mmol) at 0° C. and the mixture was then stirred at room temperature for 16 hours. After the reaction was completed, the mixture was poured into water (30 mL) and extracted with dichloromethane (50 mL) three times. The combined organic layer was washed with brine, dried over anhydrous Na$_2$SO$_4$ and concentrated in vacuo. The residue was then purified by column chromatography on silica gel (elution with PE:EtOAc=50:1-20:1) to give (2-chloro-3-fluoro-phenyl) acetate (10.0 g, 75%) as colorless oil. MS obsd. (ESI$^+$) [(M+H)$^+$]: 189.2.

Step 2: Preparation of 1-(3-chloro-4-fluoro-2-hydroxy-phenyl)ethanone

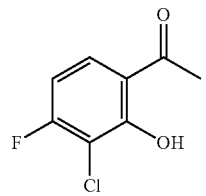

15b

A mixture of (2-chloro-3-fluoro-phenyl) acetate (10.0 g, 53.03 mmol) and AlCl$_3$ (7.07 g, 53.03 mmol) was stirred at 150° C. for 5 hours. After the reaction was completed, the mixture was poured into water (100 mL) and extracted with EtOAc (250 mL) twice. The combined organic layer was washed with brine, dried over anhydrous Na$_2$SO$_4$ and concentrated in vacuo. The residue was then purified by column chromatography on silica gel (elution with PE:EtOAc=50:1~20:1) to give 1-(3-chloro-4-fluoro-2-hydroxy-phenyl) ethanone (3.0 g, 30.0%) as a white solid. MS obsd. (ESI$^+$) [(M+H)$^+$]: 189.2.

Step 3: Preparation of (E)-1-(3-chloro-4-fluoro-2-hydroxy-phenyl)-3-(4-methoxyphenyl)prop-2-en-1-one

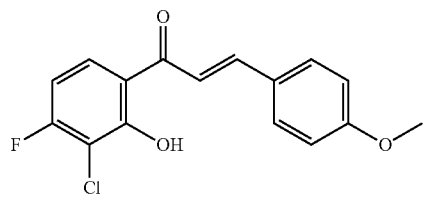

15c

To a solution of 1-(3-chloro-4-fluoro-2-hydroxy-phenyl) ethanone (2.0 g, 10.61 mmol) and 4-methoxybenzaldehyde (1.29 mL, 10.61 mmol) in EtOH (30 mL) was added KOH (1.79 g, 31.82 mmol) at room temperature and the mixture was then stirred at 100° C. for 3 hours. After the reaction was completed, the resulting mixture was adjusted to pH~4 by 2N HCl to yield a suspension. The solid was collected by filtration and dried in vacuo to give the crude (E)-1-(3-chloro-4-fluoro-2-hydroxy-phenyl)-3-(4-methoxyphenyl) prop-2-en-1-one (1.5 g, 46.1%) as a yellow solid, which was

Step 4: Preparation of 8-chloro-7-fluoro-2-(4-methoxyphenyl)chromen-4-one

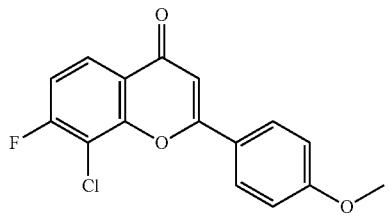

15d

To a solution of (E)-1-(3-chloro-4-fluoro-2-hydroxy-phenyl)-3-(4-methoxyphenyl)prop-2-en-1-one (1.5 g, 4.9 mmol) in DMSO (30 mL) was added I$_2$ (60 mg, 0.24 mmol) and then the mixture was stirred at 140° C. for 3 hours. After the reaction was completed, the reaction was cooled to room temperature, quenched with saturated NaHSO$_3$ solution (10 mL) and diluted with water 100 mL. The resulting suspension was filtered and the solid was collected and further purified by recrystallization (EtOH, 10 mL) to give 8-chloro-7-fluoro-2-(4-methoxyphenyl)chromen-4-one (1.2 g, 80.3%) as a yellow solid. MS obsd. (ESI$^+$) [(M+H)$^+$]: 304.9.

Step 4: Preparation of 8-chloro-7-fluoro-2-(4-hydroxyphenyl)chromen-4-one

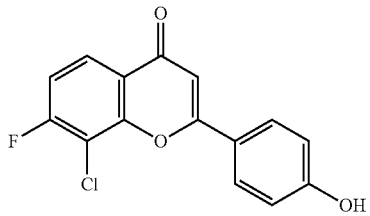

15e

To a solution of 8-chloro-7-fluoro-2-(4-methoxyphenyl)chromen-4-one (1.2 g, 39 mmol) in dichloromethane (20 mL) was added BBr$_3$ (2.96 g, 11.81 mmol) at room temperature and then stirred overnight. After the reaction was completed, the reaction was quenched by adding into saturated NaHCO$_3$ solution (250 mL) slowly. The resulting suspension was filtered, the solid was collected and dried in vacuo to give the crude 8-chloro-7-fluoro-2-(4-hydroxyphenyl)chromen-4-one (700 mg, 61.8%) as a yellow solid, which was used in the next step directly without further purification. (ESI$^+$) [(M+H)$^+$]: 290.9.

Step 5: Preparation of methyl 3-[2-[4-(8-chloro-7-fluoro-4-oxo-chromen-2-yl)phenoxy]ethoxy]cyclobutanecarboxylate

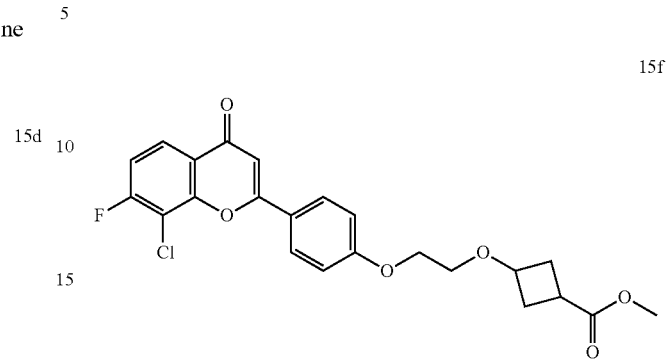

15f

To a solution of 8-chloro-7-fluoro-2-(4-hydroxyphenyl)chromen-4-one (350 mg, 1.2 mmol) and methyl 3-[2-(p-tolylsulfonyloxy)ethoxy]cyclobutanecarboxylate (435 mg, 1.3 mmol) in DMF (10 mL) was added K$_2$CO$_3$ (333 mg, 2.4 mmol) in DMF (20 mL) at room temperature. The mixture was then stirred at 80° C. for 4 hours. After the reaction was completed, to the mixture was added H$_2$O (50 mL) and the resulting mixture was extracted with EtOAc (30 mL) three times. The combined organic layer was washed with brine, dried over anhydrous Na$_2$SO$_4$ and concentrated in vacuo to give the crude methyl 3-[2-[4-(8-chloro-7-fluoro-4-oxo-chromen-2-yl)phenoxy]ethoxy]cyclobutanecarboxylate (200 mg, 37.2%) as a yellow solid, which was used in the next step directly without further purification. (ESI$^+$) [(M+H)$^+$]: 447.0.

Step 6: Preparation of 3-[2-[4-(8-chloro-7-fluoro-4-oxo-chromen-2-yl)phenoxy]ethoxy]cyclobutanecarboxylic acid

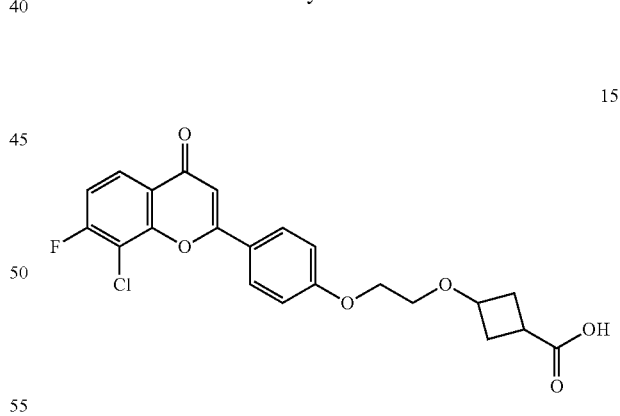

15

A mixture of methyl 3-[2-[4-(8-chloro-7-fluoro-4-oxo-chromen-2-yl)phenoxy]ethoxy]cyclobutanecarboxylate (200 mg, 0.45 mmol) in con. HCl (5 mL) was stirred at 100° C. for 4 hours. After the reaction was completed, the mixture was concentrated in vacuo. The residue was purified by preparative HPLC to give the 3-[2-[4-(8-chloro-7-fluoro-4-oxo-chromen-2-yl)phenoxy]ethoxy]cyclobutanecarboxylic acid (50 mg, 25.7%) as a yellow solid. $^1$H NMR (DMSO-d$_6$, 400 MHz): δ ppm 12.18 (s, 1H), 8.06-8.01 (m, 3H), 7.57-7.55 (m, 1H), 7.16-7.04 (m, 2H), 7.04 (s, 1H), 4.20-4.18 (d, J=4.0 Hz, 2H), 3.97-3.95 (m, 1H), 3.68-3.66 (m, 2H), 2.92-2.87 (m, 0.4H), 2.59-2.57 (m, 1H), 2.46-2.42 (m, 2H), 2.21-2.05 (m, 0.6H), 2.03-1.96 (m, 1H). MS obsd. (ESI⁺) [(M+H)⁺]: 433.0.

Example 19

3-[2-[4-(8-chloro-7-methoxy-4-oxo-chromen-2-yl)phenoxy]ethoxy]cyclobutanecarboxylic acid

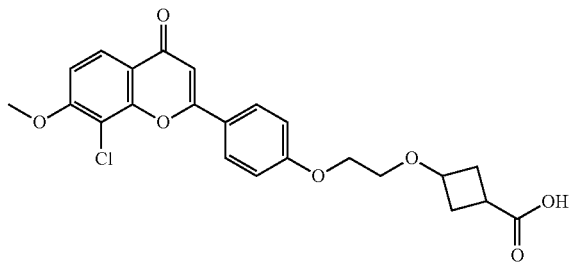

19

Step 1: Preparation of 1-(3-chloro-2,4-dihydroxy-phenyl)ethanone

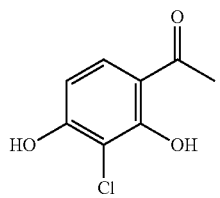

19a

To a mixture of 1-(2,4-dihydroxyphenyl)ethanone (10 g, 62.7 mmol) in H₂O (350 mL) was added NaOH (3.2 g, 78.9 mmol) at room temperature. Then to the resulting mixture was added NaClO (5.38 g, 72.3 mmol) slowly (over 1 hour) while keeping the inner temperature no more than 20° C. After addition, the mixture was stirred at room temperature for 17 hour. Then the mixture was adjusted to pH~3 by addition of 1N HCl solution. The resulting mixture was extracted with EtOAc (400 mL) three times. The combined organic layer was washed with saturated Na₂S₂O₃ (200 mL) solution twice, water (300 mL), brine (200 mL), dried over Na₂SO₄ and concentrated in vacuo. The residue was purified by column chromatography on silica gel (elution with PE:EtOAc=20:1-5:1) to give 1-(3-chloro-2,4-dihydroxy-phenyl)ethanone (3 g, 25.6%) as a solid. MS obsd. (ESI⁺) [(M+H)⁺]: 187.0.

Step 2: Preparation of 3-[2-[4-[(E)-3-(3-chloro-2,4-dihydroxy-phenyl)-3-oxo-prop-1-enyl]phenoxy]ethoxy]cyclobutanecarboxylic acid

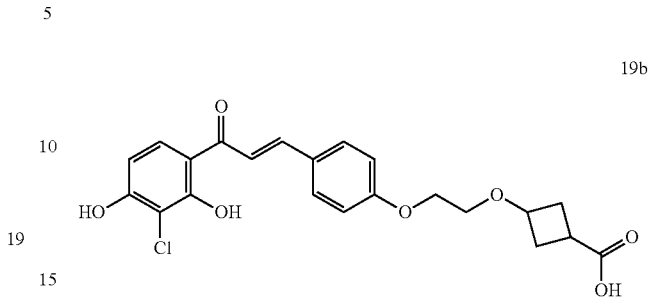

19b

To a solution of 1-(3-chloro-2,4-dihydroxy-phenyl)ethanone (630 mg, 3.4 mmol) and methyl 3-[2-(4-formylphenoxy)ethoxy]cyclobutanecarboxylate (int-3, 1.03 g, 3.71 mmol) in EtOH (10 mL) was added KOH (0.57 g, 10.1 mmol) at room temperature and the mixture was then stirred at 80° C. for 24 hours. After the reaction was completed, the mixture was poured into water (20 mL) and adjusted to pH~4 by 2N HCl, the resulting mixture was extracted with EtOAc (30 mL) three times. The combined organic layer was washed with brine, dried over Na₂SO₄ and concentrated in vacuo to give the crude 3-[2-[4-[(E)-3-(3-chloro-2,4-dihydroxy-phenyl)-3-oxo-prop-1-enyl]phenoxy]ethoxy]cyclobutanecarboxylic acid (200 mg, 13.5%) as a brown oil, which was used in the next step directly without further purification. MS obsd. (ESI⁺) [(M+H)⁺]: 433.1.

Step 3: Preparation of 3-[2-[4-(8-chloro-7-hydroxy-4-oxo-chromen-2-yl)phenoxy]ethoxy]cyclobutanecarboxylic acid

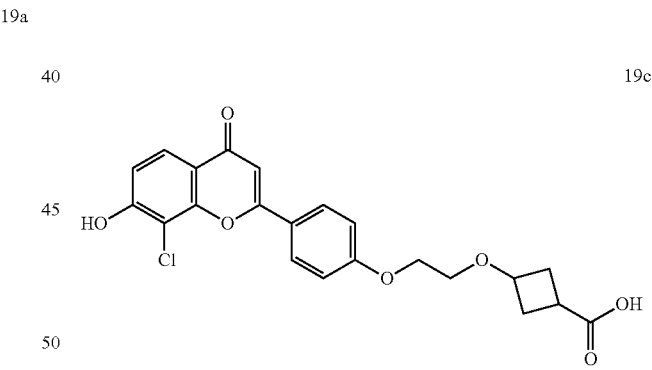

19c

To a solution of 3-[2-[4-[(E)-3-(3-chloro-2,4-dihydroxy-phenyl)-3-oxo-prop-1-enyl]phenoxy]ethoxy]cyclobutanecarboxylic acid (200 mg, 0.46 mmol, crude) in DMSO (3 mL) was added I₂ (6 mg, 0.02 mmol) at room temperature and then the mixture was stirred at 140° C. for 3 hours. After the reaction was completed, the reaction was cooled to room temperature, quenched with saturated NaHSO₃ solution (20 mL) and then extracted with EtOAc (20 mL) three times. The combined organic layer was washed with brine, dried over Na₂SO₄ and concentrated in vacuo to give the crude 3-[2-[4-(8-chloro-7-hydroxy-4-oxo-chromen-2-yl)phenoxy]ethoxy]cyclobutanecarboxylic acid as a brown solid. The crude was further purified by recrystallization (EtOAc, 5 mL) to give 3-[2-[4-(8-chloro-7-hydroxy-4-oxo-chromen-2-yl)phenoxy]ethoxy]cyclobutanecarboxylic acid (60 mg, 30.2%) as a grey solid. $^1$H NMR (DMSO-$d_6$, 400 MHz): δ ppm 8.07-8.05 (d, J=8.8, 2H), 7.85-7.83 (d, J=8.8, 1H), 7.18-7.16 (m, 2H), 7.12-7.10 (m, 1H), 6.93 (s, 1H), 4.20-4.18 (m, 2H), 3.99-3.91 (m, 1H), 3.68-3.66 (m, 2H), 2.63-2.59 (m, 1H), 2.42-2.41 (m, 2H), 2.03-1.96 (m, 2H). MS obsd. (ESI$^+$) [(M+H)$^+$]: 431.0.

Step 4: Preparation of methyl 3-[2-[4-(8-chloro-7-methoxy-4-oxo-chromen-2-yl)phenoxy]ethoxy]cyclobutanecarboxylate

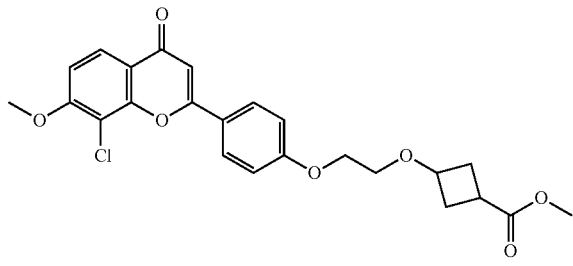

19d

To a mixture of 3-[2-[4-(8-chloro-7-hydroxy-4-oxo-chromen-2-yl)phenoxy]ethoxy]cyclobutanecarboxylic acid (50.0 mg, 0.120 mmol) and K$_2$CO$_3$ (48.12 mg, 0.350 mmol) in DMF (2 mL) was added MeI (41.18 mg, 0.290 mmol) at room temperature. The mixture was then stirred at room temperature for 16 hours. After the reaction was completed, the mixture was poured into water (5.0 mL) and the resulting suspension was filtered. The solid was collected and dried in vacuo to give the crude methyl 3-[2-[4-(8-chloro-7-methoxy-4-oxo-chromen-2-yl)phenoxy]ethoxy]cyclobutanecarboxylate (50.0 mg, 90.7%) as a yellow solid, which was used in the next step directly without further purification. MS obsd. (ESI$^+$) [(M+H)$^+$]: 459.1.

Step 5: Preparation of 3-[2-[4-(8-chloro-7-methoxy-4-oxo-chromen-2-yl)phenoxy]ethoxy]cyclobutanecarboxylic acid

19

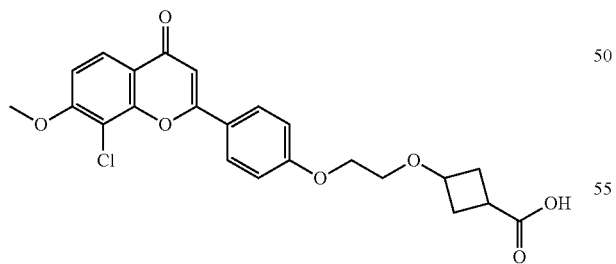

To a mixture of methyl 3-[2-[4-(8-chloro-7-methoxy-4-oxo-chromen-2-yl)phenoxy]ethoxy]cyclobutanecarboxylate (50.0 mg, 0.110 mmol) in the mixed solvent of THF (2 mL) and water (1 mL) was added LiOH·H$_2$O (13.72 mg, 0.330 mmol) at room temperature. Then the mixture was stirred at room temperature for 16 hours. After the reaction was completed, the mixture was poured into water (5.0 mL) and resulting suspension was filtered. The solid was collected and dried in vacuo to give 3-[2-[4-(8-chloro-7-methoxy-4-oxo-chromen-2-yl)phenoxy]ethoxy]cyclobutanecarboxylic acid (20 mg, 40.8%) as a yellow solid. $^1$H NMR (DMSO-$d_6$, 400 MHz): δ ppm 8.08-8.06 (d, J=8.8, 2H), 8.01-7.98 (d, J=8.8 Hz, 1H), 7.38-7.36 (d, J=8.8 Hz, 1H), 7.18-7.16 (d, J=8.8 Hz, 2H), 6.96 (s, 1H), 4.20-4.17 (m, 2H), 4.03 (s, 3H), 3.97-3.93 (m, 1H), 3.68-3.66 (m, 2H), 2.61-2.47 (m, 0.6H), 2.46-2.43 (m, 2H), 2.41-2.03 (m, 0.4H), 2.00-1.98 (m, 2H). MS obsd. (ESI$^+$) [(M+H)$^+$]: 445.1.

Example 20

3-[2-[4-(8-chloro-6-fluoro-4-oxo-chromen-2-yl)phenoxy]ethoxy]cyclobutanecarboxylic acid

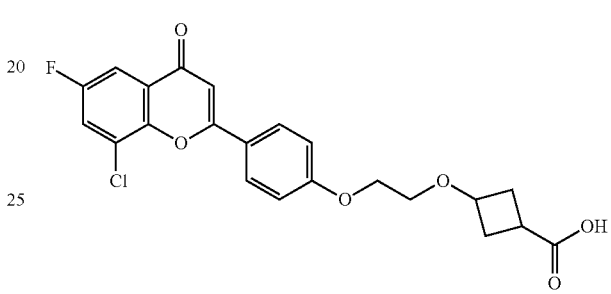

20

Step 1: Preparation of 1-(3-chloro-5-fluoro-2-hydroxy-phenyl)ethanone

20a

Compound 20a was prepared in analogy to the procedure described for the preparation of compound 15b by using 2-chloro-4-fluoro-phenol as the starting materials instead of 2-chloro-3-fluoro-phenol in Step 1.

Step 2: Preparation of 3-[2-[4-[(E)-3-(3-chloro-5-fluoro-2-hydroxy-phenyl)-3-oxo-prop-1-enyl]phenoxy]ethoxy]cyclobutanecarboxylic acid

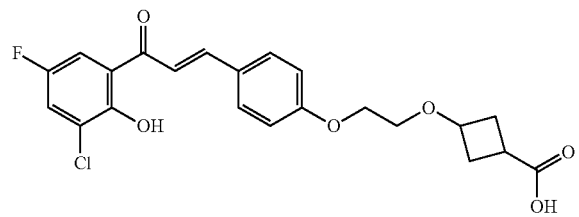

20b

Compound 20b was prepared in analogy to the procedure described for the preparation of compound 19b by using 1-(3-chloro-5-fluoro-2-hydroxy-phenyl)ethanone as the starting materials instead of 1-(3-chloro-2,4-dihydroxy-phenyl)ethanone in Step 2.

Step 3: Preparation of 3-[2-[4-(8-chloro-6-fluoro-4-oxo-chromen-2-yl)phenoxy]ethoxy]cyclobutanecarboxylic acid

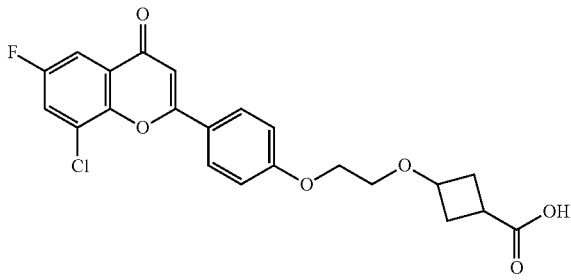

20

To a solution of 3-[2-[4-[(E)-3-(3-chloro-5-fluoro-2-hydroxy-phenyl)-3-oxo-prop-1-enyl]phenoxy]ethoxy]cyclobutanecarboxylic acid (100 mg, 0.23 mmol) in DMSO (2 mL) was added I$_2$ (3 mg, 0.01 mmol) at room temperature and then the mixture was stirred at 140° C. for 3 hours. After the reaction was completed, the reaction was cooled to room temperature, quenched with saturated NaHSO$_3$ solution (20 mL) and then extracted with EtOAc (20 mL) three times. The combined organic layer was washed with brine, dried over Na$_2$SO$_4$ and concentrated in vacuo. The residue was then purified by preparative HPLC to give 3-[2-[4-(8-chloro-6-fluoro-4-oxo-chromen-2-yl)phenoxy]ethoxy]cyclobutanecarboxylic acid (500 mg, 20.1%) as a yellow solid.

Example 20: $^1$H NMR (DMSO-d$_6$, 400 MHz): δ ppm 12.18 (s, 1H), 8.11-8.09 (m, 3H), 7.72-7.70 (m, 1H), 7.19-7.17 (m, 2H), 7.09-7.08 (m, 1H), 4.19-3.98 (m, 2H), 3.97-3.93 (m, 1H), 3.68-3.66 (m, 2H), 2.61-2.57 (m, 1H), 2.46-2.42 (m, 2H), 2.03-1.98 (m, 2H). MS obsd. (ESI$^+$) [(M+H)$^+$]: 433.1.

Example 21

3-[2-[4-(7,8-dichloro-4-oxo-chromen-2-yl)phenoxy]ethoxy]cyclobutanecarboxylic acid

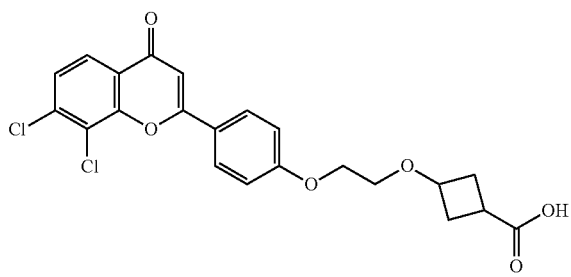

21

Example 21 was prepared in analogy to the procedure described for the preparation of Example 15 by using 2,3-dichlorophenol as the starting materials instead of 2-chloro-3-fluoro-phenol in Step 1.

Example 21: $^1$H NMR (DMSO-d$_6$, 400 MHz): δ ppm 12.17 (s, 1H), 8.08-8.00 (d, J=3.6 Hz, 2H), 7.99-7.97 (d, J=8.0 Hz, 1H), 7.75-7.73 (d, J=8.0 Hz, 1H), 7.19-7.17 (d, J=8.0 Hz, 2H), 7.1 (s, 1H), 4.21-4.19 (m, 2H), 3.68-3.66 (m, 3H), 2.59-2.50 (m, 1H), 2.46-2.45 (m, 2H), 2.43-2.40 (m, 1H), 2.01-1.98 (m, 1H). MS obsd. (ESI$^+$) [(M+H)$^+$]: 449.0.

Example 22

3-[2-[4-(8-chloro-6-cyano-4-oxo-chromen-2-yl)phenoxy]ethoxy]cyclobutanecarboxylic acid

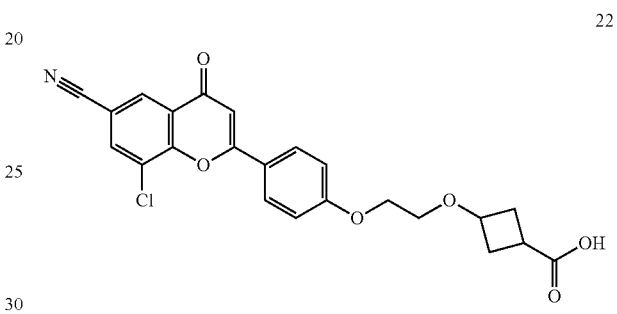

22

Step 1: Preparation of 1-(5-bromo-3-chloro-2-hydroxy-phenyl)ethanone

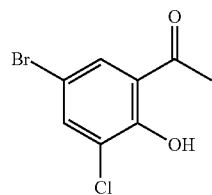

22a

Compound 22a was prepared in analogy to the procedure described for the preparation of compound 15b by using 4-bromo-2-chloro-phenol as the starting materials instead of 2-chloro-3-fluoro-phenol in Step 1.

Step 2: Preparation of 6-bromo-8-chloro-2-(4-methoxyphenyl)chromen-4-one

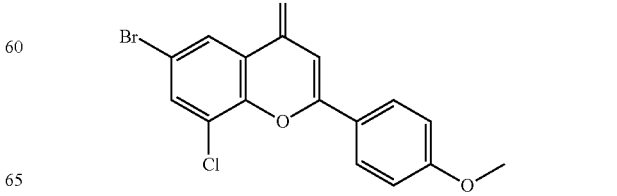

22b

Compound 22b was prepared in analogy to the procedure described for the preparation of compound 15d by using 1-(5-bromo-3-chloro-2-hydroxy-phenyl)ethanone as the starting materials instead of 1-(3-chloro-4-fluoro-2-hydroxy-phenyl)ethanone in Step 3.

Step 3: Preparation of 8-chloro-2-(4-methoxyphenyl)-4-oxo-chromene-6-carbonitrile

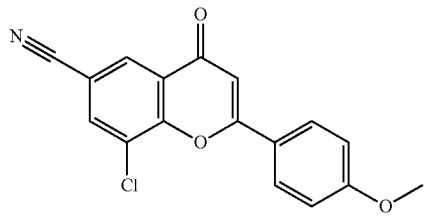

22c

To a solution of 6-bromo-8-chloro-2-(4-methoxyphenyl)chromen-4-one (1.4 g, 2.74 mmol) in DMF (20 mL) was added Zn(CN)$_2$ (643 mg, 5.47 mmol) and Pd(PPh$_3$)$_4$ (0.16 g, 0.140 mmol) under N$_2$ atmosphere at room temperature. The mixture was stirred at 150° C. for 4 hours. After the reaction was completed, the mixture was poured into water (100 mL) and the resulting suspension was filtered. The solid was collected and washed with EtOH (10 mL) to give the crude 8-chloro-2-(4-methoxyphenyl)-4-oxo-chromene-6-carbonitrile (1.2 g, 100%) as a solid, which was used in the next step directly without further purification. MS obsd. (ESI$^+$) [(M+H)$^+$]: 312.0.

Step 4: Preparation of 8-chloro-2-(4-hydroxyphenyl)-4-oxo-chromene-6-carbonitrile

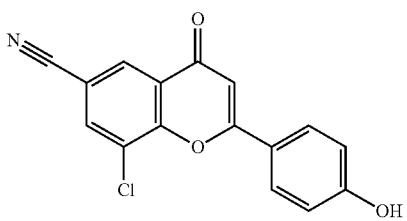

22d

To a solution of 8-chloro-2-(4-methoxyphenyl)-4-oxo-chromene-6-carbonitrile (1.2 g, 3.9 mmol) in dichloromethane (20 ml) was added BBr$_3$ (3.86 g, 15.4 mmol) at room temperature and the mixture was then stirred at room temperature overnight. After the reaction was completed, the reaction was quenched by adding into saturated NaHCO$_3$ solution (250 mL) slowly. The resulting suspension was filtered, the solid was collected and dried in vacuo to give the crude 8-chloro-2-(4-hydroxyphenyl)-4-oxo-chromene-6-carbonitrile (900 mg, 78.5%) as a yellow solid, which was used in the next step directly without further purification. (ESI$^+$) [(M+H)$^+$]: 297.9.

Step 5: Preparation of 3-[2-[4-(8-chloro-6-cyano-4-oxo-chromen-2-yl)phenoxy]ethoxy]cyclobutanecarboxylic acid

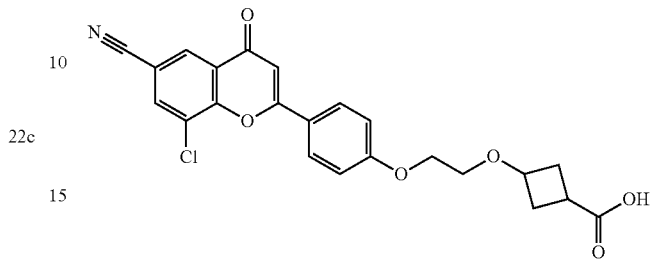

22

Example 22 was prepared in analogy to the procedure described for the preparation of Example 15 by using 8-chloro-2-(4-hydroxyphenyl)-4-oxo-chromene-6-carbonitrile as the starting materials instead of 8-chloro-7-fluoro-2-(4-hydroxyphenyl)chromen-4-one in Step 5. 100 mg of 3-[2-[4-(8-chloro-6-cyano-4-oxo-chromen-2-yl)phenoxy]ethoxy]cyclobutanecarboxylic acid was further purified by supercritical fluid chromatography (SFC) to give two diastereomers with cis- and trans-configuration, one of which is characterized as Example 22-A (45 mg) and the other is Example 22-B (45 mg).

Example 22: $^1$H NMR (DMSO-d$_6$, 400 MHz): δ ppm 12.19 (br s, 1H), 8.58 (d, J=2.0 Hz, 1H), 8.43-8.36 (m, 1H), 8.10 (d, J=8.9 Hz, 2H), 7.24-7.11 (m, 2H), 7.13-7.11 (m, 1H), 4.30-4.12 (m, 3H), 3.76-3.61 (m, 2H), 3.01-2.83 (m, 1H), 2.46-2.35 (m, 2H), 2.23-2.11 (m, 1H), 2.07-1.92 (m, 1H). MS obsd. (ESI$^+$) [(M+H)$^+$]: 440.2.

Example 22-A: $^1$H NMR (DMSO-d$_6$, 400 MHz): δ ppm 12.17 (br s, 1H), 8.58 (d, J=2.0 Hz, 1H), 8.39 (d, J=2.0 Hz, 1H), 8.10 (d, J=9.0 Hz, 2H), 7.23-7.13 (m, 3H), 4.26-4.12 (m, 3H), 3.74-3.64 (m, 2H), 2.99-2.87 (m, 1H), 2.40 (ddd, J=3.7, 6.9, 13.1 Hz, 2H), 2.23-2.10 (m, 2H). MS obsd. (ESI$^+$) [(M+H)$^+$]: 440.2.

Example 22-B: $^1$H NMR (DMSO-d$_6$, 400 MHz): δ ppm 12.30-11.80 (m, 1H), 8.61-8.55 (m, 1H), 8.43-8.35 (m, 1H), 8.16-8.05 (m, 2H), 7.25-7.13 (m, 3H), 4.20 (br s, 2H), 3.95 (q, J=7.3 Hz, 1H), 3.73-3.64 (m, 2H), 2.63-2.56 (m, 1H), 2.47-2.38 (m, 2H), 2.06-1.93 (m, 2H). MS obsd. (ESI$^+$) [(M+H)$^+$]: 440.2.

Example 23

3-[2-[4-(8-chloro-7-cyano-4-oxo-chromen-2-yl)phenoxy]ethoxy]cyclobutanecarboxylic acid

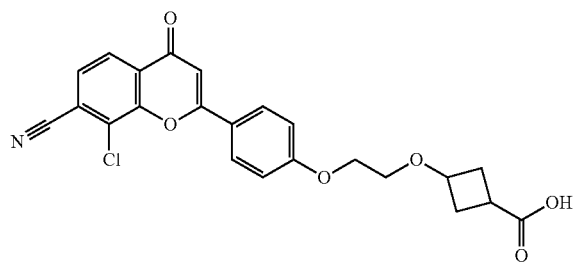

23

Step 1: Preparation of 1-(4-bromo-3-chloro-2-hydroxy-phenyl)ethanone

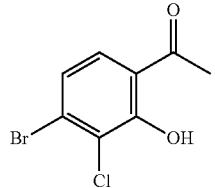
23a

Compound 23a was prepared in analogy to the procedure described for the preparation of compound 15b by using 4-bromo-2-chloro-phenol as the starting materials instead of 2-chloro-3-fluoro-phenol in Step 1.

Step 2: Preparation of 7-bromo-8-chloro-2-(4-methoxyphenyl)chromen-4-one

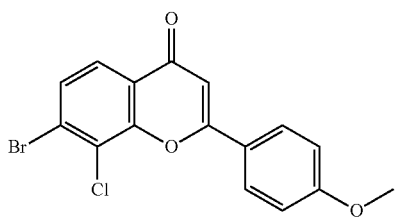
23b

Compound 23b was prepared in analogy to the procedure described for the preparation of compound 15d by using 1-(4-bromo-3-chloro-2-hydroxy-phenyl)ethanone as the starting materials instead of 1-(3-chloro-4-fluoro-2-hydroxy-phenyl)ethanone in Step 3.

Step 3: Preparation of 8-chloro-2-(4-methoxyphenyl)-4-oxo-chromene-7-carbonitrile

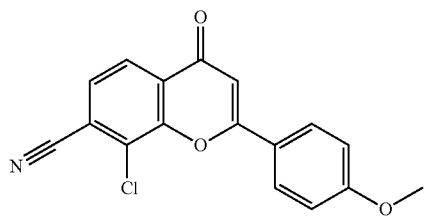
23c

To a solution of 7-bromo-8-chloro-2-(4-methoxyphenyl)chromen-4-one (1.4 g, 2.74 mmol) in DMF (20 mL) was added Zn(CN)$_2$ (643 mg, 5.47 mmol) and Pd(PPh$_3$)$_4$ (0.16 g, 0.140 mmol) under N$_2$ atmosphere at room temperature. The mixture was stirred at 150° C. for 4 hours. After the reaction was completed, the mixture was poured into water (100 mL) and the resulting suspension was filtered. The solid was collected and washed with EtOH (10 mL) to give the crude 8-chloro-2-(4-methoxyphenyl)-4-oxo-chromene-7-carbonitrile (1.2 g, 100%) as a solid, which was used in the next step directly without further purification. MS obsd. (ESI$^+$) [(M+H)$^+$]: 312.0.

Step 4: Preparation of 8-chloro-2-(4-hydroxyphenyl)-4-oxo-chromene-7-carbonitrile

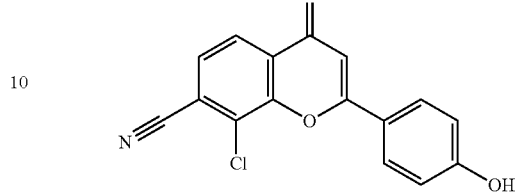
23d

To a solution of 8-chloro-2-(4-methoxyphenyl)-4-oxo-chromene-7-carbonitrile (1.2 g, 3.9 mmol) in dichloromethane (20 ml) was added BBr$_3$ (3.86 g, 15.4 mmol) at room temperature and the mixture was then stirred at room temperature overnight. After the reaction was completed, the reaction was quenched by adding into saturated NaHCO$_3$ solution (250 mL) slowly. The resulting suspension was filtered, the solid was collected and dried in vacuo to give the crude 8-chloro-2-(4-hydroxyphenyl)-4-oxo-chromene-7-carbonitrile (900 mg, 78.5%) as a yellow solid, which was used in the next step directly without further purification. (ESI$^+$) [(M+H)$^+$]: 297.9.

Step 5: Preparation of 3-[2-[4-(8-chloro-7-cyano-4-oxo-chromen-2-yl)phenoxy]ethoxy]cyclobutanecarboxylic acid

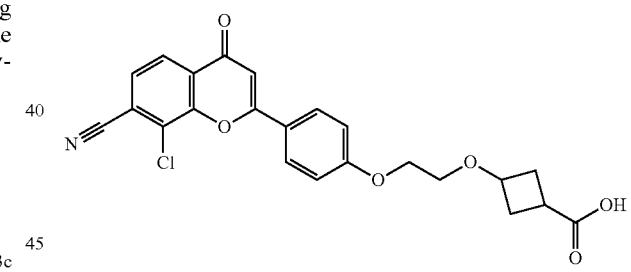
23

Example 23 was prepared in analogy to the procedure described for the preparation of Example 15 by using 8-chloro-2-(4-hydroxyphenyl)-4-oxo-chromene-7-carbonitrile as the starting materials instead of 8-chloro-7-fluoro-2-(4-hydroxyphenyl)chromen-4-one in Step 5. 45 mg of 3-[2-[4-(8-chloro-7-cyano-4-oxo-chromen-2-yl)phenoxy]ethoxy]cyclobutanecarboxylic acid was further purified by supercritical fluid chromatography (SFC) to give two diastereomers with cis- and trans-configuration, one of which is characterized as Example 23-A (31 mg) and the other is Example 23-B (11 mg).

Example 23: $^1$H NMR (DMSO-d$_6$, 400 MHz): δ ppm 12.19 (br s, 1H), 8.10 (dd, J=2.7, 8.1 Hz, 3H), 8.00 (d, J=8.2 Hz, 1H), 7.32-7.09 (m, 3H), 4.26-4.12 (m, 2H), 3.95 (q, J=7.3 Hz, 1H), 3.73-3.63 (m, 2H), 3.01-2.83 (m, 1H), 2.45-2.36 (m, 2H), 2.23-2.10 (m, 1H), 2.07-1.93 (m, 1H). MS obsd. (ESI$^+$) [(M+H)$^+$]: 440.0.

Example 23-A: $^1$H NMR (DMSO-d$_6$, 400 MHz): δ ppm 8.14-8.08 (m, 3H), 8.00 (d, J=8.2 Hz, 1H), 7.22-7.16 (m, 3H), 4.22-4.18 (m, 2H), 3.94 (s, 1H), 3.73-3.64 (m, 2H), 2.57 (br s, 1H), 2.44 (br d, J=9.2 Hz, 2H), 2.03-1.95 (m, 2H). MS obsd. (ESI⁺) [(M+H)⁺]: 440.0.

Example 23-B: ¹H NMR (DMSO-d₆, 400 MHz): δ ppm 8.17-8.07 (m, 3H), 8.00 (d, J=8.3 Hz, 1H), 7.24-7.15 (m, 3H), 4.27-4.12 (m, 3H), 3.72-3.64 (m, 2H), 3.00-2.86 (m, 1H), 2.39 (ddd, J=3.7, 6.9, 13.1 Hz, 2H), 2.23-2.11 (m, 2H). MS obsd. (ESI⁺) [(M+H)⁺]: 440.2.

Example 24

Cis-3-[2-[4-(8-chloro-5-hydroxy-4-oxo-chromen-2-yl)phenoxy]ethoxy]cyclobutanecarboxylic acid

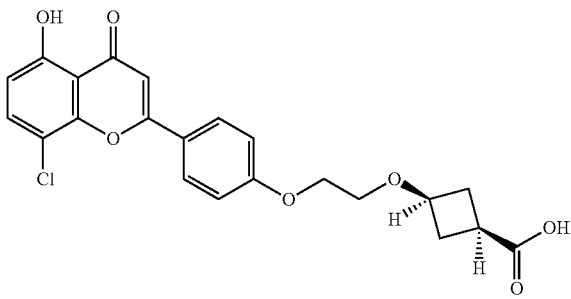

Step 1: Preparation of 1-(3-chloro-2,6-dihydroxy-phenyl)ethanone

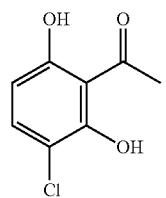

To a solution of 1-(2,6-dihydroxyphenyl)ethanone (5 g, 32.9 mmol) in AcOH (40 mL) was added NCS (4.83 g, 36.1 mmol) at room temperature and then the mixture was stirred at 50° C. for 2 hours. After the reaction was completed, the mixture was concentrated in vacuo and the residue was purified by column chromatography on silica gel (elution with PE:EtOAc=5:1) to give 1-(3-chloro-2,6-dihydroxy-phenyl)ethanone (200 mg 3.26% yield) as a white solid. MS obsd. (ESI⁺) [(M+H)⁺]: 187.1.

Step 2: Preparation of 1-[3-chloro-6-hydroxy-2-(2-methoxyethoxymethoxy)phenyl]ethanone

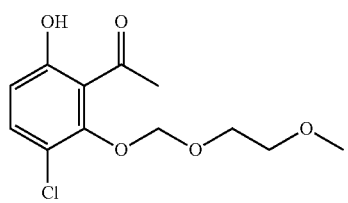

A mixture of 1-(3-chloro-2,6-dihydroxy-phenyl)ethanone (6 g, 32.2 mmol), 1-(chloromethoxy)-2-methoxyethane (4.81 g, 38.6 mmol) and K₂CO₃ (8.89 g, 3.88 ml, 64.3 mmol) in DMF (20 mL) was stirred at room temperature for 16 hours. After the reaction was completed, the mixture was diluted with water (50 mL) and the resulting mixture was extracted with dichloromethane (50 mL) three times. The combined organic layer was washed with brine, dried over Na₂SO₄ and concentrated in vacuo. The residue was purified by column chromatography on silica gel (elution with PE:EtOAc=10:1 to 3:1) to give 1-[3-chloro-6-hydroxy-2-(2-methoxyethoxymethoxy)phenyl]ethanone (8.0 g, 90.6%) as a colorless oil. MS obsd. (ESI⁺) [(M+H)⁺]: 275.1.

Step 3: Preparation of cis-3-[2-[4-[(E)-3-[3-chloro-6-hydroxy-2-(2-methoxyethoxymethoxy)phenyl]-3-oxo-prop-1-enyl]phenoxy]ethoxy]cyclobutanecarboxylic acid

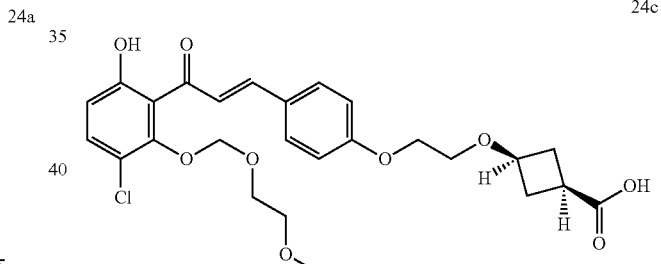

A mixture of 1-[3-chloro-6-hydroxy-2-(2-methoxyethoxymethoxy)phenyl]ethanone (1.3 g, 4.73 mmol), cis-ethyl 3-(2-(4-formylphenoxy)ethoxy)cyclobutanecarboxylate (int-4, 1.38 g, 4.73 mmol) and KOH (1.06 g, 18.9 mmol) in EtOH (40 mL) was stirred at room temperature for 16 hours. After the reaction was completed, the mixture was quenched with ice-water (60 mL) and adjusted to pH~6 by addition of 2N HCl. The resulting mixture was extracted with EtOAc (100 mL) three times. The combined organic layer was washed with brine, dried over anhydrous Na₂SO₄ and concentrated in vacuo to give the crude cis-3-[2-[4-[(E)-3-[3-chloro-6-hydroxy-2-(2-methoxyethoxymethoxy)phenyl]-3-oxo-prop-1-enyl]phenoxy]ethoxy]cyclobutanecarboxylic acid (2.6 g, 100%) as a yellow solid, which was used in the next step directly without further purification. MS obsd. (ESI⁺) [(M+H)⁺]: 521.1.

Step 4: Preparation of cis-3-[2-[4-(8-chloro-5-hydroxy-4-oxo-chromen-2-yl)phenoxy]ethoxy]cyclobutanecarboxylic acid

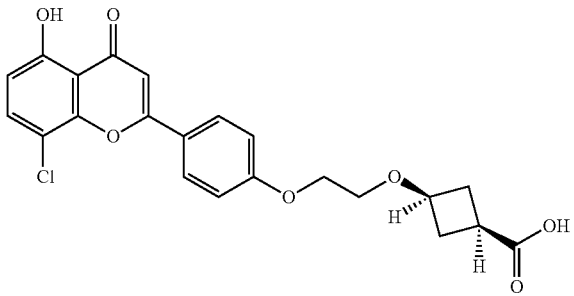

24

To a solution of cis-3-[2-[4-[(E)-3-[3-chloro-6-hydroxy-2-(2-methoxyethoxymethoxy)phenyl]-3-oxo-prop-1-enyl]phenoxy]ethoxy]cyclobutanecarboxylic acid (100 mg, 192 umol) in DMSO (60 mL) was added I$_2$ (5 mg, 19.2 μmol) and the mixture was stirred at 140° C. for 3 hours. After the reaction was completed, the reaction was cooled to room temperature, quenched with saturated NaHSO$_3$ solution (10 mL) and diluted with water 100 mL. The resulting suspension was filtered, the solid was collected and purified by preparative HPLC to afford cis-3-[2-[4-(8-chloro-5-hydroxy-4-oxo-chromen-2-yl)phenoxy]ethoxy]cyclobutanecarboxylic acid (20 mg, 24.2% yield) as a yellow solid. $^1$H NMR (DMSO-d$_6$, 400 MHz): δ ppm 12.88-12.62 (br s, 1H), 12.32-11.91 (br s, 1H), 8.10 (d, J=9.0 Hz, 2H), 7.81 (d, J=8.9 Hz, 1H), 7.22-7.10 (m, 3H), 6.84 (d, J=8.9 Hz, 1H), 4.25-4.13 (m, 2H), 3.95 (q, J=7.3 Hz, 1H), 3.70-3.64 (m, 2H), 2.64-2.56 (m, 1H), 2.47-2.37 (m, 2H), 2.06-1.95 (m, 2H). MS obsd. (ESI$^+$) [(M+H)$^+$]: 431.1.

Example 25

Cis-3-[2-[4-(8-chloro-5-methoxy-4-oxo-chromen-2-yl)phenoxy]ethoxy]cyclobutanecarboxylic acid

25

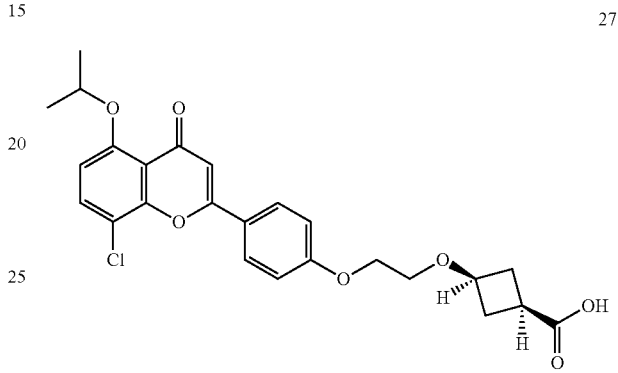

Example 25 was prepared in analogy to the procedure described for the preparation of Example 19 by using cis-3-[2-[4-(8-chloro-5-hydroxy-4-oxo-chromen-2-yl)phenoxy]ethoxy]cyclobutanecarboxylic acid as the starting materials instead of 3-[2-[4-(8-chloro-7-hydroxy-4-oxo-chromen-2-yl)phenoxy]ethoxy]cyclobutanecarboxylic acid (intermediate 19c) in Step 1.

Example 25: $^1$H NMR (DMSO-d$_6$, 400 MHz): δ ppm 12.73 (br s, 1H), 8.02 (d, J=8.93 Hz, 2H), 7.85 (d, J=9.05 Hz, 1H), 7.14 (d, J=8.93 Hz, 2H), 7.01 (d, J=9.05 Hz, 1H), 6.86 (s, 1H), 4.13-4.25 (m, 2H), 3.91-3.99 (m, 1H), 3.87 (s, 3H), 3.63-3.72 (m, 2H), 2.56-2.64 (m, 1H), 2.36-2.48 (m, 2H), 1.93-2.05 (m, 2H). MS obsd. (ESI$^+$) [(M+H)$^+$]: 445.2.

Example 27

Cis-3-[2-[4-(8-chloro-5-isopropoxy-4-oxo-chromen-2-yl)phenoxy]ethoxy]cyclobutanecarboxylic acid

27

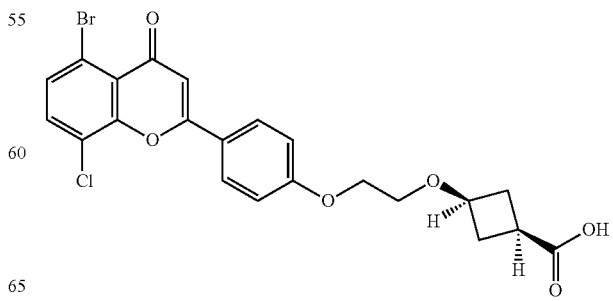

Example 27 was prepared in analogy to the procedure described for the preparation of Example 19 by using cis-3-[2-[4-(8-chloro-5-hydroxy-4-oxo-chromen-2-yl)phenoxy]ethoxy]cyclobutanecarboxylic acid and 2-iodopropane as the starting materials instead of 3-[2-[4-(8-chloro-7-hydroxy-4-oxo-chromen-2-yl)phenoxy]ethoxy]cyclobutanecarboxylic acid (intermediate 19c) and iodomethane in Step 1.

Example 27: $^1$H NMR (DMSO-d$_6$, 400 MHz): δ ppm 12.17 (br s, 1H), 8.03 (d, J=9.05 Hz, 2H), 7.81 (d, J=9.05 Hz, 1H), 7.15 (d, J=8.93 Hz, 2H), 7.02 (d, J=9.17 Hz, 1H), 6.82 (s, 1H), 4.61-4.74 (m, 1H), 4.12-4.23 (m, 2H), 3.93 (q, J=7.37 Hz, 1H), 3.63-3.69 (m, 2H), 2.53-2.61 (m, 1H), 2.36-2.47 (m, 2H), 1.93-2.04 (m, 2H), 1.32 (d, J=5.99 Hz, 6H). MS obsd. (ESI$^+$) [(M+H)$^+$]: 473.3.

Example 28

Cis-3-[2-[4-(5-bromo-8-chloro-4-oxo-chromen-2-yl)phenoxy]ethoxy]cyclobutanecarboxylic acid

28

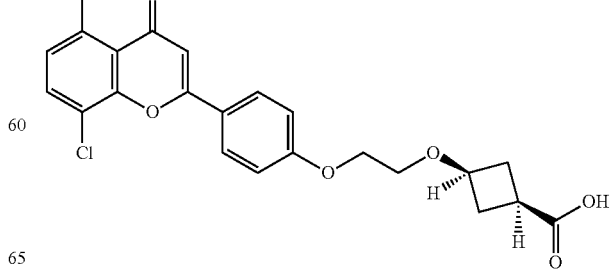

Step 1: Preparation of 1-(6-bromo-3-chloro-2-hydroxy-phenyl)ethanone

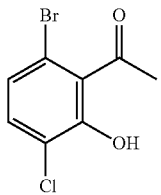

28a

Compound 28a was prepared in analogy to the procedure described for the preparation of compound 15b by using 5-bromo-2-chloro-phenol as the starting materials instead of 2-chloro-3-fluoro-phenol in Step 1.

Step 2: Preparation of cis-3-[2-[4-[(E)-3-(6-bromo-3-chloro-2-hydroxy-phenyl)-3-oxo-prop-1-enyl]phenoxy]ethoxy]cyclobutanecarboxylic acid

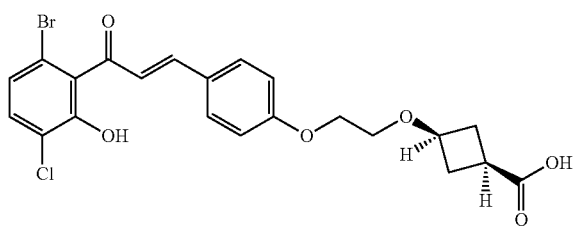

28b

A mixture of 1-(6-bromo-3-chloro-2-hydroxy-phenyl)ethanone (230 mg, 0.9 mmol), cis-ethyl 3-(2-(4-formylphenoxy)ethoxy)cyclobutanecarboxylate (268 mg, 0.9 mmol) and KOH (207 mg, 3.7 mmol) in EtOH (40 mL) was stirred at room temperature for 16 hours. After the reaction was completed, the mixture was quenched with ice-water (60 mL) and adjusted to pH~6 by addition of 2N HCl. The resulting mixture was extracted with EtOAc (100 mL) three times. The combined organic layer was washed with brine, dried over anhydrous $Na_2SO_4$ and concentrated in vacuo to give the crude cis-3-[2-[4-[(E)-3-(6-bromo-3-chloro-2-hydroxy-phenyl)-3-oxo-prop-1-enyl]phenoxy]ethoxy]cyclobutanecarboxylic acid (300 mg, 65.6%) as a yellow solid, which was used in the next step directly without further purification. MS obsd. (ESI$^+$) [(M+H)$^+$]: 495.2.

Step 3: Preparation of Cis-3-[2-[4-(5-bromo-8-chloro-4-oxo-chromen-2-yl)phenoxy]ethoxy]cyclobutanecarboxylic acid

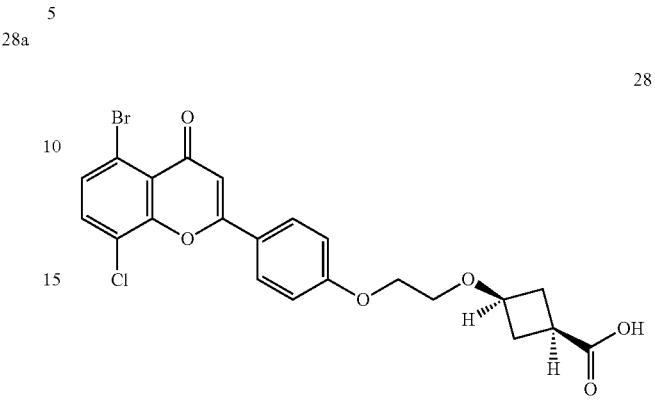

28

Example 28 was prepared in analogy to the procedure described for the preparation of Example 19 by using cis-3-[2-[4-[(E)-3-(6-bromo-3-chloro-2-hydroxy-phenyl)-3-oxo-prop-1-enyl]phenoxy]ethoxy]cyclobutanecarboxylic acid as the starting materials instead of 3-[2-[4-[(E)-3-(3-chloro-2,4-dihydroxy-phenyl)-3-oxo-prop-1-enyl]phenoxy]ethoxy]cyclobutanecarboxylic acid (intermediate 19b) in Step 3.

Example 28: $^1$H NMR (DMSO-$d_6$, 400 MHz): δ ppm 12.15 (s, 1H), 8.00-8.15 (m, 2H), 7.85 (d, J=8.56 Hz, 1H), 7.69 (d, J=8.56 Hz, 1H), 7.16 (d, J=9.05 Hz, 2H), 7.05 (s, 1H), 4.13-4.28 (m, 2H), 3.87-4.04 (m, 1H), 3.62-3.71 (m, 2H), 2.54-2.64 (m, 1H), 2.39-2.48 (m, 2H), 1.94-2.04 (m, 2H). MS obsd. (ESI$^+$) [(M+H)$^+$]:493.2.

Example 29

Cis-3-[2-[4-(5,8-dichloro-4-oxo-chromen-2-yl)phenoxy]ethoxy]cyclobutanecarboxylic acid

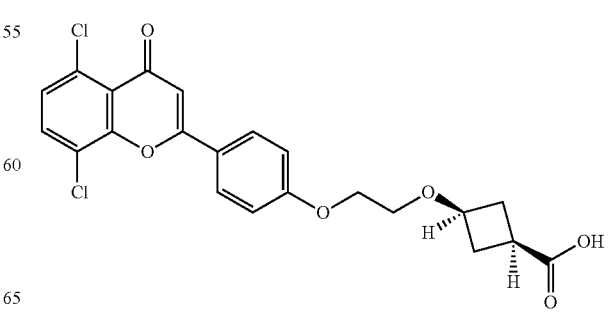

29

Step 1: Preparation of 1-(3,6-dichloro-2-hydroxy-phenyl)ethanone

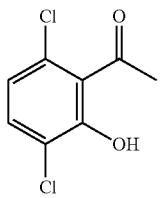

29a

Compound 29a was prepared in analogy to the procedure described for the preparation of compound 15b by using 2,5-dichlorophenol as the starting materials instead of 2-chloro-3-fluoro-phenol in Step 1.

Step 2: Preparation of Cis-3-[2-[4-(5,8-dichloro-4-oxo-chromen-2-yl)phenoxy]ethoxy]cyclobutanecarboxylic acid

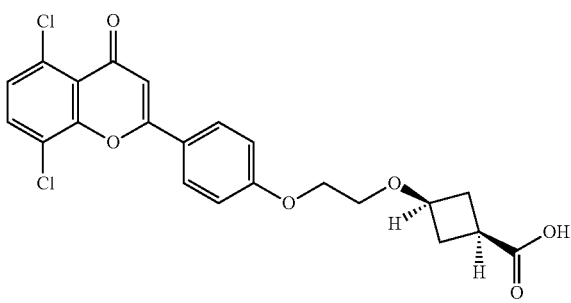

29

Example 29 was prepared in analogy to the procedure described for the preparation of Example 19 by using 1-(3,6-dichloro-2-hydroxy-phenyl)ethanone and cis-ethyl 3-(2-(4-formylphenoxy)ethoxy)cyclobutanecarboxylate as the starting materials instead of 1-(3-chloro-2,4-dihydroxy-phenyl)ethanone (intermediate 19a) and methyl 3-[2-(4-formylphenoxy)ethoxy]cyclobutanecarboxylate in Step 2.

Example 29: $^1$H NMR (DMSO-d$_6$, 400 MHz): δ ppm 12.17 (br s, 1H), 7.98-8.06 (m, 2H), 7.89 (d, J=8.56 Hz, 1H), 7.46 (d, J=8.56 Hz, 1H), 7.12 (d, J=9.05 Hz, 2H), 6.97 (s, 1H), 4.12-4.23 (m, 2H), 3.95 (q, J=7.34 Hz, 1H), 3.62-3.73 (m, 2H), 2.54-2.66 (m, 1H), 2.41-2.49 (m, 2H), 1.94-2.06 (m, 2H). MS obsd. (ESI$^+$) [(M+H)$^+$]:447.2.

Example 30

Cis-3-[2-[4-(8-chloro-5-cyclopropyl-4-oxo-chromen-2-yl)phenoxy]ethoxy]cyclobutanecarboxylic acid

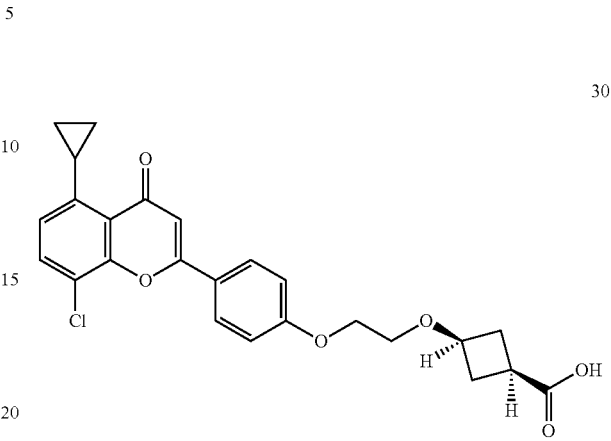

30

A mixture of cis-3-[2-[4-(5-bromo-8-chloro-4-oxo-chromen-2-yl)phenoxy]ethoxy]cyclobutanecarboxylic acid (50 mg, 101 μmol), cyclopropylboronic acid (26.1 mg, 304 μmol), K$_3$PO$_4$ (43 mg, 203 μmol) and Pd(dppf)Cl$_2$ (37 mg, 50.6 μmol) in DMF (5 mL) was heated at 100° C. under microwave radiation for 1 hour. After the reaction was completed, the mixture was concentrated in vacuo and the residue was purified by preparative HPLC to give cis-3-[2-[4-(8-chloro-5-cyclopropyl-4-oxo-chromen-2-yl)phenoxy]ethoxy]cyclobutanecarboxylic acid (14 mg, 30.4%) as a white solid. $^1$H NMR (DMSO-d$_6$, 400 MHz): δ ppm 12.17 (br s, 1H), 8.07 (d, J=8.93 Hz, 2H), 7.79 (d, J=8.44 Hz, 1H), 7.17 (d, J=9.05 Hz, 2H), 6.90-7.01 (m, 2H), 4.13-4.25 (m, 2H), 3.93 (q, J=7.37 Hz, 1H), 3.64-3.70 (m, 2H), 3.55-3.64 (m, 1H), 2.54-2.61 (m, 1H), 2.38-2.47 (m, 2H), 1.94-2.04 (m, 2H), 1.01-1.08 (m, 2H), 0.74-0.81 (m, 2H). MS obsd. (ESI$^+$) [(M+H)$^+$]:445.1.

Example 31

Cis-3-[2-[4-(8-chloro-5-methyl-4-oxo-chromen-2-yl)phenoxy]ethoxy]cyclobutanecarboxylic acid

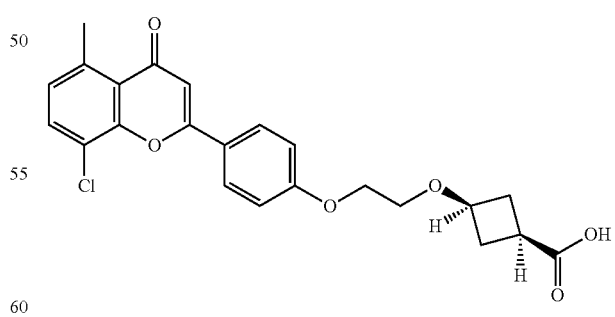

31

Example 31 was prepared in analogy to the procedure described for the preparation of Example 30 by using 2,4,6-trimethyl-1,3,5,2,4,6-trioxatriborinane as the starting materials instead of cyclopropylboronic acid.

Example 31: $^1$H NMR (DMSO-d$_6$, 400 MHz): δ ppm 8.05 (d, J=9.0 Hz, 2H), 7.81 (d, J=8.1 Hz, 1H), 7.22 (dd, J=0.7, 8.1 Hz, 1H), 7.15 (d, J=9.0 Hz, 2H), 6.95 (s, 1H), 4.21-4.15 (m, 2H), 3.95 (s, 1H), 3.69-3.64 (m, 2H), 2.74 (s, 3H), 2.58 (d, J=8.1 Hz, 1H), 2.48-2.39 (m, 2H), 2.04-1.94 (m, 2H). MS obsd. (ESI$^+$) [(M+H)$^+$]:429.2.

Example 33

Cis-3-[2-[4-(8-bromo-4-oxo-chromen-2-yl)phenoxy]ethoxy]cyclobutanecarboxylic acid

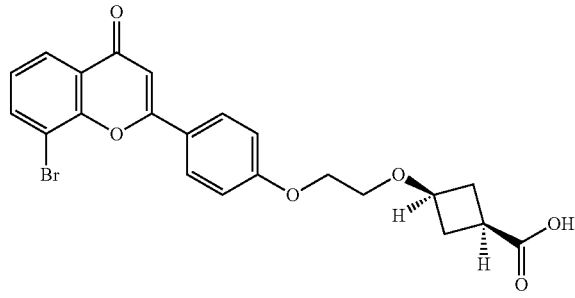 [SMILES: O=c1cc(-c2ccc(OCCO[C@H]3C[C@@H](C(=O)O)C3)cc2)oc2c(C3CC3)cccc12]

33

Example 33 was prepared in analogy to the procedure described for the preparation of Example 19 by using 1-(3-bromo-2-hydroxy-phenyl)ethanone and cis-ethyl 3-(2-(4-formylphenoxy)ethoxy)cyclobutanecarboxylate as the starting materials instead of 1-(3-chloro-2,4-dihydroxy-phenyl)ethanone (intermediate 19a) and methyl 3-[2-(4-formylphenoxy)ethoxy]cyclobutanecarboxylate in Step 2.

Example 33: $^1$H NMR (DMSO-d$_6$, 400 MHz): δ ppm 12.20 (br s, 1H), 8.07-8.18 (m, 3H), 8.03 (dd, J=1.53, 7.89 Hz, 1H), 7.43 (t, J=7.82 Hz, 1H), 7.14-7.21 (m, 2H), 7.03-7.10 (m, 1H), 4.16-4.25 (m, 2H), 3.89-4.01 (m, 1H), 3.62-3.71 (m, 2H), 2.55-2.64 (m, 1H), 2.40-2.48 (m, 2H), 1.94-2.05 (m, 2H). MS obsd. (ESI$^+$) [(M+H)$^+$]:459.3.

Example 34

Cis-3-[2-[4-(8-cyclopropyl-4-oxo-chromen-2-yl)phenoxy]ethoxy]cyclobutanecarboxylic acid

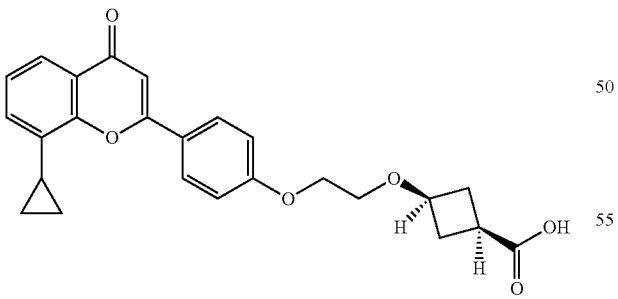

Example 34 was prepared in analogy to the procedure described for the preparation of Example 30 by using 3-[2-[4-(8-bromo-4-oxo-chromen-2-yl)phenoxy]ethoxy]cyclobutanecarboxylic acid as the starting materials instead of cis-3-[2-[4-(5-bromo-8-chloro-4-oxo-chromen-2-yl)phenoxy]ethoxy]cyclobutanecarboxylic acid.

Example 34: $^1$H NMR (DMSO-d$_6$, 400 MHz): δ ppm 11.52-13.15 (m, 1H), 8.10 (d, J=8.93 Hz, 2H), 7.84 (dd, J=1.83, 7.58 Hz, 1H), 7.33-7.45 (m, 2H), 7.15 (d, J=8.93 Hz, 2H), 6.98 (s, 1H), 4.13-4.25 (m, 2H), 3.94 (q, J=7.34 Hz, 1H), 3.60-3.73 (m, 2H), 2.52-2.64 (m, 2H), 2.40-2.48 (m, 2H), 1.93-2.06 (m, 2H), 1.07-1.26 (m, 2H), 0.74-0.96 (m, 2H). MS obsd. (ESI$^+$) [(M+H)$^+$]:421.2.

Example 35

Cis-3-[2-[4-(8-methyl-4-oxo-chromen-2-yl)phenoxy]ethoxy]cyclobutanecarboxylic acid

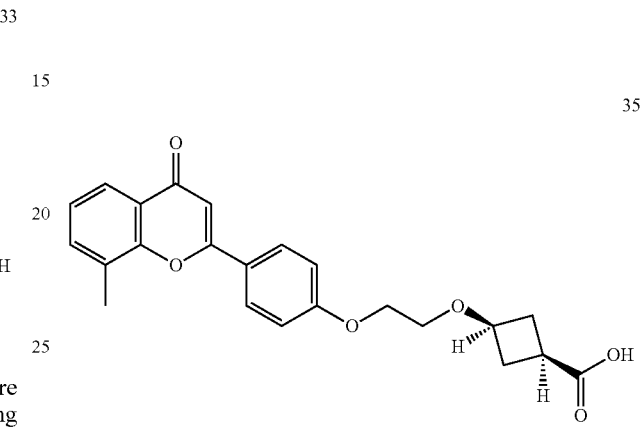

35

Example 35 was prepared in analogy to the procedure described for the preparation of Example 30 by using 3-[2-[4-(8-bromo-4-oxo-chromen-2-yl)phenoxy]ethoxy]cyclobutanecarboxylic acid and 2,4,6-trimethyl-1,3,5,2,4,6-trioxatriborinane as the starting materials instead of cis-3-[2-[4-(5-bromo-8-chloro-4-oxo-chromen-2-yl)phenoxy]ethoxy]cyclobutanecarboxylic acid and 2,4,6-trimethyl-1,3,5,2,4,6-trioxatriborinane.

Example 35: $^1$H NMR (DMSO-d$_6$, 400 MHz): δ ppm 12.16 (br s, 1H), 8.07 (d, J=8.93 Hz, 2H), 7.83-7.93 (m, 1H), 7.68 (d, J=7.21 Hz, 1H), 7.38 (t, J=7.58 Hz, 1H), 7.15 (d, J=9.05 Hz, 2H), 6.96 (s, 1H), 4.13-4.26 (m, 2H), 3.95 (q, J=7.37 Hz, 1H), 3.61-3.74 (m, 2H), 2.55-2.66 (m, 4H), 2.39-2.49 (m, 2H), 1.93-2.05 (m, 2H). MS obsd. (ESI$^+$) [(M+H)$^+$]:395.2.

Example 37

2-[2-[4-(8-chloro-5-fluoro-4-oxo-chromen-2-yl)phenoxy]ethoxy]acetic acid

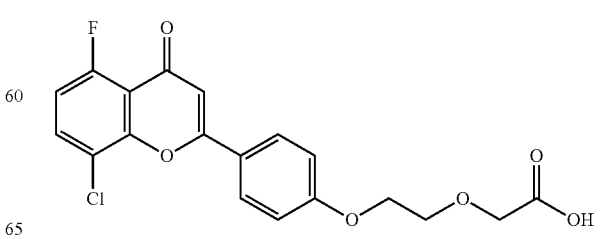

37

Step 1: Preparation of 1-(3-chloro-6-fluoro-2-hydroxy-phenyl)ethanone

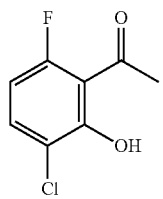

37a

Compound 37a was prepared in analogy to the procedure described for the preparation of compound 15b by using 2-chloro-5-fluoro-phenol as the starting materials instead of 2-chloro-3-fluoro-phenol in Step 1.

Step 2: Preparation of 8-chloro-5-fluoro-2-[4-(2-hydroxyethoxy)phenyl]chromen-4-one

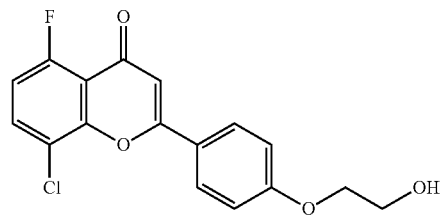

37b

Compound 37b was prepared in analogy to the procedure described for the preparation of compound 1a by using 1-(3-chloro-6-fluoro-2-hydroxy-phenyl)ethanone as the starting material instead of 1-(3-chloro-2-hydroxy-phenyl)ethanone in Step 1.

Step 3: Preparation of 2-[2-[4-(8-chloro-5-fluoro-4-oxo-chromen-2-yl)phenoxy]ethoxy]acetic acid

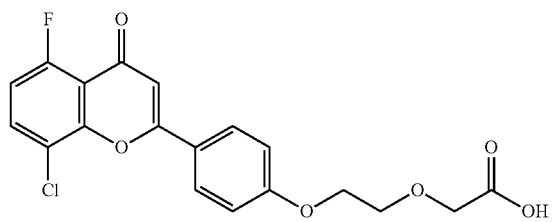

37

Example 37 was prepared in analogy to the procedure described for the preparation of Example 9 by using 8-chloro-5-fluoro-2-[4-(2-hydroxyethoxy)phenyl]chromen-4-one as the starting material instead of 8-chloro-2-[4-(2-hydroxyethoxy)phenyl]chromen-4-one in Step 1.

Example 37: $^1$H NMR (DMSO-$d_6$, 400 MHz): δ ppm 12.07-11.92 (m, 1H), 8.07 (d, J=9.0 Hz, 2H), 8.00 (dd, J=4.9, 8.8 Hz, 1H), 7.30 (dd, J=8.9, 10.6 Hz, 1H), 7.18 (d, J=9.0 Hz, 2H), 7.01 (s, 1H), 4.27-4.20 (m, 2H), 4.09 (s, 2H), 3.90-3.81 (m, 2H). MS obsd. (ESI$^+$) [(M+H)$^+$]: 393.1.

Example 38-A and Example 38-B

Cis-3-[2-[[5-(8-chloro-4-oxo-chromen-2-yl)-2-pyridyl]oxy]ethoxy]cyclobutanecarboxylic acid and trans-3-[2-[[5-(8-chloro-4-oxo-chromen-2-yl)-2-pyridyl]oxy]ethoxy]cyclobutanecarboxylic acid

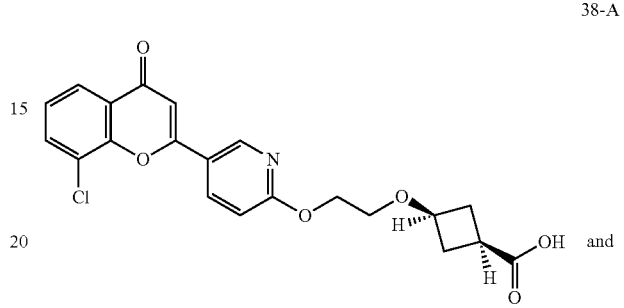

38-A and

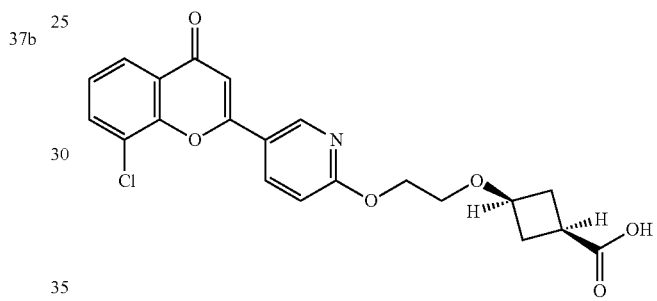

38-B

Step 1: Preparation of (2-acetyl-6-chloro-phenyl) 6-chloropyridine-3-carboxylate

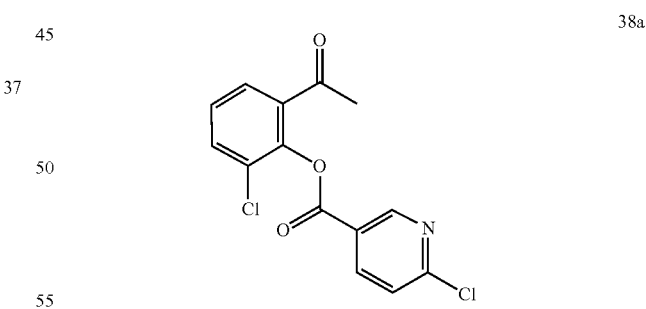

38a

To a solution of 1-(3-chloro-2-hydroxy-phenyl)ethanone (5 g, 29.3 mmol) and TEA (3.56 g, 4.91 ml, 35.2 mmol) in dichloromethane (20 mL) was added 6-chloropyridine-3-carbonyl chloride (5.42 g, 30.8 mmol). The reaction was stirred at room temperature for 14 hours. After the reaction was completed, the solution was concentrated in vacuo to give the crude (2-acetyl-6-chloro-phenyl) 6-chloropyridine-3-carboxylate (9.1 g, 100%) as a yellow oil, which was used in the next step directly without further purification. MS obsd. (ESI$^+$) [(M+H)$^+$]: 310.1.

Step 2: Preparation of 1-(3-chloro-2-hydroxy-phenyl)-3-(6-chloro-3-pyridyl)propane-1,3-dione

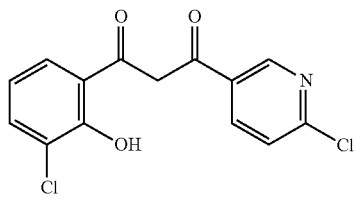

38b

To a solution of (2-acetyl-6-chloro-phenyl) 6-chloropyridine-3-carboxylate (9 g, 29 mmol) in THF (400 ml) was added potassium tert-butoxide (4.56 g, 40.6 mmol) at room temperature. Then mixture was stirred at room temperature for 2 hours. After the reaction was completed, the reaction was quenched with water (50 mL) and the aqueous was adjusted to pH~6 by addition of 0.5N HCl. The resulting mixture was then extracted with dichloromethane (100 mL) three times. The combined organic layer was washed with brine, dried over anhydrous Na$_2$SO$_4$ and concentrated in vacuo. The residue was then triturated in hexane (15 mL) and the mixture was then filtered. The solid was collected and dried in vacuo to give 1-(3-chloro-2-hydroxy-phenyl)-3-(6-chloro-3-pyridyl)propane-1,3-dione (9.0 g, 100%) as a light brown solid, which was used in the next step directly without further purification. MS obsd. (ESI$^+$) [(M+H)$^+$]: 310.1.

Step 3: Preparation of 8-chloro-2-(6-chloro-3-pyridyl)chromen-4-one

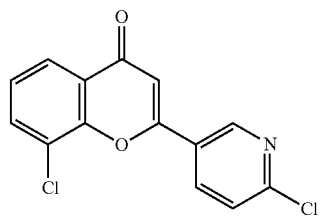

38c

To a mixture of 1-(3-chloro-2-hydroxy-phenyl)-3-(6-chloro-3-pyridyl)propane-1,3-dione (2.5 g, 8.06 mmol) in AcOH (15 mL) was added cat. con.H$_2$SO$_4$ (2 drop). The mixture was then stirred 130° C. for 4 hours. After the reaction was completed, the mixture was concentrated in vacuo to remove the solvent and the residue was suspended in water (20 mL). The suspension was then filtered, the solid was collected and dried in vacuo to give 8-chloro-2-(6-chloro-3-pyridyl)chromen-4-one (2.0 g, 84.9%) as a white solid, which was used in the next step directly without further purification. MS obsd. (ESI$^+$) [(M+H)$^+$]: 292.1.

Step 4: Preparation of cis-3-[2-[[5-(8-chloro-4-oxo-chromen-2-yl)-2-pyridyl]oxy]ethoxy]cyclobutanecarboxylic acid and trans-3-[2-[[5-(8-chloro-4-oxo-chromen-2-yl)-2-pyridyl]oxy]ethoxy]cyclobutanecarboxylic acid

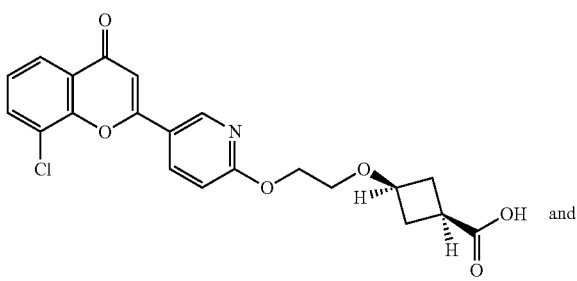

38-A and

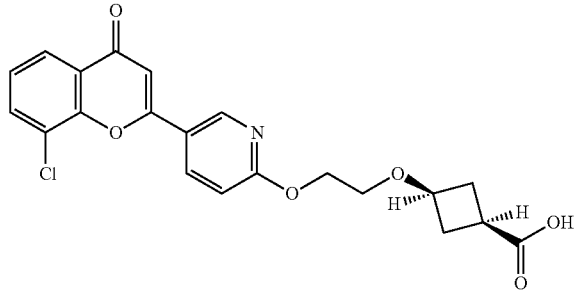

38-B

To a solution of methyl 3-(2-hydroxyethoxy)cyclobutanecarboxylate (1.91 g, 16 mmol) in DMF (20 mL) was added NaH (986 mg, 24.6 mmol) and the mixture was stirred at room temperature for 0.5 hour. Then the resulting mixture was added into the solution of 8-chloro-2-(6-chloro-3-pyridyl)chromen-4-one (1.6 g, 5.48 mmol) in DMF (20 mL). After addition, the mixture was stirred at 80° C. for 3 hours. After the reaction was completed, the mixture was filtered and the filtrate was purified by preparative HPLC to give 3-[2-[[5-(8-chloro-4-oxo-chromen-2-yl)-2-pyridyl]oxy]ethoxy]cyclobutanecarboxylic acid (320 mg, 14.0%) as a white solid. The solid was then further purified by supercritical fluid chromatography (SFC) to give two diastereomers with cis- and trans-configuration, one of which is characterized as Example 38-A (175 mg, 7.68%) and the other is Example 38-B (40 mg, 1.76%).

Example 38-A: $^1$H NMR (DMSO-d$_6$, 400 MHz): δ ppm 12.62 (s, 1H), 8.85-8.95 (m, 1H), 8.30-8.38 (m, 1H), 8.00-8.07 (m, 1H), 7.89-7.96 (m, 1H), 7.43-7.51 (m, 1H), 6.97-7.06 (m, 2H), 4.44-4.54 (m, 2H), 3.92-4.04 (m, 1H), 3.63-3.78 (m, 2H), 2.59-2.67 (m, 1H), 2.43-2.53 (m, 2H), 1.98-2.17 (m, 2H). MS obsd. (ESI$^+$) [(M+H)$^+$]: 416.1.

Example 38-B: $^1$H NMR (DMSO-d$_6$, 400 MHz): δ ppm 11.72-12.61 (m, 1H), 8.87-8.96 (m, 1H), 8.33-8.43 (m, 1H), 7.99 (dd, J=1.59, 7.83 Hz, 2H), 7.49 (s, 1H), 7.15 (s, 1H), 7.03-7.10 (m, 1H), 4.42-4.53 (m, 2H), 4.09-4.24 (m, 1H), 3.63-3.71 (m, 2H), 2.87-2.98 (m, 1H), 2.34-2.44 (m, 2H), 2.08-2.23 (m, 2H). MS obsd. (ESI$^+$) [(M+H)$^+$]: 416.1.

Example 39 and Example 40

Cis-3-[2-[5-(8-chloro-4-oxo-chromen-2-yl)pyrazin-2-yl]oxyethoxy]cyclobutanecarboxylic acid and Cis-methyl 3-[2-[5-(8-chloro-4-oxo-chromen-2-yl)pyrazin-2-yl]oxyethoxy]cyclobutanecarboxylate

39

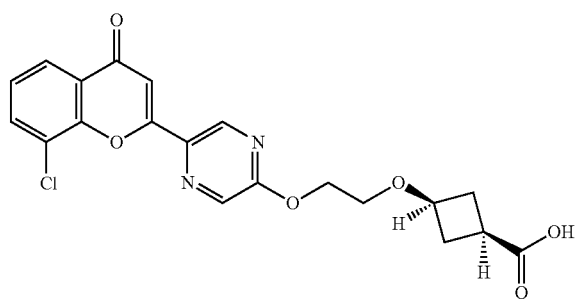

40

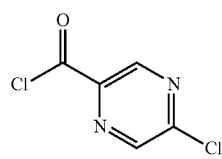

Step 1: Preparation of 5-chloropyrazine-2-carbonyl chloride

To a solution of 5-chloropyrazine-2-carboxylic acid (3 g, 18.9 mmol) in dichloromethane (60 mL) was added oxalyl dichloride (2.52 g, 1.7 mL, 19.9 mmol) dropwise at 0° C. Then to the mixture was added 2 drops of DMF and the mixture was stirred at room temperature for 2 hours. After the reaction was completed, the mixture was concentrated in vacuo to give 5-chloropyrazine-2-carbonyl chloride (3.4 g, 100%) as a white solid.

Step 2: Preparation of 8-chloro-2-(5-chloropyrazin-2-yl)chromen-4-one

39b

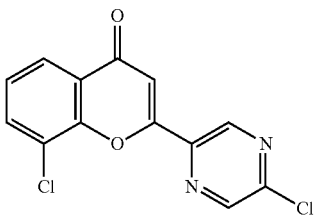

Compound 39b was prepared in analogy to the procedure described for the preparation of compound 38c by using 5-chloropyrazine-2-carbonyl chloride as the starting material instead of 6-chloropyridine-3-carbonyl chloride chloride in Step 1.

Step 3: Preparation of cis-3-[2-[5-(8-chloro-4-oxo-chromen-2-yl)pyrazin-2-yl]oxyethoxy]cyclobutanecarboxylic acid and cis-methyl 3-[2-[5-(8-chloro-4-oxo-chromen-2-yl)pyrazin-2-yl]oxyethoxy]cyclobutanecarboxylate

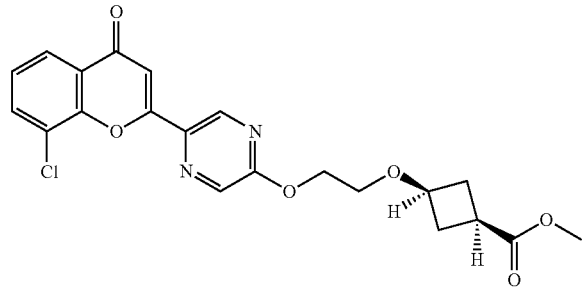

To a mixture of methyl 3-(2-hydroxyethoxy)cyclobutanecarboxylate (166 mg, 955 μmol) in DMF (5 mL) was added NaH (34.5 mg, 863 μmol) and the mixture was stirred at room temperature for 0.5 hour. Then to the resulting mixture was added the solution of 8-chloro-2-(5-chloropyrazin-2-yl)chromen-4-one (140 mg, 479 μmol) in DMF (5 mL). After addition, the mixture was stirred at room temperature for 12 hours. After the reaction was completed, the mixture was filtered and the filtrate was purified by preparative HPLC to give the cis configuration of 3-[2-[5-(8-chloro-4-oxo-chromen-2-yl)pyrazin-2-yl]oxyethoxy]cyclobutanecarboxylic acid (5 mg, 2.5%) and methyl 3-[2-[5-(8-chloro-4-oxo-chromen-2-yl)pyrazin-2-yl]oxyethoxy]cyclobutanecarboxylate (14 mg, 6.8%) as white foam. The trans isomer was not collected in the purification.

Example 39: $^1$H NMR (DMSO-$d_6$, 400 MHz): δ ppm 8.83-8.98 (m, 1H), 8.52-8.62 (m, 1H), 7.99-8.09 (m, 2H), 7.43-7.58 (m, 1H), 7.02-7.13 (m, 1H), 4.50-4.56 (m, 2H), 3.92-3.99 (m, 1H), 3.68-3.75 (m, 2H), 2.55-2.63 (m, 1H), 2.39-2.48 (m, 2H), 1.94-2.05 (m, 2H). MS obsd. (ESI$^+$) [(M+H)$^+$]: 417.1.

Example 40: $^1$H NMR (DMSO-$d_6$, 400 MHz): δ ppm 8.92 (d, J=1.22 Hz, 1H), 8.55-8.59 (m, 1H), 8.00-8.07 (m, 2H), 7.49-7.56 (m, 1H), 7.07-7.11 (m, 1H), 4.50-4.55 (m, 2H), 3.93-4.02 (m, 1H), 3.68-3.76 (m, 2H), 3.63 (s, 3H), 2.67-2.73 (m, 1H), 2.42-2.48 (m, 2H), 1.98-2.05 (m, 2H). MS obsd. (ESI$^+$) [(M+H)$^+$]: 431.1.

Example 41

Cis-methyl 3-[2-[6-(8-chloro-4-oxo-chromen-2-yl)pyridazin-3-yl]oxyethoxy]cyclobutanecarboxylate

41

Step 1: Preparation of 6-chloropyridazine-3-carbonyl chloride

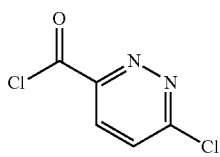

41a

To a solution of 6-chloropyridazine-3-carboxylic acid (4.4 g, 27.8 mmol) in dichloromethane (60 mL) was added oxalyl dichloride (3.7 g, 2.5 mL, 29.1 mmol) dropwise at 0° C. Then to the mixture was added 2 drops of DMF and the mixture was stirred at room temperature for 2 hours. After the reaction was completed, the mixture was concentrated in vacuo to give 5-chloropyrazine-2-carbonyl chloride (5.0 g, 100%) as a yellow solid.

Step 2: Preparation of 8-chloro-2-(6-chloropyridazin-3-yl)chromen-4-one

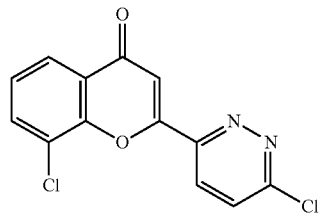

41b

Compound 41b was prepared in analogy to the procedure described for the preparation of compound 38c by using 6-chloropyridazine-3-carbonyl chloride as the starting material instead of 6-chloropyridine-3-carbonyl chloride chloride in Step 1.

Step 3: Preparation of cis-methyl 3-[2-[6-(8-chloro-4-oxo-chromen-2-yl)pyridazin-3-yl]oxyethoxy]cyclobutanecarboxylate

41

To a mixture of methyl 3-(2-hydroxyethoxy)cyclobutanecarboxylate (166 mg, 955 μmol) in DMF (5 mL) was added NaH (34.5 mg, 863 μmol) and the mixture was stirred at room temperature for 0.5 hour. Then to the resulting mixture was added the solution of 8-chloro-2-(6-chloropyridazin-3-yl)chromen-4-one (140 mg, 479 μmol) in DMF (5 mL). After addition, the mixture was stirred at room temperature for 12 hours. After the reaction was completed, the mixture was filtered and the filtrate was purified by preparative HPLC to give the cis configuration of methyl 3-[2-[5-(8-chloro-4-oxo-chromen-2-yl)pyrazin-2-yl]oxyethoxy]cyclobutanecarboxylate (60 mg, 29.2%) as white foam, the trans isomer was not collected in the purification.

Example 41: $^1$H NMR (DMSO-$d_6$, 400 MHz): δ ppm 8.27 (d, J=9.41 Hz, 1H), 8.02-8.08 (m, 2H), 7.51-7.61 (m, 2H), 7.32 (s, 1H), 4.63-4.69 (m, 2H), 3.94-4.02 (m, 1H), 3.71-3.77 (m, 2H), 3.60 (s, 3H), 2.65-2.74 (m, 1H), 2.41-2.48 (m, 2H), 1.94-2.09 (m, 2H). MS obsd. (ESI$^+$) [(M+H)$^+$]: 431.1.

Example 42

Cis-3-[2-[4-(8-chloro-4-oxo-chromen-2-yl)-2-fluoro-phenoxy]ethoxy]cyclobutanecarboxylic acid

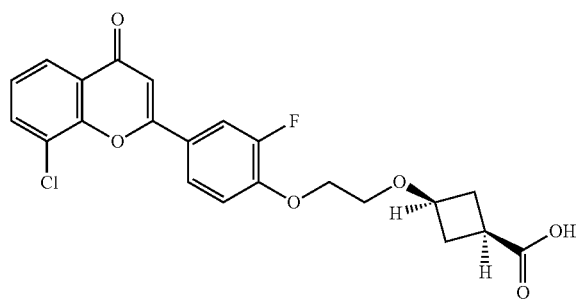

42

Step 1: Preparation of 8-chloro-2-(3-fluoro-4-methoxy-phenyl)chromen-4-one

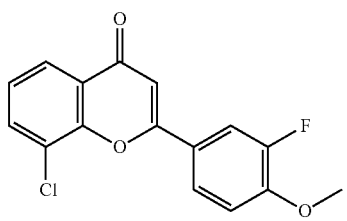

42a

Compound 42a was prepared in analogy to the procedure described for the preparation of compound 38c by using 3-fluoro-4-methoxy-benzoyl chloride as the starting material instead of 6-chloropyridine-3-carbonyl chloride chloride in Step 1.

Step 2: Preparation of 8-chloro-2-(3-fluoro-4-hydroxy-phenyl)chromen-4-one

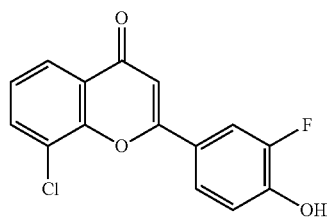

42b

To a solution of 8-chloro-2-(3-fluoro-4-methoxy-phenyl) chromen-4-one (850 mg, 2.7 mmol) in dichloromethane (20 mL) was added BBr₃ (1.0 M in dichloromethane, 13 mL, 13 mmol) at room temperature and the mixture was then stirred at room temperature overnight. After the reaction was completed, the reaction was quenched by adding into saturated NaHCO₃ solution (250 mL) slowly. The resulting suspension was filtered, the solid was collected and dried in vacuo to give the crude 8-chloro-2-(3-fluoro-4-hydroxy-phenyl) chromen-4-one (250 mg) as a yellow solid, which was used in the next step directly without further purification. (ESI⁺) [(M+H)⁺]: 291.1.

Step 3: Preparation of cis-3-[2-[4-(8-chloro-4-oxo-chromen-2-yl)-2-fluoro-phenoxy]ethoxy]cyclobutanecarboxylic acid

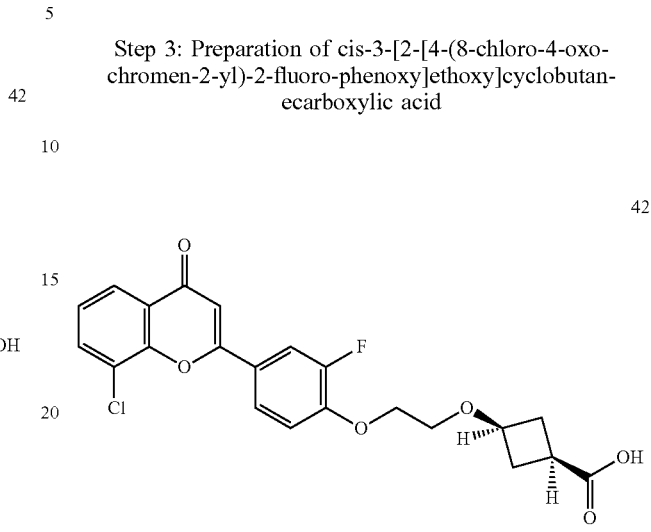

42

To a mixture of 8-chloro-2-(3-fluoro-4-hydroxy-phenyl) chromen-4-one (180 mg, 619 μmol) and methyl 3-(2-(tosyloxy)ethoxy)cyclobutanecarboxylate (224 mg, 681 μmol,) in DMF (5 mL) was added K₂CO₃ (171 mg, 1.24 mmol) and the mixture was then stirred at 50° C. overnight. Then to the resulting mixture was added MeOH (5 mL), water (1 mL) and LiOH (44.5 mg, 1.86 mmol). After the addition, the mixture was stirred at room temperature for 4 hours. The mixture was then filtered and the filtrate was purified by preparative HPLC to give the cis configuration of 3-[2-[4-(8-chloro-4-oxo-chromen-2-yl)-2-fluoro-phenoxy]ethoxy] cyclobutanecarboxylic acid (15 mg, 5.6%) as a white foam, the trans isomer was not collected in the purification. ¹H NMR (DMSO-d₆, 400 MHz): δ ppm 7.90-8.04 (m, 3H), 7.34-7.55 (m, 3H), 7.14 (s, 1H), 4.23-4.32 (m, 2H), 3.90-4.02 (m, 1H), 3.64-3.75 (m, 2H), 2.55-2.65 (m, 1H), 2.39-2.47 (m, 2H), 1.92-2.06 (m, 2H). MS obsd. (ESI⁺) [(M+H)⁺]: 433.1.

Example 43

Cis-3-[2-[2-chloro-4-(8-chloro-4-oxo-chromen-2-yl) phenoxy]ethoxy]cyclobutanecarboxylic acid

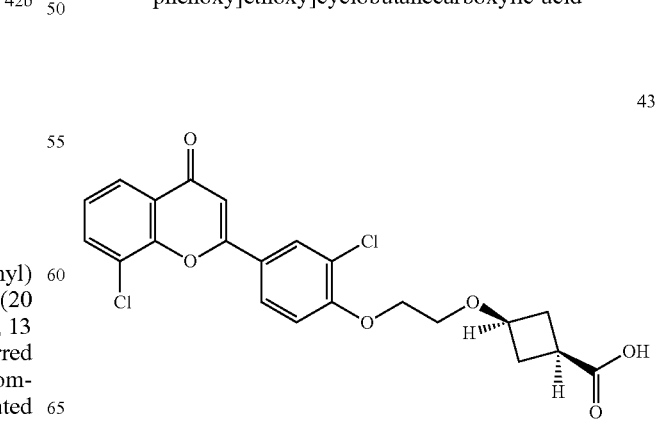

43

Step 1: Preparation of 8-chloro-2-(3-chloro-4-methoxy-phenyl)chromen-4-one

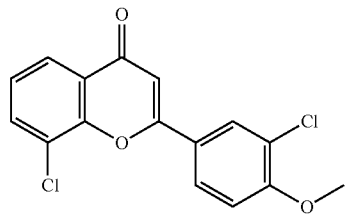

43a

Compound 43a was prepared in analogy to the procedure described for the preparation of compound 38c by using 3-chloro-4-methoxy-benzoyl chloride as the starting material instead of 6-chloropyridine-3-carbonyl chloride chloride in Step 1.

Step 2: Preparation of cis-3-[2-[2-chloro-4-(8-chloro-4-oxo-chromen-2-yl)phenoxy]ethoxy]cyclobutanecarboxylic acid

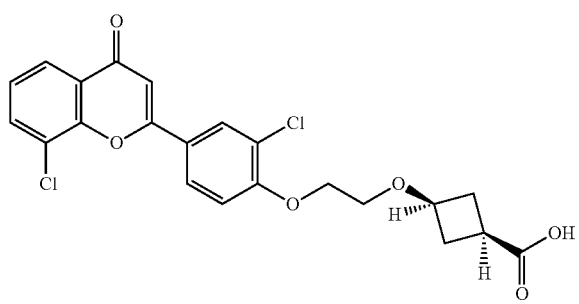

43

Example 43 was prepared in analogy to the procedure described for the preparation of Example 42 by using 8-chloro-2-(3-chloro-4-methoxy-phenyl)chromen-4-one as the starting material instead of 8-chloro-2-(3-fluoro-4-methoxy-phenyl)chromen-4-one in Step 2.

Example 43: $^1$H NMR (DMSO-$d_6$, 400 MHz): δ ppm 12.02-12.44 (m, 1H), 8.15-8.21 (m, 1H), 8.05-8.10 (m, 1H), 7.96-8.02 (m, 2H), 7.45-7.54 (m, 1H), 7.34-7.40 (m, 1H), 7.14-7.21 (m, 1H), 4.26-4.31 (m, 2H), 3.92-4.07 (m, 1H), 3.67-3.77 (m, 2H), 2.55-2.63 (m, 1H), 2.39-2.47 (m, 2H), 1.96-2.06 (m, 2H). MS obsd. (ESI$^+$) [(M+H)$^+$]: 449.1.

Example 44

Cis-3-[2-[2-bromo-4-(8-chloro-4-oxo-chromen-2-yl)phenoxy]ethoxy]cyclobutanecarboxylic acid

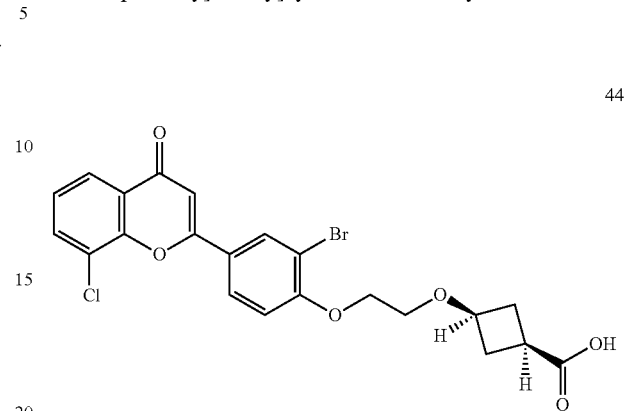

44

Step 1: Preparation of 2-(3-bromo-4-hydroxy-phenyl)-8-chloro-chromen-4-one

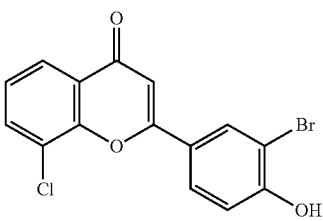

44a

Compound 44a was prepared in analogy to the procedure described for the preparation of compound 3c by using 3-bromo-4-methoxy-benzaldehyde as the starting material instead of 4-methoxybenzaldehyde in Step 1.

Step 2: Preparation of methyl 3-[2-[2-bromo-4-(8-chloro-4-oxo-chromen-2-yl)phenoxy]ethoxy]cyclobutanecarboxylate

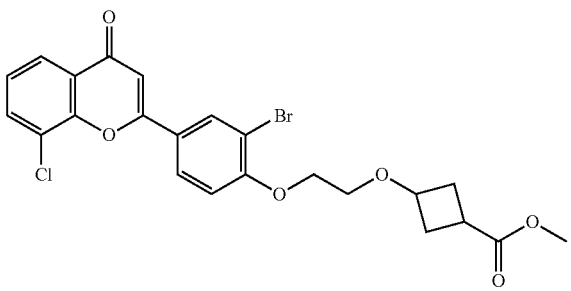

44b

To a solution of 2-(3-bromo-4-hydroxy-phenyl)-8-chloro-chromen-4-one (250 mg, 711 μmol), methyl 3-(2-(4-(tosyloxy)phenoxy)ethoxy)cyclobutanecarboxylate (299 mg, 711 μmol) in DMF (5 mL) was added K$_2$CO$_3$ (98.3 mg, 711 μmol). The mixture was then stirred at 50° C. overnight.

After the reaction was completed, to the reaction was added water (30 mL) and the resulting suspension was filtered. The solid was collected and dried in vacuo to give methyl 3-[2-[2-bromo-4-(8-chloro-4-oxo-chromen-2-yl)phenoxy]ethoxy]cyclobutanecarboxylate (200 mg, 55.4%) as a yellow solid. MS obsd. (ESI$^+$) [(M+H)$^+$]: 507.1.

Step 3: Preparation of cis-3-[2-[2-bromo-4-(8-chloro-4-oxo-chromen-2-yl)phenoxy]ethoxy]cyclobutanecarboxylic acid

44

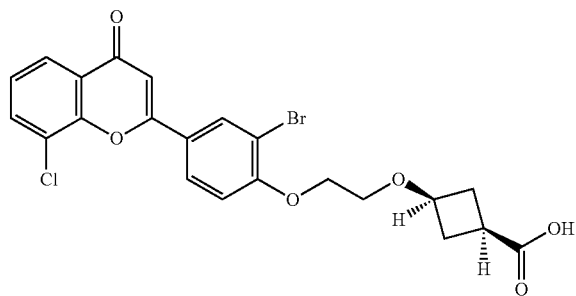

To a solution of methyl 3-[2-[2-bromo-4-(8-chloro-4-oxo-chromen-2-yl)phenoxy]ethoxy]cyclobutanecarboxylate (200 mg, 394 μmol) in the mixed solvent of MeOH (5 mL) and water (1 mL) was added LiOH (40.9 mg, 1.71 mmol). The mixture was then stirred at room temperature for 4 hours. After the reaction was completed, the mixture was concentrated in vacuo and the residue was purified by prepare HPLC to give cis configuration of 3-[2-[2-bromo-4-(8-chloro-4-oxo-chromen-2-yl)phenoxy]ethoxy]cyclobutanecarboxylic acid (90 mg, 32%) as a white foam, the trans isomer was not collected in the purification. $^1$H NMR (DMSO-d$_6$, 400 MHz): δ ppm 12.0-12.4 (m, 1H), 8.1-8.2 (m, 1H), 8.05-8.12 (m, 1H), 7.98-8.04 (m, 2H), 7.46-7.56 (m, 1H), 7.35-7.41 (m, 1H), 7.15-7.22 (m, 1H), 4.28-4.33 (m, 2H), 3.91-4.08 (m, 1H), 3.66-3.78 (m, 2H), 2.54-2.65 (m, 1H), 2.38-2.46 (m, 2H), 1.91-2.05 (m, 2H). MS obsd. (ESI$^+$) [(M+H)$^+$]: 493.1.

Example 45

Cis-3-[2-[4-(8-chloro-4-oxo-chromen-2-yl)-2-cyclopropyl-phenoxy]ethoxy]cyclobutanecarboxylic acid

45

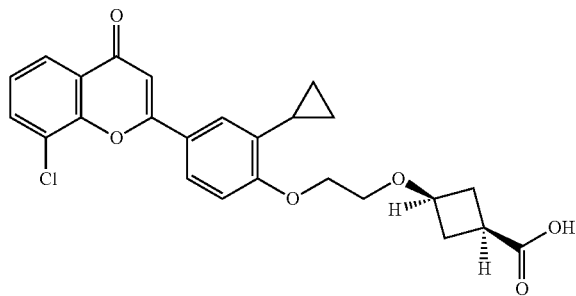

Step 1: Preparation of methyl 3-[2-[4-(8-chloro-4-oxo-chromen-2-yl)-2-cyclopropyl-phenoxy]ethoxy]cyclobutanecarboxylate 45a

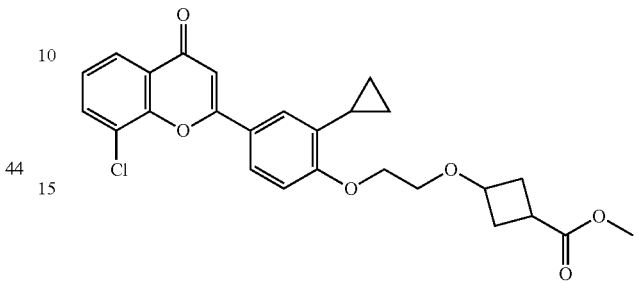

A mixture methyl 3-[2-[2-bromo-4-(8-chloro-4-oxo-chromen-2-yl)phenoxy]ethoxy]cyclobutanecarboxylate (200 mg, 394 μmol), cyclopropylboronic acid (67.7 mg, 788 μmol), K$_3$PO$_4$ (251 mg, 1.18 mmol) and Bis(triphenylphosphine)palladium(II) chloride (55.3 mg, 78.8 μmol) in the mixed solvent of dioxane (5 mL) and water (2 mL) was heated at 100° C. under microwave radiation for 2 hours. After the reaction was completed, the mixture was diluted with water (15 mL) and the resulting mixture was extracted with EtOAc (20 mL) three times. The combined organic layer was washed with brine, dried over Na$_2$SO$_4$ and concentrated in vacuo. The residue was purified by column chromatography on silica gel (elution with PE:EA 100:1-2:1) to give methyl 3-[2-[4-(8-chloro-4-oxo-chromen-2-yl)-2-cyclopropyl-phenoxy]ethoxy]cyclobutanecarboxylate (150 mg, 81.2%) as a yellow solid. MS obsd. (ESI$^+$) [(M+H)$^+$]: 469.1.

Step 2: Preparation of cis-3-[2-[4-(8-chloro-4-oxo-chromen-2-yl)-2-cyclopropyl-phenoxy]ethoxy]cyclobutanecarboxylic acid

45

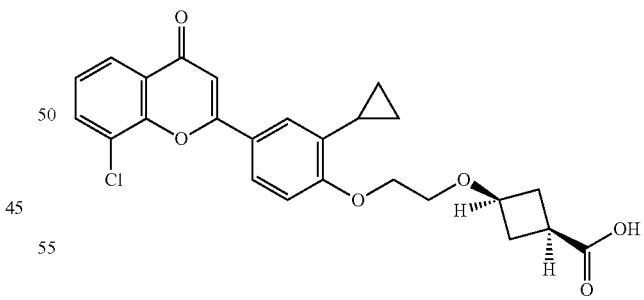

To a mixture of methyl 3-[2-[4-(8-chloro-4-oxo-chromen-2-yl)-2-cyclopropyl-phenoxy]ethoxy]cyclobutanecarboxylate (150 mg, 320 μmol) in the mixed solvent of MeOH (5 mL) and water (1 mL) was added LiOH (24 mg, 1.0 mmol). The mixture was then stirred at room temperature for 4 hours. After the reaction was completed, the mixture was concentrated in vacuo and the residue was purified by prepare HPLC to give cis-3-[2-[4-(8-chloro-4-oxo-chromen-2-yl)-2-cyclopropyl-phenoxy]ethoxy]cyclobutanecarboxylic acid (11 mg, 11.6%) as a white foam, the trans-isomer was not collected in the purification. ¹H NMR (DMSO-d$_6$, 400 MHz): δ ppm 12.05-12.18 (m, 1H), 7.87-8.05 (m, 3H), 7.41-7.59 (m, 2H), 7.10-7.23 (m, 2H), 4.18-4.28 (m, 2H), 3.94-4.03 (m, 1H), 3.67-3.75 (m, 2H), 2.56-2.65 (m, 2H), 2.38-2.45 (m, 2H), 2.14-2.24 (m, 1H), 1.94-2.08 (m, 1H), 0.96-1.03 (m, 2H), 0.79-0.87 (m, 2H). MS obsd. (ESI⁺) [(M+H)⁺]: 455.1.

Example 46

3-[2-[4-(8-chloro-4-oxo-chromen-2-yl)-2-cyano-phenoxy]ethoxy]cyclobutanecarboxylic acid

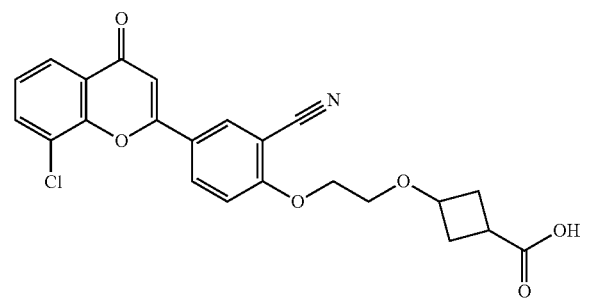

46

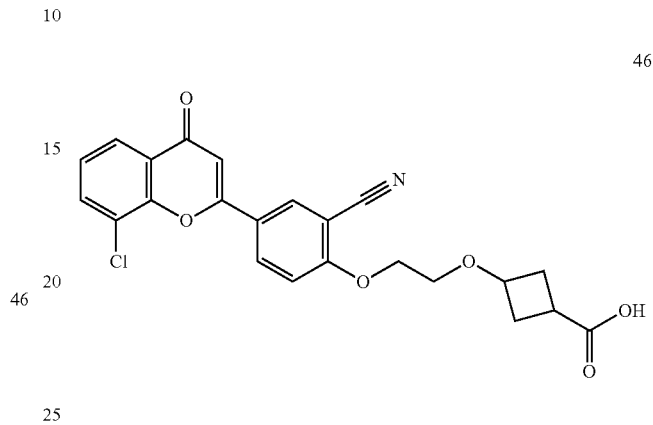

46a

Step 1: Preparation of methyl 3-[2-[4-(8-chloro-4-oxo-chromen-2-yl)-2-cyano-phenoxy]ethoxy]cyclobutanecarboxylate A mixture of methyl 3-[2-[2-bromo-4-(8-chloro-4-oxo-chromen-2-yl)phenoxy]ethoxy]cyclobutanecarboxylate (150 mg, 295 µmol) and copper (I) cyanide (106 mg, 1.18 mmol) in NMP (4 mL) was heated at 160° C. under microwave radiation for 1.5 hours. After the reaction was completed, the mixture was diluted with EtOAc (50 mL). The resulting suspension was filtered through silica pad and the filtrate was concentrate in vacuo to give the crude methyl 3-[2-[4-(8-chloro-4-oxo-chromen-2-yl)-2-cyano-phenoxy] ethoxy]cyclobutanecarboxylate (134 mg, 100%) as a brown oil, which was used in next step directly without further purification.

Step 2: Preparation of 3-[2-[4-(8-chloro-4-oxo-chromen-2-yl)-2-cyano-phenoxy]ethoxy]cyclobutanecarboxylic acid To a solution of methyl 3-[2-[4-(8-chloro-4-oxo-chromen-2-yl)-2-cyano-phenoxy]ethoxy]cyclobutanecarboxylate (130 mg, 286 µmol) in the mixed solvent of MeOH (10 mL) and water (2 mL) was added LiOH (100 mg, 4.18 mmol). After the reaction was completed, the mixture was quenched with AcOH (0.3 g) and the resulting mixture was purified by preparative HPLC to give 3-[2-[4-(8-chloro-4-oxo-chromen-2-yl)-2-cyano-phenoxy]ethoxy]cyclobutanecarboxylic acid (22 mg, 17.1%) as a white solid. ¹H NMR (DMSO-d$_6$, 400 MHz): δ ppm 8.47-8.38 (m, 1H), 8.35-8.27 (m, 1H), 7.99-7.90 (m, 2H), 7.50-7.38 (m, 2H), 7.19-7.12 (m, 1H), 4.36-4.24 (m, 2H), 3.98-3.86 (m, 1H), 3.68-3.61 (m, 2H), 2.48 (m, 2H), 2.16-2.03 (m, 1H), 1.98-1.87 (m, 2H). MS obsd. (ESI⁺) [(M+H)⁺]: 440.1.

Example 47

3-[2-[4-(8-chloro-4-oxo-chromen-2-yl)-2-methyl-phenoxy]ethoxy]cyclobutanecarboxylic acid

47

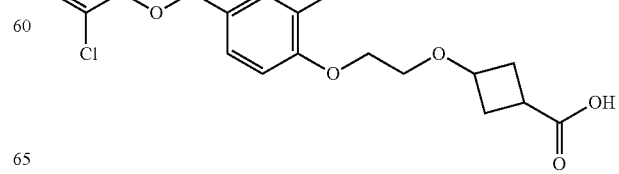

Step 1: Preparation of 8-chloro-2-(4-hydroxy-3-methyl-phenyl)chromen-4-one

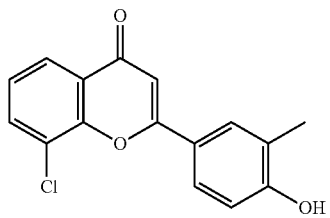

47a

Compound 47a was prepared in analogy to the procedure described for the preparation of compound 3c by using 4-methoxy-3-methyl-benzaldehyde as the starting material instead of 4-methoxybenzaldehyde in Step 1.

Step 2: Preparation of 3-[2-[4-(8-chloro-4-oxo-chromen-2-yl)-2-methyl-phenoxy]ethoxy]cyclobutanecarboxylic acid

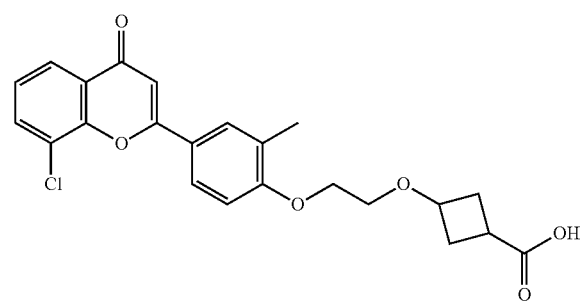

47

Example 47 was prepared in analogy to the procedure described for the preparation of Example 15 by using 8-chloro-2-(4-hydroxy-3-methyl-phenyl)chromen-4-one as the starting material instead of 8-chloro-2-(4-hydroxyphenyl)chromen-4-one in Step 5.

Example 47: $^1$H NMR (DMSO-$d_6$, 400 MHz): δ ppm 12.27-11.83 (m, 1H), 8.03-7.91 (m, 4H), 7.49 (t, J=7.8 Hz, 1H), 7.16 (d, J=8.6 Hz, 1H), 7.05 (s, 1H), 4.22-4.16 (m, 2H), 3.98 (t, J=7.0 Hz, 1H), 3.72-3.66 (m, 2H), 2.58 (d, J=8.1 Hz, 1H), 2.47-2.38 (m, 2H), 2.26 (s, 3H), 2.05-1.92 (m, 2H) MS obsd. (ESI$^+$) [(M+H)$^+$]:429.2.

Example 48

3-[2-[4-(8-chloro-4-oxo-chromen-2-yl)-2-isopropyl-phenoxy]ethoxy]cyclobutanecarboxylic acid

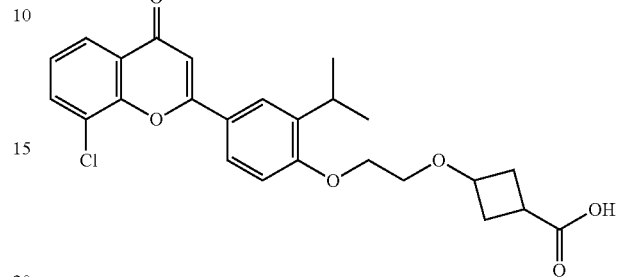

48

Step 1: Preparation of 8-chloro-2-(4-hydroxy-3-isopropyl-phenyl)chromen-4-one

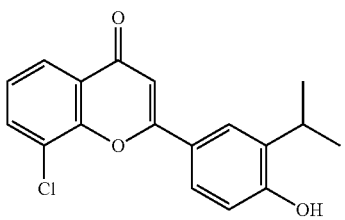

48a

Compound 48a was prepared in analogy to the procedure described for the preparation of compound 3c by using 3-isopropyl-4-methoxy-benzaldehyde as the starting material instead of 4-methoxybenzaldehyde in Step 1.

Step 2: Preparation of 3-[2-[4-(8-chloro-4-oxo-chromen-2-yl)-2-isopropyl-phenoxy]ethoxy]cyclobutanecarboxylic acid

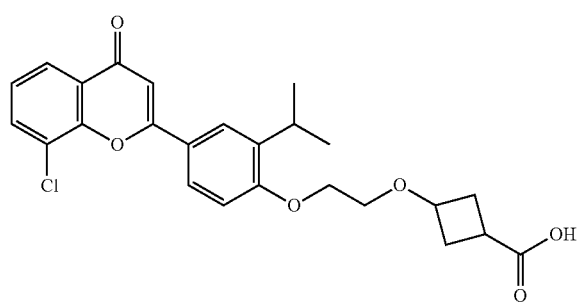

48

Example 48 was prepared in analogy to the procedure described for the preparation of Example 15 by using 8-chloro-2-(4-hydroxy-3-isopropyl-phenyl)chromen-4-one as the starting material instead of 8-chloro-2-(4-hydroxyphenyl)chromen-4-one in Step 5.

Example 48: $^1$H NMR (DMSO-d$_6$, 400 MHz): δ ppm 8.04-7.91 (m, 4H), 7.53-7.43 (m, 1H), 7.22-7.14 (m, 1H), 7.13-7.05 (m, 1H), 4.25-4.16 (m, 2H), 3.98-3.89 (m, 1H), 3.71-3.65 (m, 2H), 2.90-2.80 (m, 1H), 2.61-2.57 (m, 0.6H), 2.44-2.33 (m, 2H), 2.16-2.07 (m, 0.4H), 2.03-1.92 (m, 2H), 1.34-1.17 (m, 6H). MS obsd. (ESI$^+$) [(M+H)$^+$]:457.3.

Example 50

3-[2-[4-(8-chloro-4-oxo-chromen-2-yl)-3-methoxy-phenoxy]ethoxy]cyclobutanecarboxylic acid

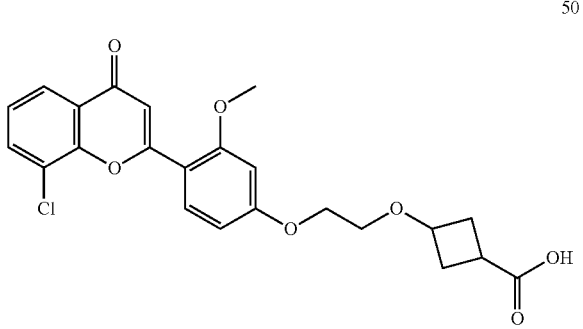 [SMILES: COc1cc(OCCOC2CC(C(=O)O)C2)ccc1-c1cc(=O)c2cccc(Cl)c2o1]

Step 1: Preparation of 8-chloro-2-(2-fluoro-4-hydroxy-phenyl)chromen-4-one

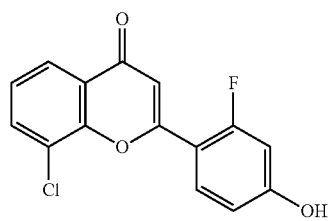

Compound 49a was prepared in analogy to the procedure described for the preparation of compound 3c by using 2-fluoro-4-methoxy-benzaldehyde as the starting material instead of 4-methoxybenzaldehyde in Step 1.

Step 2: Preparation of methyl 3-[2-[4-(8-chloro-4-oxo-chromen-2-yl)-3-fluoro-phenoxy]ethoxy]cyclobutanecarboxylate

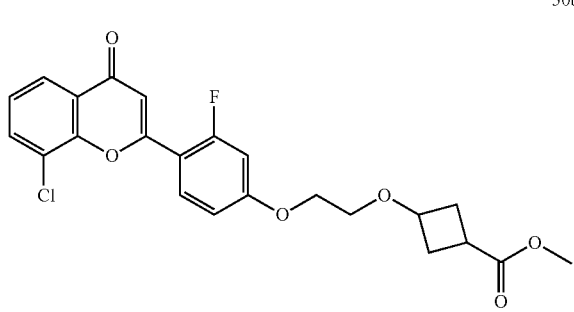

Compound 49b was prepared in analogy to the procedure described for the preparation of compound 15f by using 8-chloro-2-(2-fluoro-4-hydroxy-phenyl)chromen-4-one as the starting material instead of 8-chloro-2-(4-hydroxyphenyl)chromen-4-one in Step 5.

Step 2: Preparation of 3-[2-[4-(8-chloro-4-oxo-chromen-2-yl)-3-methoxy-phenoxy]ethoxy]cyclobutanecarboxylic acid

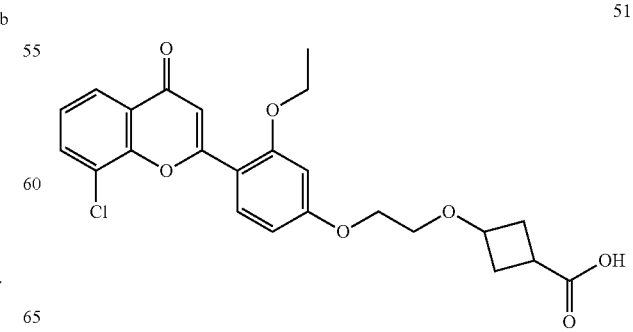

To a mixture of methyl 3-[2-[4-(8-chloro-4-oxo-chromen-2-yl)-3-fluoro-phenoxy]ethoxy]cyclobutanecarboxylate (120 mg, crude, 60% purity) in DMF (3 mL) was added LiOH (48 mg, 2 mmol), MeOH (10 mL) and water (1 mL) and the mixture was then stirred at room temperature for 72 hours. The mixture was then filtered and the filtrate was concentrated in vacuo, the residue was purified by preparative HPLC to give 3-[2-[4-(8-chloro-4-oxo-chromen-2-yl)-3-methoxy-phenoxy]ethoxy]cyclobutanecarboxylic acid (20 mg, 10.3%) as a white solid.

Example 50: $^1$H NMR (DMSO-d$_6$, 400 MHz): δ ppm 12.19 (s, 1H), 7.98 (d, J=7.5 Hz, 3H), 7.47 (s, 1H), 7.05 (s, 1H), 6.81 (s, 2H), 4.26-4.19 (m, 2H), 3.97 (s, 3H), 3.95-3.90 (m, 1H), 3.70-3.64 (m, 2H), 2.63-2.55 (m, 0.7H), 2.47-2.40 (m, 2H), 2.22-2.13 (m, 0.3H), 2.04-1.96 (m, 2H). MS obsd. (ESI$^+$) [(M+H)$^+$]:445.2.

Example 51

3-[2-[4-(8-chloro-4-oxo-chromen-2-yl)-3-ethoxy-phenoxy]ethoxy]cyclobutanecarboxylic acid Step 1: Preparation of (E)-1-(3-chloro-2-hydroxy-phenyl)-3-(2-ethoxy-4-methoxy-phenyl)prop-2-en-1-one

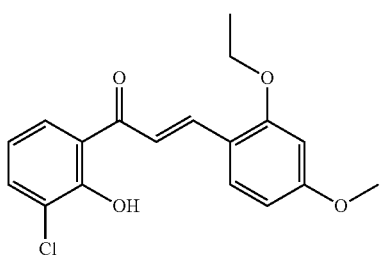

51a

To a mixture of 2-fluoro-4-methoxybenzaldehyde (600 mg, 3.89 mmol) and 1-(3-chloro-2-hydroxyphenyl)ethanone (664 mg, 3.89 mmol) in EtOH (25 mL) was added KOH (436 mg, 7.79 mmol) and the mixture was then stirred at 60° C. overnight. The reaction was then adjusted to pH~4.0 by addition of 2N HCl and the resulting suspension was filtered. The solid was collected and dried in vacuo to give the crude (E)-1-(3-chloro-2-hydroxy-phenyl)-3-(2-ethoxy-4-methoxy-phenyl)prop-2-en-1-one (51a) (600 mg, 50% purity) as a orange solid, which was used in next step directly without further purification. MS obsd. (ESI$^+$) [(M+H)$^+$]:333.2.

Step 2: Preparation of 8-chloro-2-(2-ethoxy-4-hydroxy-phenyl)chromen-4-one

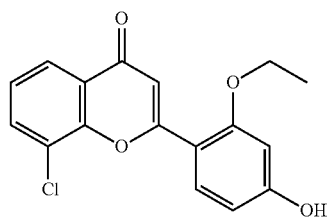

51b

Compound 51b was prepared in analogy to the procedure described for the preparation of compound 3c by using (E)-1-(3-chloro-2-hydroxy-phenyl)-3-(2-ethoxy-4-methoxy-phenyl)prop-2-en-1-one as the starting material instead of (E)-1-(3-chloro-2-hydroxy-phenyl)-3-(4-methoxyphenyl)prop-2-en-1-one in Step 2.

Step 3: Preparation of 3-[2-[4-(8-chloro-4-oxo-chromen-2-yl)-3-ethoxy-phenoxy]ethoxy]cyclobu-tanecarboxylic acid

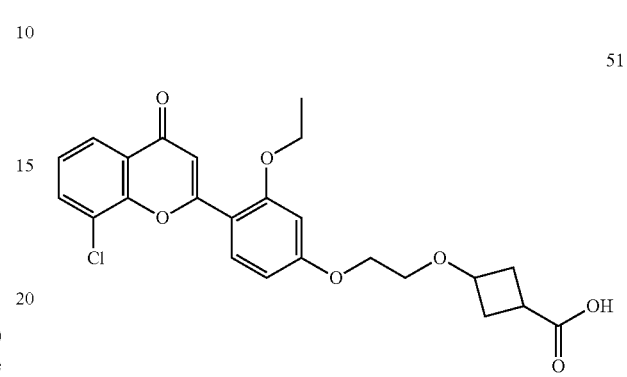

51

Example 51 was prepared in analogy to the procedure described for the preparation of Example 15 by using 8-chloro-2-(2-ethoxy-4-hydroxy-phenyl)chromen-4-one as the starting material instead of 8-chloro-2-(4-hydroxyphe-nyl)chromen-4-one in Step 5.

Example 51: $^1$H NMR (DMSO-d$_6$, 400 MHz): δ ppm 7.98 (d, J=8.1 Hz, 3H), 7.51-7.43 (m, 1H), 7.10 (s, 1H), 6.84-6.77 (m, 2H), 4.28-4.15 (m, 4H), 3.99-3.90 (m, 1H), 3.70-3.63 (m, 2H), 2.63-2.53 (m, 2H), 2.45-2.40 (m, 0.5H), 2.22-2.11 (m, 0.5H), 2.05-1.94 (m, 2H), 1.43 (t, J=6.9 Hz, 3H). MS obsd. (ESI$^+$) [(M+H)$^+$]:459.2.

Example 53

3-[2-[4-(3,8-dichloro-4-oxo-chromen-2-yl)phenoxy]ethoxy]cyclobutanecarboxylic acid

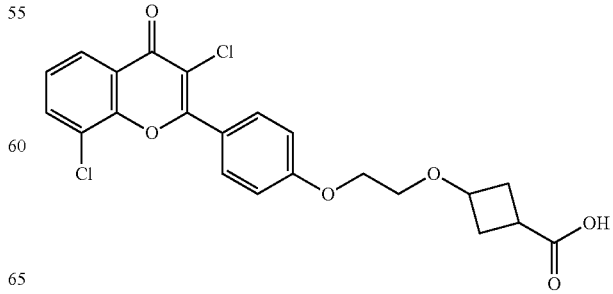

53

Step 1: Preparation of ethyl 3-[2-[4-(3,8-dichloro-4-oxo-chromen-2-yl)phenoxy]ethoxy]cyclobutanecarboxylate

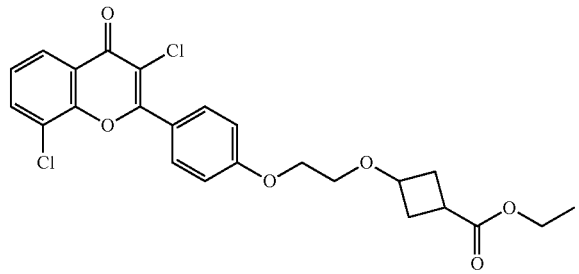

53a

To a solution of ethyl 3-[2-[4-(8-chloro-4-oxo-chromen-2-yl)phenoxy]ethoxy]cyclobutanecarboxylate (120 mg, 271 μmol) and 2,6-dimethylpyridine (29 mg, 0.5 mL, 271 μmol) in dichloromethane (12 mL) was added 1-chloropyrrolidine-2,5-dione (109 mg, 813 μmol) and the mixture was then stirred at 50° C. for 48 hours. After the reaction was completed, the mixture was concentrated in vacuo and the residue was purified by column chromatography on silica gel to give ethyl 3-[2-[4-(3,8-dichloro-4-oxo-chromen-2-yl)phenoxy]ethoxy]cyclobutanecarboxylate (120 mg, 92.8%) as a yellow solid. MS obsd. (ESI$^+$) [(M+H)$^+$]:477.2.

Step 2: Preparation of 3-[2-[4-(3,8-dichloro-4-oxo-chromen-2-yl)phenoxy]ethoxy]cyclobutanecarboxylic acid

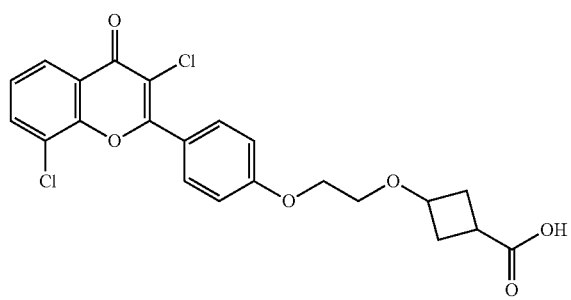

53

To a solution of ethyl 3-[2-[4-(3,8-dichloro-4-oxo-chromen-2-yl)phenoxy]ethoxy]cyclobutanecarboxylate (120 mg, 251 umol) in the mixed solvent of THF (5 mL), MeOH (5 mL) and Water (1 mL) was added LiOH (36.1 mg, 1.51 mmol) and the mixture was then stirred at room temperature for 4 hours. After the reaction was completed, to the mixture was added AcOH (120 mg, 2 mmol) and the resulting mixture was concentrated in vacuo. The residue was then purified by preparative HPLC to give 3-[2-[4-(3,8-dichloro-4-oxo-chromen-2-yl)phenoxy]ethoxy]cyclobutanecarboxylic acid (26 mg, 21.9%) as a white solid. $^1$H NMR (DMSO-d$_6$, 400 MHz): δ ppm$^1$ 12.17-11.92 (br, 1H), 8.06 (dt, J=1.5, 8.2 Hz, 2H), 8.01-7.94 (m, 2H), 7.55 (t, J=7.9 Hz, 1H), 7.23-7.17 (m, 2H), 4.26-4.16 (m, 2H), 3.95 (q, J=7.5 Hz, 1H), 3.72-3.65 (m, 2H), 2.61-2.56 (m, 1H), 2.46-2.40 (m, 2H), 2.04-1.94 (m, 2H). MS obsd. (ESI$^+$) [(M+H)$^+$]:449.1.

Example 55

Cis-3-[2-[4-(8-chloro-3-hydroxy-4-oxo-chromen-2-yl)phenoxy]ethoxy]cyclobutanecarboxylic acid

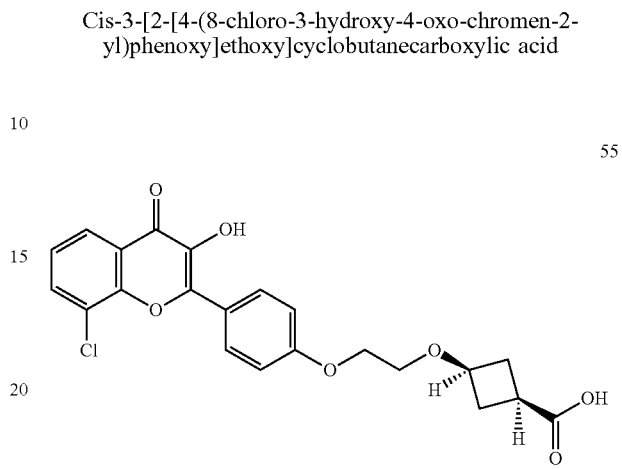

55

Step 1: Preparation of 3-[2-[4-[(E)-3-(3-chloro-2-hydroxy-phenyl)-3-oxo-prop-1-enyl]phenoxy]ethoxy]cyclobutanecarboxylic acid

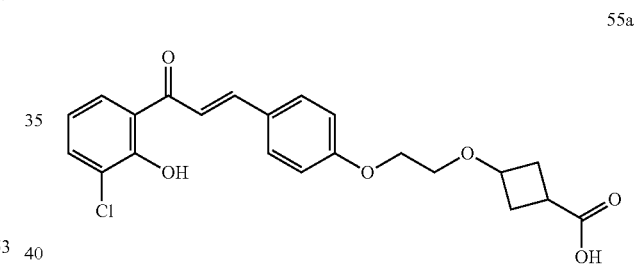

55a

Compound 55a was prepared in analogy to the procedure described for the preparation of compound 19b by using 1-(3-chloro-2-hydroxy-phenyl)ethanone as the starting material instead of 1-(3-chloro-2,4-dihydroxy-phenyl)ethanone in Step 5.

Step 2: Preparation of cis-3-[2-[4-(8-chloro-3-hydroxy-4-oxo-chromen-2-yl)phenoxy]ethoxy]cyclobutanecarboxylic acid

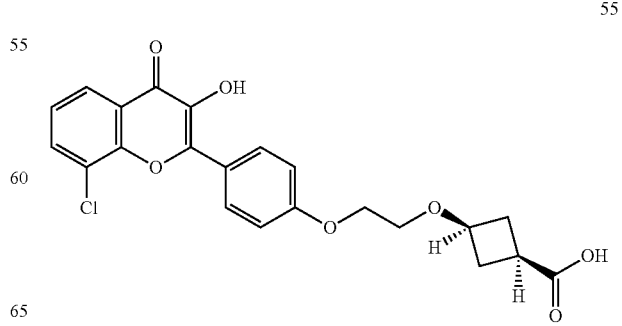

55

To a solution of 3-[2-[4-[(E)-3-(3-chloro-2-hydroxy-phenyl)-3-oxo-prop-1-enyl]phenoxy]ethoxy]cyclobutanecarboxylic acid (50 mg, 120 μmol) in Acetone (4 mL) was added 4N NaOH solution (1.5 mL) and H$_2$O$_2$ (1.5 mL, 30%) at room temperature and the reaction was then stirred at room temperature for 2 hours. After the reaction was completed, the mixture was adjusted to pH~2 by addition of 4N HCl solution. The solid was collected and further purified by recrystallization (EtOH, 5 mL) to give cis-3-[2-[4-(8-chloro-3-hydroxy-4-oxo-chromen-2-yl)phenoxy]ethoxy]cyclobutanecarboxylic acid (25 mg, 47.4%) as a yellow solid, the trans isomer was not collected in the purification. $^1$H NMR (DMSO-d$_6$, 400 MHz): δ ppm 12.09 (br. s., 1H), 9.76 (s, 1H), 8.24 (d, J=9.0 Hz, 2H), 8.07 (dd, J=1.5, 7.9 Hz, 1H), 7.98 (dd, J=1.5, 7.7 Hz, 1H), 7.46 (t, J=7.9 Hz, 1H), 7.18 (d, J=9.2 Hz, 2H), 4.21-4.14 (m, 2H), 3.95 (s, 1H), 3.71-3.64 (m, 2H), 2.63-2.54 (m, 1H), 2.47-2.40 (m, 2H), 2.04-1.95 (m, 2H). MS obsd. (ESI$^+$) [(M+H)$^+$]:431.5.

Example 56

Cis-3-[2-[4-(8-chloro-3-methoxy-4-oxo-chromen-2-yl)phenoxy]ethoxy]cyclobutanecarboxylic acid

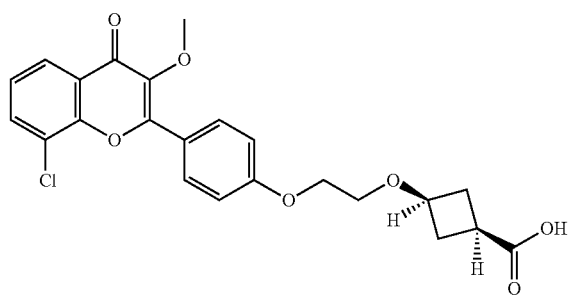

56

To a solution of cis-3-[2-[4-(8-chloro-3-hydroxy-4-oxo-chromen-2-yl)phenoxy]ethoxy]cyclobutanecarboxylic acid (50 mg, 116 μmol) and Cs$_2$CO$_3$ (94.5 mg, 290 μmol) in DMF (3 mL) was added MeI (41.2 mg, 18.1 μL, 290 μmol) at room temperature and then the mixture was stirred at 40° C. for 1 hour. Then to the mixture was added LiOH solution (1N in water, 0.5 mL) and the mixture was stirred at room temperature for 30 minutes. After the reaction was completed, the mixture was adjusted to pH~2 by addition of 2N HCl and the resulting mixture was concentrated in vacuo. The residue was purified by preparative HPLC to give cis-3-[2-[4-(8-chloro-3-methoxy-4-oxo-chromen-2-yl)phenoxy]ethoxy]cyclobutanecarboxylic acid (40 mg, 77.5%) as a yellow solid. $^1$H NMR (DMSO-d$_6$, 400 MHz): δ ppm 12.17 (br. s., 1H), 8.15-8.10 (m, 2H), 8.02 (ddd, J=1.5, 7.8, 17.9 Hz, 2H), 7.49 (t, J=7.9 Hz, 1H), 7.24-7.17 (m, 2H), 4.21-4.16 (m, 2H), 4.00-3.91 (m, 1H), 3.84 (s, 3H), 3.71-3.65 (m, 2H), 2.63-2.55 (m, 1H), 2.48-2.39 (m, 2H), 2.06-1.94 (m, 2H). MS obsd. (ESI$^+$) [(M+H)$^+$]:445.2.

Example 57

3-[2-[4-(8-chloro-4-oxo-thiochromen-2-yl)phenoxy]ethoxy]cyclobutanecarboxylic acid

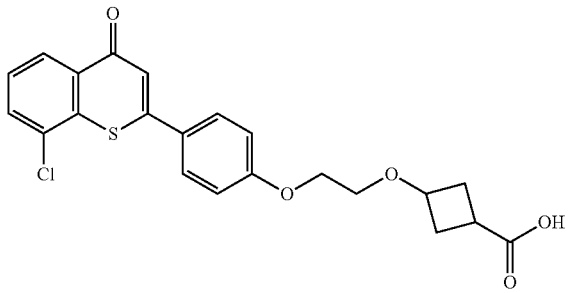

57

Step 1: Preparation of 8-chloro-2-(4-methoxyphenyl)thiochromen-4-one

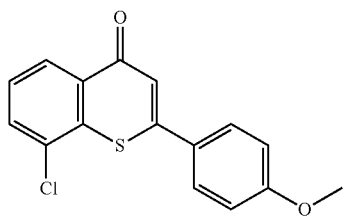

57a

A mixture of 2-chlorobenzenethiol (2.56 g, 2 mL, 17.7 mmol) and ethyl 3-(4-methoxyphenyl)-3-oxopropanoate (3.93 g, 3.39 mL, 17.7 mmol) in PPA (20 mL) was stirred at 120° C. overnight. The reaction was quenched by pouring into water (80 mL) and the resulting mixture was extracted with EtOAc (60 mL) three times. The combined organic layers were washed with brine, dried over anhydrous Na$_2$SO$_4$ and concentrated in vacuo. The residue was then purified by column chromatography on silica gel (elution with PE:EtOAc=5:1) to give 8-chloro-2-(4-methoxyphenyl)thiochromen-4-one (500 mg, 9.1%) as a grey solid. MS obsd. (ESI$^+$) [(M+H)$^+$]:303.1.

Step 2: Preparation of 8-chloro-2-(4-hydroxyphenyl)thiochromen-4-one

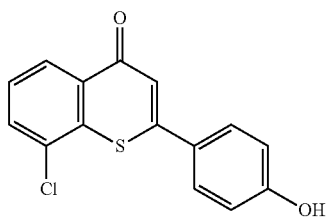

57b

Compound 57b was prepared in analogy to the procedure described for the preparation of compound 3c by using 8-chloro-2-(4-methoxyphenyl)thiochromen-4-one as the starting material instead of 8-chloro-2-(4-methoxyphenyl)chromen-4-one in Step 3.

Step 3: Preparation of 3-[2-[4-(8-chloro-4-oxo-thiochromen-2-yl)phenoxy]ethoxy]cyclobutanecarboxylic acid

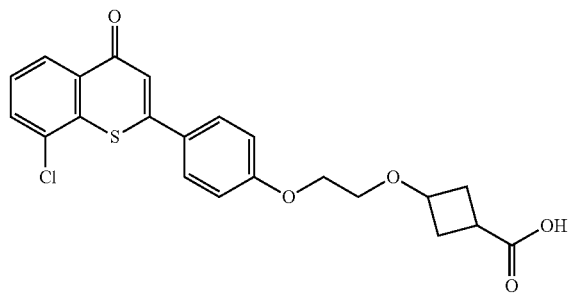

57

Example 57 was prepared in analogy to the procedure described for the preparation of Example 15 by using 8-chloro-2-(4-hydroxyphenyl)thiochromen-4-one as the starting material instead of 8-chloro-2-(4-hydroxyphenyl)chromen-4-one in Step 5.

Example 57: $^1$H NMR (DMSO-$d_6$, 400 MHz): δ ppm 12.19-12.07 (m, 1H), 8.35 (dd, J=1.3, 7.9 Hz, 1H), 8.00 (dd, J=1.2, 7.8 Hz, 1H), 7.87-7.79 (m, 2H), 7.68 (t, J=7.9 Hz, 1H), 7.28 (s, 1H), 7.17-7.11 (m, 2H), 4.21-4.15 (m, 2H), 4.07-3.90 (m, 1H), 3.67 (dd, J=3.9, 5.4 Hz, 2H), 2.64-2.53 (m, 1H), 2.48-2.36 (m, 2H), 2.22-1.94 (m, 2H). MS obsd. (ESI$^+$) [(M+H)$^+$]:431.2.

Example 58

2-[2-[4-(8-chloro-4-oxo-thiochromen-2-yl)phenoxy]ethoxy]acetic acid

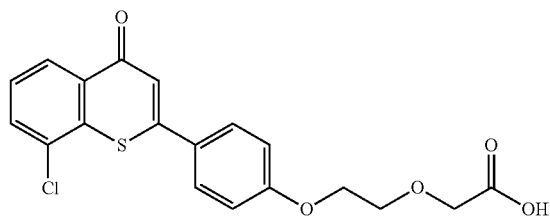

58

Step 1: Preparation of 8-chloro-2-[4-(2-hydroxyethoxy)phenyl]thiochromen-4-one

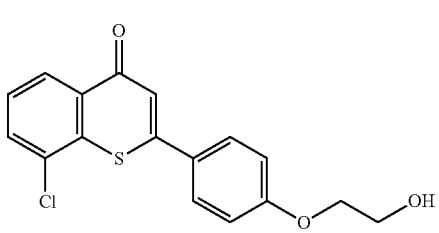

58a

To a solution of 8-chloro-2-(4-hydroxyphenyl)thiochromen-4-one (40 mg, 139 μmol,) and K$_2$CO$_3$ (38.3 mg, 277 μmol) in DMF (3 mL) was added 2-bromoethanol (26 mg, 14.8 μL, 208 μmol) at room temperature and the mixture was then stirred at 80° C. overnight. The mixture was then quenched with water (10 mL) and the resulting suspension was filtered. The solid was collected and dried in vacuo to give the crude 8-chloro-2-[4-(2-hydroxyethoxy)phenyl]thiochromen-4-one (40 mg, 85%) as a white solid, which was used in the next step without further purification. MS obsd. (ESI$^+$) [(M+H)$^+$]:333.2.

Step 2: Preparation of 2-[2-[4-(8-chloro-4-oxo-thiochromen-2-yl)phenoxy]ethoxy]acetic acid

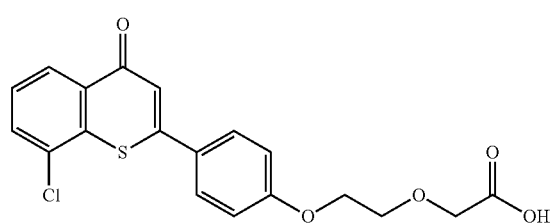

58

Example 58 was prepared in analogy to the procedure described for the preparation of Example 9 by using 8-chloro-2-[4-(2-hydroxyethoxy)phenyl]thiochromen-4-one as the starting material instead of 8-chloro-2-[4-(2-hydroxyethoxy)phenyl]chromen-4-one in Step 1.

Example 58: $^1$H NMR (DMSO-$d_6$, 400 MHz): δ ppm 12.03-11.97 (m, 1H), 8.36 (d, J=7.8 Hz, 1H), 8.00 (d, J=7.8 Hz, 1H), 7.84 (d, J=8.8 Hz, 2H), 7.68 (t, J=7.9 Hz, 1H), 7.28 (s, 1H), 7.16 (d, J=8.8 Hz, 2H), 4.25-4.20 (m, 2H), 4.08 (s, 2H), 3.88-3.84 (m, 2H). MS obsd. (ESI$^+$) [(M+H)$^+$]:391.1.

Example 59

2-[2-[4-(8-chloro-3-hydroxy-4-oxo-chromen-2-yl)phenoxy]ethoxy]acetic acid

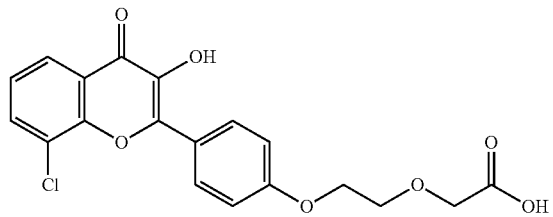

59

Step 1: Preparation of 8-chloro-3-hydroxy-2-[4-(2-hydroxyethoxy)phenyl]chromen-4-one

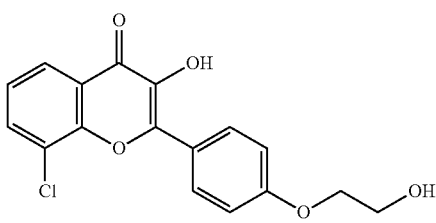

59a

To a solution of (E)-1-(3-chloro-2-hydroxy-phenyl)-3-[4-(2-hydroxyethoxy)phenyl]prop-2-en-1-one (500 mg, 1.57 mmol) and NaOH (3.92 ml, 15.7 mmol) in EtOH (5 ml) was added $H_2O_2$ (1.78 g, 1.6 mL, 15.7 mmol) dropwise at room temperature. After the addition, the mixture was stirred at room temperature for additional 2 hours. The mixture was then adjusted to pH~2 by addition of conc. HCl and the resulting suspension was then filtered. The solid was collected and dried in vacuo to give 8-chloro-3-hydroxy-2-[4-(2-hydroxyethoxy)phenyl]chromen-4-one (340 mg, 61.9%) as a yellow solid. MS obsd. (ESI$^+$) [(M+H)$^+$]:333.1.

Step 2: Preparation of 8-chloro-2-[4-(2-hydroxyethoxy)phenyl]-3-(methoxymethoxy)chromen-4-one

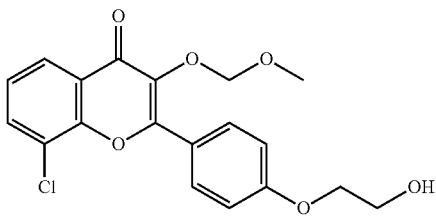

59b

To a solution of 8-chloro-3-hydroxy-2-[4-(2-hydroxyethoxy)phenyl]chromen-4-one (340 mg, 1.02 mmol) and $K_2CO_3$ (212 mg, 1.53 mmol) in DMF (8 mL) was added bromo(methoxy)methane (153 mg, 100 μL, 1.23 mmol) at room temperature and the mixture was then stirred at room temperature overnight. The reaction was then diluted with water (30 mL) and extracted with EtOAc (30 mL) three times. The combined organic layer was washed with brine, dried over anhydrous $Na_2SO_4$ and concentrated in vacuo. The residue was then purified by column chromatography on silica gel to give 8-chloro-2-[4-(2-hydroxyethoxy)phenyl]-3-(methoxymethoxy)chromen-4-one (200 mg, 41.6%) as a yellow solid. MS obsd. (ESI$^+$) [(M+H)$^+$]:377.1.

Step 3: Preparation of tert-butyl 2-[2-[4-[8-chloro-3-(methoxymethoxy)-4-oxo-chromen-2-yl]phenoxy]ethoxy]acetate

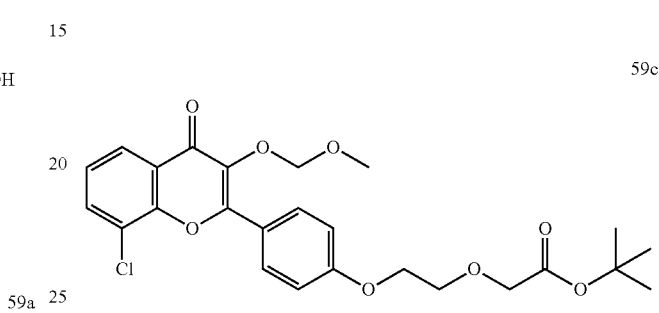

59c

To a solution of 8-chloro-2-[4-(2-hydroxyethoxy)phenyl]-3-(methoxymethoxy)chromen-4-one (100 mg, 265 μmol) in DMSO (5 mL) was added NaH (31.8 mg, 796 μmol) at room temperature and the mixture was stirred at room temperature for 15 minutes. Then to the resulting mixture was added tert-butyl 2-bromoacetate (155 mg, 796 μmol) and the mixture was stirred at room temperature for 8 hours. After the reaction was completed, the mixture was diluted with water (30 mL) and the mixture was extracted with EtOAc (30 mL) three times. The combined organic layer was washed with brine, dried over anhydrous $Na_2SO_4$ and concentrated in vacuo to give the crude tert-butyl 2-[2-[4-[8-chloro-3-(methoxymethoxy)-4-oxo-chromen-2-yl]phenoxy]ethoxy]acetate (130 mg, 100%) as a solid, which was used in the next step directly without further purification. MS obsd. (ESI$^+$) [(M+H)$^+$]:491.2.

Step 4: Preparation of 2-[2-[4-(8-chloro-3-hydroxy-4-oxo-chromen-2-yl)phenoxy]ethoxy]acetic acid

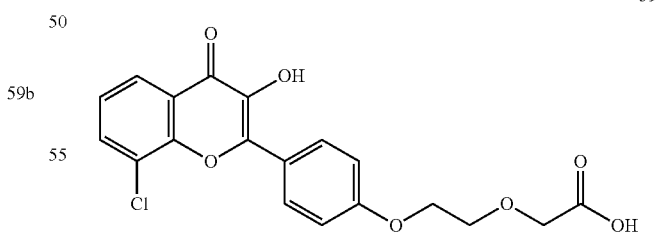

59

A mixture of tert-butyl 2-[2-[4-[8-chloro-3-(methoxymethoxy)-4-oxo-chromen-2-yl]phenoxy]ethoxy]acetate (130 mg, 265 μmol) in the mixed solvent of THF (3 mL) and conc. HCl (3 mL) was stirred at room temperature overnight. After the reaction was completed, the reaction mixture was concentrated in vacuo and the residue was purified by preparative HPLC to give 2-[2-[4-(8-chloro-3-hydroxy-4-oxo-chromen-2-yl)phenoxy]ethoxy]acetic acid (40 mg, 36.6%) as a yellow solid. $^1$H NMR (DMSO-d$_6$, 400 MHz): δ ppm 12.55 (br. s., 1H), 9.76 (br. s., 1H), 8.24 (d, J=9.0 Hz, 2H), 8.07 (dd, J=1.5, 8.1 Hz, 1H), 7.98 (dd, J=1.5, 7.6 Hz, 1H), 7.46 (t, J=7.8 Hz, 1H), 7.19 (d, J=9.3 Hz, 2H), 4.27-4.18 (m, 2H), 4.11 (s, 2H), 3.92-3.81 (m, 2H). MS obsd. (ESI$^+$) [(M+H)$^+$]: 391.1.

Example 60

3-[2-[4-(8-chloro-4-oxo-chromen-2-yl)-3-morpholino-phenoxy]ethoxy]cyclobutanecarboxylic acid

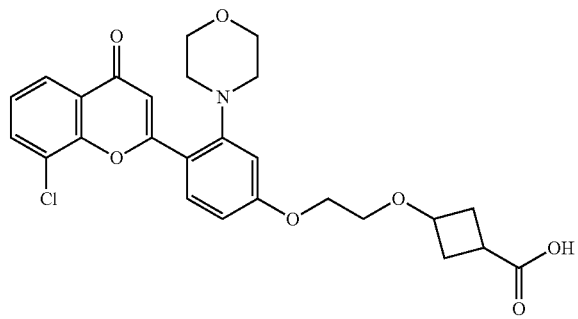

Step 1: Preparation of 2-(2-bromo-4-hydroxy-phenyl)-8-chloro-chromen-4-one

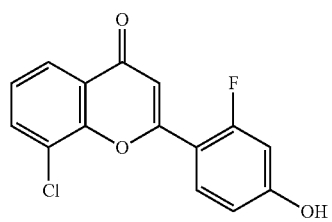

Compound 60a was prepared in analogy to the procedure described for the preparation of intermediate 3c by using 2-bromo-4-methoxy-benzaldehyde as the starting material instead of 4-methoxybenzaldehyde in Step 1.

Step 2: Preparation of methyl 3-[2-[3-bromo-4-(8-chloro-4-oxo-chromen-2-yl)phenoxy]ethoxy]cyclobutanecarboxylate

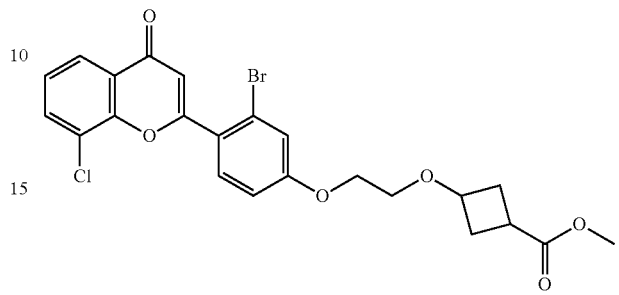

Compound 60 b was prepared in analogy to the procedure described for the preparation of compound 15f by using 2-(2-bromo-4-hydroxy-phenyl)-8-chloro-chromen-4-one as the starting material instead of 8-chloro-2-(4-hydroxyphenyl)chromen-4-one in Step 5.

Step 3: Preparation of 3-[2-[4-(8-chloro-4-oxo-chromen-2-yl)-3-morpholino-phenoxy]ethoxy]cyclobutanecarboxylic acid

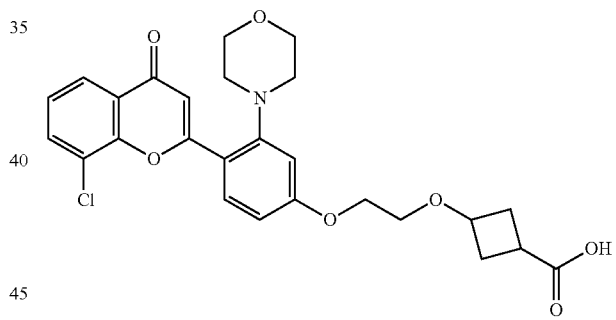

To a mixture of methyl 3-(2-(3-bromo-4-(8-chloro-4-oxo-4H-chromen-2-yl)phenoxy)ethoxy)cyclobutanecarboxylate (100 mg, 197 μmol), morpholine (51.5 mg, 591 μmol), TEA (159 mg, 220 μl, 1.58 mmol), sodium tert-butoxide (75.7 mg, 788 μmol), 2'-bis(diphenylphosphino)-1,1'-binaphthalene (83 mg, 133 μmol) in dioxane (4 mL) was added Pd$_2$(dba)$_3$ (80 mg, 87.4 μmol) and the mixture was then stirred at 110° C. for 2 hours. After the reaction was completed, the mixture was partitioned between EtOAc (15 mL) and water (15 mL), the organic layer was separated out. The aquatic phase was extracted with EtOAc (15 mL) twice. The organic layer was combined, washed with brine, dried over Na$_2$SO$_4$ and concentrated in vacuo. The residue was purified by preparative HPLC to give 3-(2-(4-(8-chloro-4-oxo-4H-chromen-2-yl)-3-morpholinophenoxy)ethoxy)cyclobutanecarboxylic acid (9 mg, 9.14% yield) as a yellow foam.

Example 60: $^1$H NMR (DMSO-d$_6$, 400 MHz): δ ppm 7.96-8.03 (m, 2H), 7.71-7.75 (m, 1H), 7.45-7.52 (m, 1H), 7.15 (s, 1H), 6.78-6.85 (m, 1H), 6.68-6.74 (m, 1H), 4.12-

4.22 (m, 2H), 3.73-3.95 (m, 1H), 3.61-3.72 (m, 6H), 2.93-3.03 (m, 4H), 2.56-2.63 (m, 1H), 2.36-2.47 (m, 2H), 2.16 (m, 1H), 1.94-2.04 (m, 1H). MS obsd. (ESI$^+$) [(M+H)$^+$]: 500.1.

Example 61

2-[2-[4-(8-chloro-4-oxo-chromen-2-yl)phenoxy]ethoxy]acetamide

61

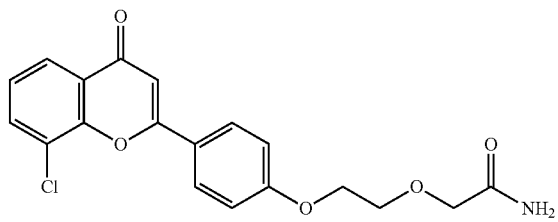

To a solution of 2-[2-[4-(8-chloro-4-oxo-chromen-2-yl)phenoxy]ethoxy]acetic acid (example 9, 400.0 mg, 1.07 mmol), triethylamine (0.6 mL, 4.27 mmol) in THF (20 mL) was added HATU (486.99 mg, 1.28 mmol), ammonium chloride (114.2 mg, 2.13 mmol). The mixture was stirred at room temperature for 12 hours. The mixture was then washed by water (15 mL) and concentrated in vacuo. The residue was then triturated in DMF (15 mL) and the suspension was then filtered to give 2-[2-[4-(8-chloro-4-oxo-chromen-2-yl)phenoxy]ethoxy]acetamide (75 mg, 16.8%) as a yellow solid. $^1$H NMR (DMSO-d$_6$, 400 MHz): δ ppm 8.10 (d, J=8.9 Hz, 2H), 8.00 (d, J=7.9 Hz, 2H), 7.49 (t, J=7.8 Hz, 1H), 7.27 (d, J=7.7 Hz, 1H), 7.19 (d, J=9.0 Hz, 2H), 7.07 (s, 1H), 4.21-4.32 (m, 2H), 3.90 (s, 2H), 3.81-3.86 (m, 2H). MS obsd. (ESI$^+$) [(M+H)$^+$]:374.1.

Example 62

Methyl 3-[2-[4-[8-chloro-6-fluoro-4-oxo-3-(trifluoromethoxy)chromen-2-yl]phenoxy]ethoxy]cyclobutanecarboxylate

62

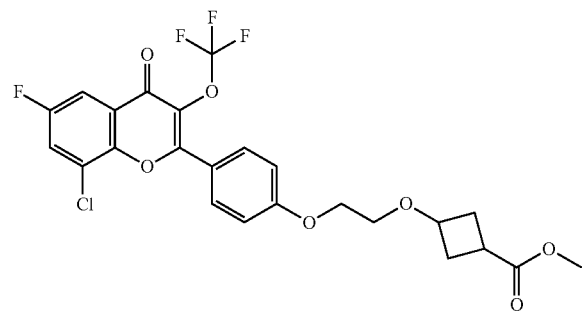

Step 1: Preparation of methyl 3-[2-[4-(8-chloro-6-fluoro-4-oxo-chromen-2-yl)phenoxy]ethoxy]cyclobutanecarboxylate 62a

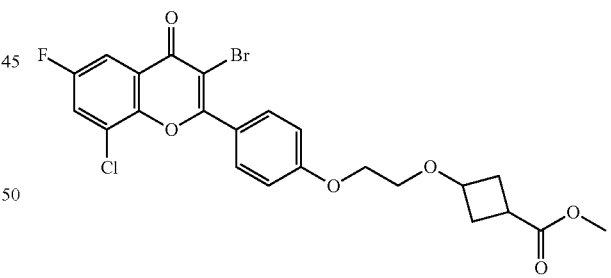

Compound 62a was prepared in analogy to the procedure described for the preparation of compound 15f by using 1-(3-chloro-5-fluoro-2-hydroxy-phenyl)ethanone as the starting materials instead of 1-(3-chloro-4-fluoro-2-hydroxy-phenyl)ethanone in Step 3.

Step 2: Preparation of methyl 3-[2-[4-(3-bromo-8-chloro-6-fluoro-4-oxo-chromen-2-yl)phenoxy]ethoxy]cyclobutanecarboxylate 62b To a mixture of methyl 3-[2-[4-(8-chloro-6-fluoro-4-oxo-chromen-2-yl)phenoxy]ethoxy]cyclobutanecarboxylate (0.6 g, 1.34 mmol) in DCM (10 mL) was added Py (1 mL) and PyHBr$_3$ (2.15 g, 6.71 mmol) and the mixture was stirred at room temperature for 16 hours. The reaction was quenched with water (30 mL) and the resulting mixture was extracted with DCM (50 mL) twice. The combined organic phase was dried over MgSO$_4$ and concentrated in vacuo to give the crude of methyl 3-[2-[4-(3-bromo-8-chloro-6-fluoro-4-oxo-chromen-2-yl)phenoxy]ethoxy]cyclobutanecarboxylate (0.5 g, 70.8%) as a yellow solid, which was used in the next step directly. MS obsd. (ESI$^+$) [(M+H)$^+$]: 525.8.

Step 3: Preparation of 3-[2-[4-(8-chloro-6-fluoro-3-hydroxy-4-oxo-chromen-2-yl)phenoxy]ethoxy]cyclobutanecarboxylic acid

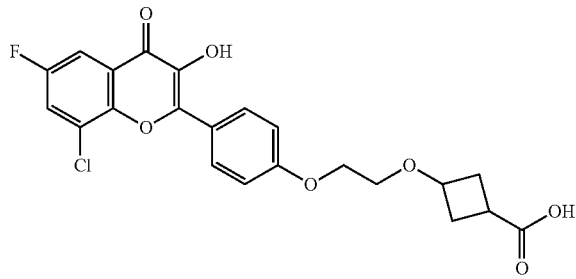

62c

To a solution of methyl 3-[2-[4-(3-bromo-8-chloro-6-fluoro-4-oxo-chromen-2-yl)phenoxy]ethoxy]cyclobutanecarboxylate (500 mg, 0.95 mmol) in DMF (5 mL) was added NaOH solution (4N, 5 mL) and the mixture was then stirred at 80° C. for 2 hours. The mixture was poured into water (30 mL) and adjusted to pH=5-6 by addition of conc. HCl. The resulting mixture was extracted with EtOAc (50 mL) twice and the combined organic phase was dried over $Na_2SO_4$, concentrated in vacuo to give the crude of 3-[2-[4-(8-chloro-6-fluoro-3-hydroxy-4-oxo-chromen-2-yl)phenoxy]ethoxy]cyclobutanecarboxylic acid (0.3 g, 68.5% yield) as a yellow solid, which was used in the next step directly. MS obsd. (ESI$^+$) [(M+H)$^+$]: 449.1.

Step 4: Preparation of methyl 3-[2-[4-(8-chloro-6-fluoro-3-hydroxy-4-oxo-chromen-2-yl)phenoxy]ethoxy]cyclobutanecarboxylate

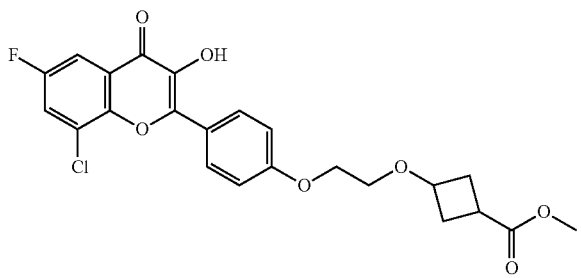

62d

A solution of 3-[2-[4-(8-chloro-6-fluoro-3-hydroxy-4-oxo-chromen-2-yl)phenoxy]ethoxy]cyclobutanecarboxylic acid (0.3 g, 0.65 mmol) dissolved in hydrogen chloride methanol solution (4 mol/L, 7.5 ml, 30 mmol) was stirred at room temperature for 12 hours. After the reaction was completed, the mixture was concentrated in vacuo to give methyl 3-[2-[4-(8-chloro-6-fluoro-3-hydroxy-4-oxo-chromen-2-yl)phenoxy]ethoxy]cyclobutanecarboxylate (0.3 g, 100% yield) as a white solid, which was used in the next step directly without further purification. MS obsd. (ESI$^+$) [(M+H)$^+$]: 463.2.

Step 5: Preparation of methyl 3-[2-[4-[3-[bromo(difluoro)methoxy]-8-chloro-6-fluoro-4-oxo-chromen-2-yl]phenoxy]ethoxy]cyclobutanecarboxylate

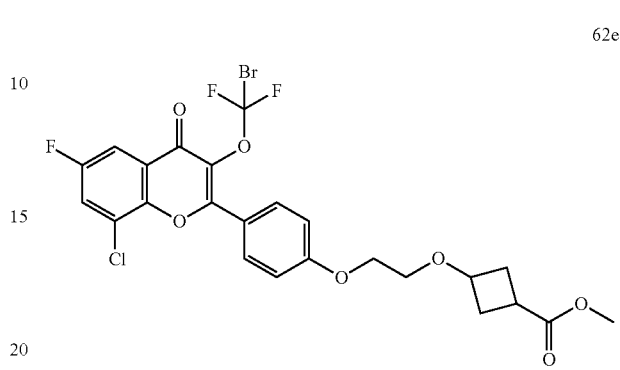

62e

To a solution of methyl 3-[2-[4-(8-chloro-6-fluoro-3-hydroxy-4-oxo-chromen-2-yl)phenoxy]ethoxy]cyclobutanecarboxylate (200 mg, 0.43 mmol) in NMP (5 mL) was added sodium hydride (34.57 mg, 0.860 mmol) at 0° C., the mixture was then stirred at 0° C. for 30 minutes. Then to the resulting mixture was added dibromo(difluoro)methane (0.075 mL, 0.86 mmol, 2 eq) and the mixture was stirred at room temperature for 36 hours. The mixture was quenched with saturated NH$_4$Cl solution (5 mL) and extracted with EtOAc (10 mL) three times. The organic phase was combined, washed with brine, dried over Na$_2$SO$_4$ and concentrated in vacuo. The residue was re-dissolved in MeOH (2 mL) and the mixture was then filtered. The filtrate was concentrated in vacuo to give the crude of methyl 3-[2-[4-[3-[bromo(difluoro)methoxy]-8-chloro-6-fluoro-4-oxo-chromen-2-yl]phenoxy]ethoxy]cyclobutanecarboxylate (20 mg, 8.01%) as yellow solid. MS obsd. (ESI$^+$) [(M+H)$^+$]: 592.1.

Step 6: Preparation of methyl 3-[2-[4-[8-chloro-6-fluoro-4-oxo-3-(trifluoromethoxy)chromen-2-yl]phenoxy]ethoxy]cyclobutanecarboxylate

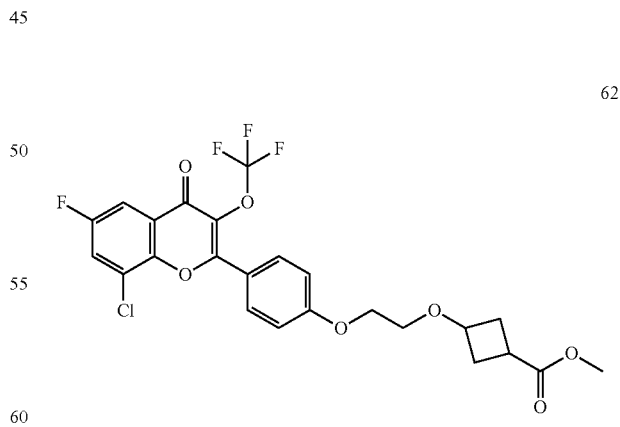

62

To a solution of methyl 3-[2-[4-[3-[bromo(difluoro)methoxy]-8-chloro-6-fluoro-4-oxo-chromen-2-yl]phenoxy]ethoxy]cyclobutanecarboxylate (40.0 mg, 0.070 mmol, 1 eq) in DCM (2 mL) cooled at −70° C. was added argentio(tetrafluoro)boron (32.9 mg, 0.170 mmol, 2.5 eq) and the mixture was stirred at 15° C. for 12 hours. The mixture was filtered and the filtrate was concentrated in vacuo to give the crude of methyl 3-[2-[4-[8-chloro-6-fluoro-4-oxo-3-(trifluoromethoxy)chromen-2-yl]phenoxy]ethoxy]cyclobutanecarboxylate, which was further purified by Prep-HPLC to give two diastereomers with cis- and trans-configuration, one of which is characterized as Example 62-A (4.8 mg, 12.8%) and the other is Example 62-B (5.2 mg, 14.3%). as white solid.

Example 62-A: ¹H NMR (CDCl₃, 400 MHz): δ ppm 8.15 (d, J=9.03 Hz, 2H), 7.31-7.40 (m, 2H), 7.06 (d, J=8.91 Hz, 2H), 4.32 (t, J=6.78 Hz, 1H), 4.19-4.26 (m, 2H), 3.74-3.83 (m, 2H), 3.71 (s, 3H), 3.01-3.13 (m, 1H), 2.54-2.57 (m, 2H), 2.30-2.34 (m, 2H). MS obsd. (ESI⁺) [(M+H)⁺]: 531.1.

Example 62-B: ¹H NMR (CDCl₃, 400 MHz): δ ppm 8.15 (d, J=9.03 Hz, 2H), 7.30-7.38 (m, 2H), 7.06 (d, J=8.93 Hz, 2H), 4.22 (t, J=4.65 Hz, 1H), 4.02 (m, 2H), 3.73-3.83 (m, 2H), 3.70 (s, 3H), 2.60-2.75 (m, 1H), 2.55-2.65 (m, 2H), 2.24-2.36 (m, 2H). MS obsd. (ESI⁺) [(M+H)⁺]: 531.1.

Example 63

3-[2-[4-[8-chloro-6-fluoro-4-oxo-3-(trifluoromethoxy)chromen-2-yl]phenoxy]ethoxy]cyclobutanecarboxylic acid

63

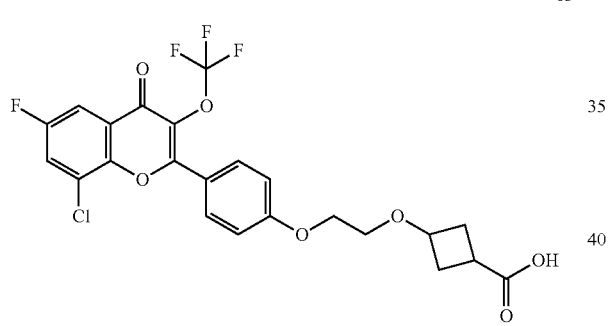

To a mixture of methyl 3-[2-[4-[8-chloro-6-fluoro-4-oxo-3-(trifluoromethoxy)chromen-2-yl]phenoxy]ethoxy]cyclobutanecarboxylate (100 mg, 0.19 mmol) in the mixed solvent of THF (5 mL) and water (2 mL) was added lithium hydroxide (48 mg, 2 mmol) and the mixture was then stirred at room temperature for 12 hours. The mixture was adjusted to pH~4 by addition of 1M HCl and extracted with EtOAc (10 mL) three times. The combined organic layer was washed with brine, dried over Na₂SO₄ and concentrated in vacuo. The residue was purified by preparative HPLC to give 3-[2-[4-[8-chloro-6-fluoro-4-oxo-3-(trifluoromethoxy)chromen-2-yl]phenoxy]ethoxy]cyclobutanecarboxylic acid (17.3 mg, 17.7% yield) as a white solid. ¹H NMR (DMSO-d₆, 400 MHz): δ ppm 8.07 (d, J=9.2 Hz, 2H), 7.90-7.93 (m, 1H), 7.77-7.79 (m, 1H), 7.19 (d, J=8.8 Hz, 2H), 4.20-4.32 (m, 2H), 3.90-4.15 (m, 1H), 3.67-3.69 (m, 2H), 2.80-2.99 (m, 1H), 2.40-2.50 (m, 2H), 2.11-2.23 (m, 1H), 1.95-2.04 (m, 1H). MS obsd. (ESI⁺) [(M+H)⁺]: 517.1.

Example 64

3-[2-[4-(3-bromo-8-chloro-4-oxo-chromen-2-yl)phenoxy]ethoxy]cyclobutanecarboxylic acid

64

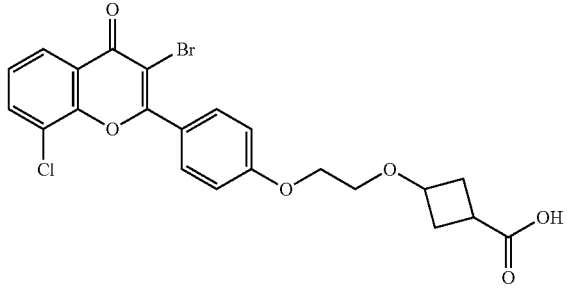

Step 1: Preparation of ethyl 3-[2-[4-(3-bromo-8-chloro-4-oxo-chromen-2-yl)phenoxy]ethoxy]cyclobutanecarboxylate 64a

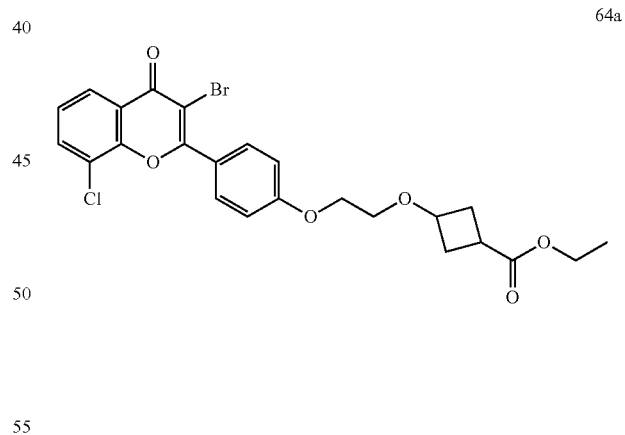

To a solution of ethyl 3-(2-(4-(8-chloro-4-oxo-4H-chromen-2-yl)phenoxy)ethoxy)cyclobutanecarboxylate (200 mg, 452 µmol) in DCM (5 mL) was added 1-bromopyrrolidine-2,5-dione (88.4 mg, 497 µmol), the mixture was then stirred at room temperature for 5 hours. The mixture was then concentrated in vacuo and purified by column chromatography on silica gel (elution with DCM:MeOH 100:1-10:1) to give ethyl 3-[2-[4-(3-bromo-8-chloro-4-oxo-chromen-2-yl)phenoxy]ethoxy]cyclobutanecarboxylate (30 mg, 12.7% yield) as a yellow solid. MS obsd. (ESI⁺) [(M+H)⁺]: 520.9.

Step 2: Preparation of 3-[2-[4-(3-bromo-8-chloro-4-oxo-chromen-2-yl)phenoxy]ethoxy]cyclobutanecarboxylic acid

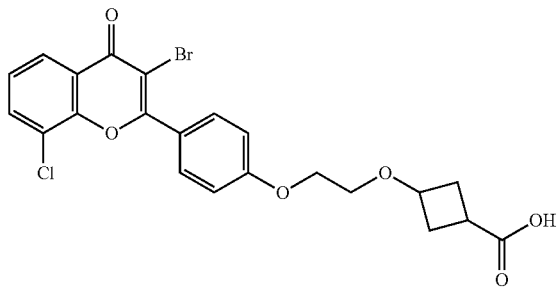

64

To a solution of ethyl 3-(2-(4-(3-bromo-8-chloro-4-oxo-4H-chromen-2-yl)phenoxy)ethoxy)cyclobutanecarboxylate (30 mg, 57.5 μmol) in the mixed solvent of THF (1 mL) and H$_2$O (0.5 mL) was added LiOH (6.88 mg, 287 μmol) and the mixture was then stirred at room temperature for 1 hour. After the reaction was completed, the mixture was adjusted to pH~6 by addition of HCl (1 N) and concentrated in vacuo. The residue was purified by preparative HPLC to give 3-[2-[4-(3-bromo-8-chloro-4-oxo-chromen-2-yl)phenoxy]ethoxy]cyclobutanecarboxylic acid (3.6 mg, 12.6%) as a light yellow solid. $^1$H NMR (DMSO-d$_6$, 400 MHz): δ ppm 8.06 (m, 2H), 7.93 (d, J=9.05 Hz, 2H), 7.55 (s, 1H), 7.19 (d, J=9.05 Hz, 2H), 4.15-4.24 (m, 2H), 3.91-4.02 (m, 1H), 3.60-3.72 (m, 2H), 2.56-2.63 (m, 1H), 2.40-2.51 (m, 2H), 1.90-2.08 (m, 2H). MS obsd. (ESI$^+$) [(M+H)$^+$]: 492.9.

Example 65

3-[2-[4-(3-benzyloxy-8-chloro-4-oxo-chromen-2-yl)phenoxy]ethoxy]cyclobutanecarboxylic acid

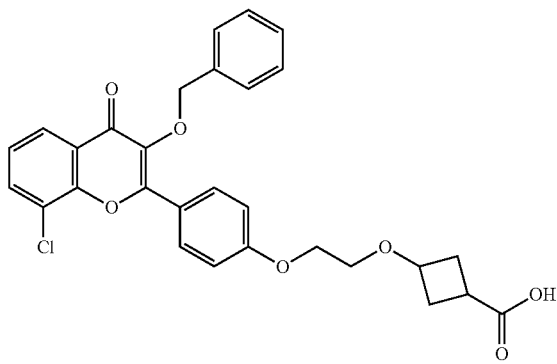

65

To a solution of 3-(2-(4-(8-chloro-3-hydroxy-4-oxo-4H-chromen-2-yl)phenoxy)ethoxy)cyclobutanecarboxylic acid (30 mg, 69.6 μmol) and Cs2CO3 (56.7 mg, 174 μmol) in DMF (3 mL) was added (bromomethyl)benzene (26.2 mg, 153 μmol) and the mixture was then stirred at room temperature overnight. Then to the reaction was added LiOH (24 mg, 1 mmol) and the mixture was stirred at 50° C. for 1 hour. The mixture was adjusted to pH~6 by addition of HCl (1 N) and concentrated in vacuo. The residue was purified by preparative HPLC to give 3-[2-[4-(3-benzyloxy-8-chloro-4-oxo-chromen-2-yl)phenoxy]ethoxy]cyclobutanecarboxylic acid (18 mg, 45.7%) as a light yellow solid. $^1$H NMR (DMSO-d$_6$, 400 MHz): δ ppm 7.93-8.14 (m, 4H), 7.50 (s, 1H), 7.28-7.44 (m, 5H), 7.14 (d, J=9.05 Hz, 2H), 5.11 (s, 2H), 4.15-4.24 (m, 2H), 3.90-3.99 (m, 1H), 3.57-3.73 (m, 2H), 2.55-2.63 (m, 1H), 2.40-2.51 (m, 2H), 1.88-2.09 (m, 2H). MS obsd. (ESI$^+$) [(M+H)$^+$]: 521.1.

Example 66

3-[2-[4-[8-chloro-4-oxo-6-(trifluoromethyl)chromen-2-yl]phenoxy]ethoxy]cyclobutanecarboxylic acid

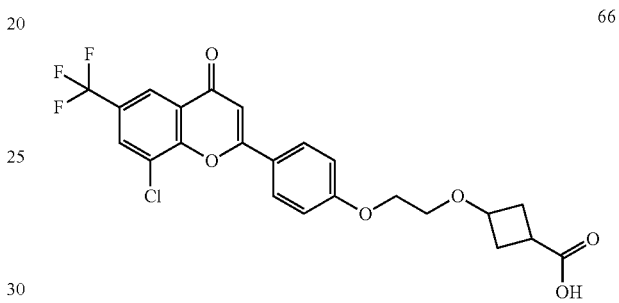

66

Step 1: Preparation of 6-bromo-8-chloro-2-(4-hydroxyphenyl)chromen-4-one

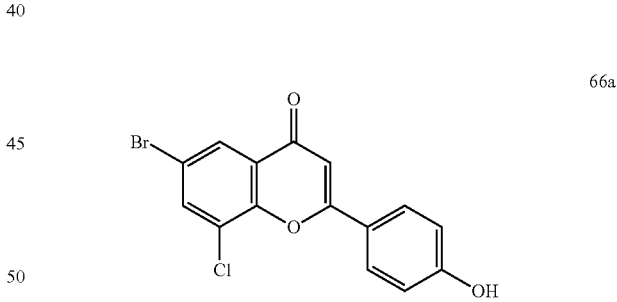

66a

To a solution of 6-bromo-8-chloro-2-(4-methoxyphenyl)chromen-4-one (intermediate 22b, 5.0 g, 13.68 mmol) in chloroform (20 mL) cooled at 0° C. was added BBr$_3$ (17.13 g, 68.3 mmol). The mixture was then stirred at room temperature for 16 hours. After the reaction was completed, the reaction mixture was quenched with water (50 mL) and the resulting suspension was filtered and the solid was washed by water (200 mL) and EtOH (100 mL) in sequence. The solid was concentrated in vacuo to give the crude product of 6-bromo-8-chloro-2-(4-hydroxyphenyl)chromen-4-one (4.3 g, 71.55% yield) as a yellow solid, which was used in the next step directly without further purification. MS obsd. (ESI$^+$) [(M+H)$^+$]: 351.6.

Step 2: Preparation of methyl 3-[2-[4-(6-bromo-8-chloro-4-oxo-chromen-2-yl)phenoxy]ethoxy]cyclobutanecarboxylate

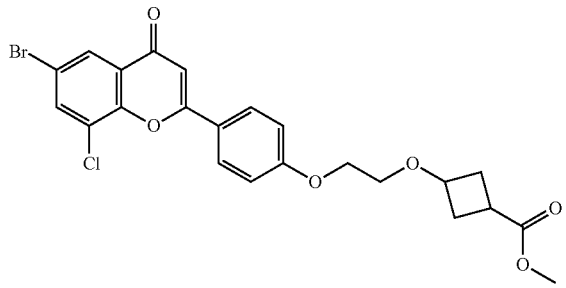

66b

To a solution of 6-bromo-8-chloro-2-(4-hydroxyphenyl)chromen-4-one (4.3 g, 13.56 mmol) and potassium carbonate (3.75 g, 27.12 mmol) in DMF (30 mL) was added methyl 3-[2-(p-tolylsulfonyloxy)ethoxy]cyclobutanecarboxylate (int-2. 4.45 g, 13.56 mmol) and the mixture was then stirred at 80° C. for 16 hours. The reaction mixture was filtered and the filtrate was concentrated in vacuo. The residue was purified by column chromatography on silica gel (eluent DCM:MeOH=30:1~10:1) to give the methyl 3-[2-[4-(6-bromo-8-chloro-4-oxo-chromen-2-yl)phenoxy]ethoxy]cyclobutanecarboxylate (4.5 g, 63.11% yield) as a yellow solid. MS obsd. (ESI$^+$) [(M+H)$^+$]: 507.8.

Step 3: Preparation of methyl 3-[2-[4-[8-chloro-4-oxo-6-(trifluoromethyl)chromen-2-yl]phenoxy]ethoxy]cyclobutanecarboxylate

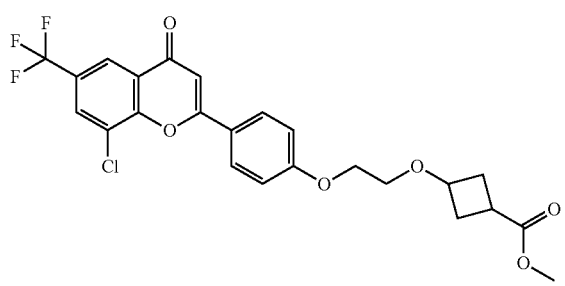

66c

To a solution of copper(I) iodide (0.13 mL, 3.94 mmol) and sodium trifluoroacetate (1.07 g, 7.88 mmol) in NMP (10 mL) was added methyl 3-[2-[4-(6-bromo-8-chloro-4-oxo-chromen-2-yl)phenoxy]ethoxy]cyclobutanecarboxylate (400 mg, 0.79 mmol) and the mixture was stirred at 160° C. under nitrogen atmosphere for 4 hours. After the reaction was completed, the mixture was filtered and the filtrate was purified by preparative HPLC to give the crude of methyl 3-[2-[4-[8-chloro-4-oxo-6-(trifluoromethyl)chromen-2-yl]phenoxy]ethoxy]cyclobutanecarboxylate (230 mg, 52.89% yield) as brown oil. MS obsd. (ESI$^+$) [(M+H)$^+$]: 496.8.

Step 4: Preparation of 3-[2-[4-[8-chloro-4-oxo-6-(trifluoromethyl)chromen-2-yl]phenoxy]ethoxy]cyclobutanecarboxylic acid

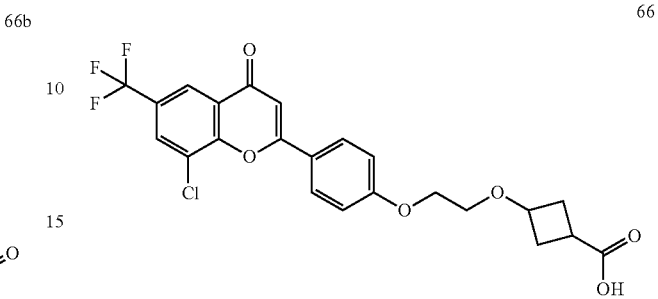

66

To a solution of methyl 3-[2-[4-[8-chloro-4-oxo-6-(trifluoromethyl)chromen-2-yl]phenoxy]ethoxy]cyclobutanecarboxylate (230 mg, 0.46 mmol, 1 eq) in the mixed solvent of THF (3 mL), methanol (3 mL) and water (3 mL) was added lithium hydroxide (0.03 mL, 3.32 mmol) and the mixture was then stirred at room temperature for 2 hours. After the reaction was completed, the mixture was concentrated in vacuo and the residue was purified by preparative HPLC to give [2-[4-[8-chloro-4-oxo-6-(trifluoromethyl)chromen-2-yl]phenoxy]ethoxy]cyclobutanecarboxylic acid (150 mg, 44.44% yield) as a yellow solid. The solid was further purified by supercritical fluid chromatography (SFC) to give two diastereomers with cis- and trans-configuration, one of which is characterized as Example 66-A (55.3 mg, 36.2%) and the other is Example 66-B (54.6 mg, 34.1%). as white solid.

Example 66-A: $^1$H NMR (DMSO-d$_6$, 400 MHz): δ ppm 8.41 (m, 1H), 8.15 (m 1H), 8.04 (d, J=8.2 Hz, 2H), 7.18-7.07 (m, 3H), 4.24-4.15 (m, 3H), 3.65 (m, 2H), 2.82 (t, J=10.0 Hz, 1H), 2.43-2.31 (m, 2H), 2.14-2.05 (m, 2H). MS obsd. (ESI$^+$) [(M+H)$^+$]: 482.9.

Example 66-B: $^1$H NMR (DMSO-d$_6$, 400 MHz): δ ppm 8.39 (m, 1H), 8.13 (m, 1H), 8.02 (d, J=7.9 Hz, 2H), 7.17-7.07 (m, 3H), 4.16 (m, 2H), 3.96-3.84 (m, 1H), 3.65 (br s, 2H), 2.45-2.30 (m, 3H), 2.06-1.95 (m, 2H). MS obsd. (ESI$^+$) [(M+H)$^+$]: 482.9.

Example 67

3-[2-[4-(8-chloro-6-cyclopropyl-4-oxo-chromen-2-yl)phenoxy]ethoxy]cyclobutanecarboxylic acid

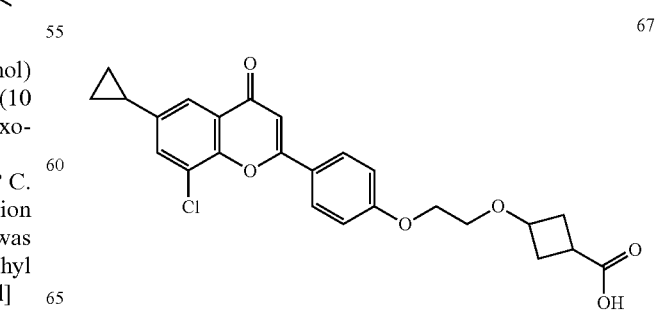

67

Step 1: Preparation of methyl 3-[2-[4-(8-chloro-6-cyclopropyl-4-oxo-chromen-2-yl)phenoxy]ethoxy]cyclobutanecarboxylate

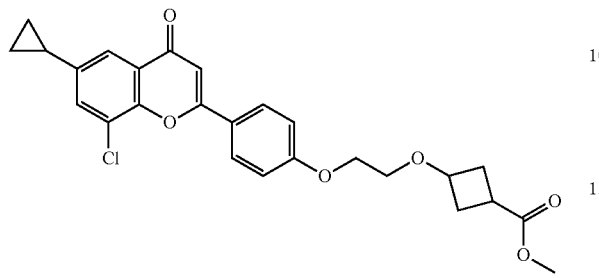

67a

To a solution of methyl 3-[2-[4-(6-bromo-8-chloro-4-oxo-chromen-2-yl)phenoxy]ethoxy]cyclobutanecarboxylate (500 mg, 0.980 mmol), tricyclohexyl phosphine (27.61 mg, 0.100 mmol), cyclopropylboronic acid (110 mg, 1.28 mmol) and phosphoric acid, potassium salt (0.24 mL, 2.95 mmol) in the mixed solvent of toluene (10 mL) and water (1 mL) was added palladium (II) acetate (11.0 mg, 0.050 mmol). The mixture was then stirred at 100° C. for 12 hours under N₂ atmosphere. After the reaction was completed, the mixture was concentrated in vacuo and the residue was purified by column chromatography on silica gel (elution with PE:EtOAc 2:1) to give methyl 3-[2-[4-(8-chloro-6-cyclopropyl-4-oxo-chromen-2-yl)phenoxy]ethoxy]cyclobutanecarboxylate (300 mg, 58.47% yield) as a yellow oil.

Step 2: Preparation of 3-[2-[4-(8-chloro-6-cyclopropyl-4-oxo-chromen-2-yl)phenoxy]ethoxy]cyclobutanecarboxylic acid

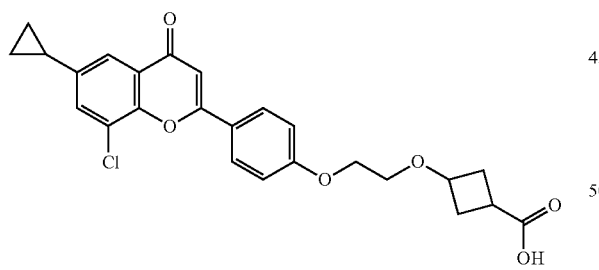

67

To a solution of methyl 3-[2-[4-(8-chloro-6-cyclopropyl-4-oxo-chromen-2-yl)phenoxy]ethoxy]cyclobutanecarboxylate (400 mg, 0.85 mmol) in THF (5 mL)/methanol (5 mL)/water (1 mL) was added lithium hydroxide (0.04 mL, 4.27 mmol). The mixture was stirred at room temperature for 2 hours. After the reaction was completed, the mixture was concentrated in vacuo and the residue was purified by preparative HPLC to give 3-[2-[4-(8-chloro-6-cyclopropyl-4-oxo-chromen-2-yl)phenoxy]ethoxy]cyclobutanecarboxylic acid (119.5 mg, 30.74% yield) as a white solid. ¹H NMR (DMSO-d₆, 400 MHz): δ ppm 12.19 (br s, 1H), 8.08-8.00 (m, 2H), 7.69 (s, 1H), 7.64 (s, 1H), 7.15 (d, J=8.5 Hz, 2H), 7.00 (d, J=1.4 Hz, 1H), 4.22-3.91 (m, 3H), 3.72-3.62 (m, 2H), 2.97-2.56 (m, 1H), 2.47-2.32 (m, 2H), 2.22-1.94 (m, 3H), 1.08-0.99 (m, 2H), 0.84-0.75 (m, 2H). MS obsd. (ESI⁺) [(M+H)⁺]: 455.0.

Example 68

3-[2-[4-[8-chloro-4-oxo-6-(2-oxopyrrolidin-1-yl)chromen-2-yl]phenoxy]ethoxy]cyclobutanecarboxylic acid

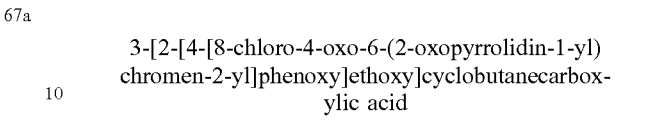

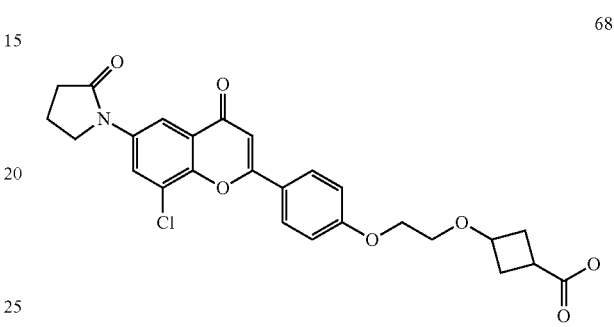

68

Step 1: Preparation of methyl 3-[2-[4-[8-chloro-4-oxo-6-(2-oxopyrrolidin-1-yl)chromen-2-yl]phenoxy]ethoxy]cyclobutanecarboxylate

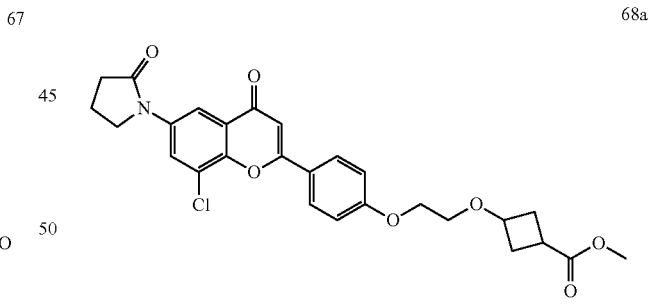

68a

To a mixture of methyl 3-[2-[4-(6-bromo-8-chloro-4-oxo-chromen-2-yl)phenoxy]ethoxy]cyclobutanecarboxylate (300 mg, 0.59 mmol), 2-pyrrolidone (0.8 mL, 10.58 mmol), cesium carbonate (192.5 mg, 0.59 mmol) in 1,4-dioxane (10 mL) was added tBuXPhos PD G3 (46.9 mg, 0.060 mmol) and the reaction was then stirred at 90° C. for 12 hours under N₂ atmosphere. After the reaction was completed, the mixture was filtered and filtrate was concentrated in vacuo. The residue was purified by column chromatography on silica gel (elution with PE:EtOAc 10:1-2:1) to give methyl 3-[2-[4-[8-chloro-4-oxo-6-(2-oxopyrrolidin-1-yl)chromen-2-yl]phenoxy]ethoxy]cyclobutanecarboxylate (130 mg, 17.19% yield) as a yellow solid. MS obsd. (ESI⁺) [(M+H)⁺]: 511.9.

Step 2: Preparation of 3-[2-[4-[8-chloro-4-oxo-6-(2-oxopyrrolidin-1-yl)chromen-2-yl]phenoxy]ethoxy]cyclobutanecarboxylic acid

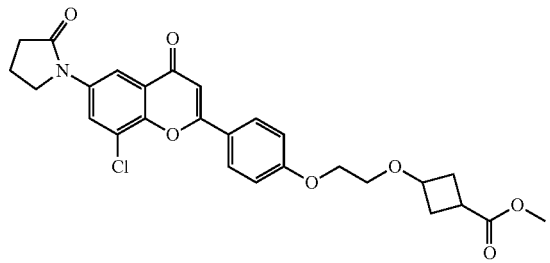

68

To a solution of methyl 3-[2-[4-[8-chloro-4-oxo-6-(2-oxopyrrolidin-1-yl)chromen-2-yl]phenoxy]ethoxy]cyclobutanecarboxylate (110 mg, 0.21 mmol) in the mixed solvent of THF (6 mL) and water (2 mL) was added lithium hydroxide (25.6 mg, 1.07 mmol) and the mixture was stirred at room temperature for 12 hours. After the reaction was completed, the mixture was adjusted to pH=6 by addition of AcOH and the resulting mixture was concentrated in vacuo, the residue was purified by preparative HPLC to give the 3-[2-[4-[8-chloro-4-oxo-6-(2-oxopyrrolidin-1-yl)chromen-2-yl]phenoxy]ethoxy]cyclobutanecarboxylic acid (27 mg, 0.050 mmol, 25.24% yield) as a yellow solid. $^1$H NMR (DMSO-$d_6$, 400 MHz): δ ppm 12.2 (br s, 1H), 8.44 (s, 1H), 8.06-8.09 (m, 3H), 7.16-7.18 (m, 2H), 7.04 (s, 1H), 4.12-4.20 (m, 2H), 3.90-3.96 (m, 2H), 3.66-3.69 (m, 2H), 2.65-2.86 (m, 1H), 2.51-2.58 (m, 3H), 2.28-2.41 (m, 2H), 1.90-2.15 (m, 4H). MS obsd. (ESI$^+$) [(M+H)$^+$]: 498.1.

Example 69

3-[2-[4-[8-chloro-4-oxo-7-(trifluoromethyl)chromen-2-yl]phenoxy]ethoxy]cyclobutanecarboxylic acid

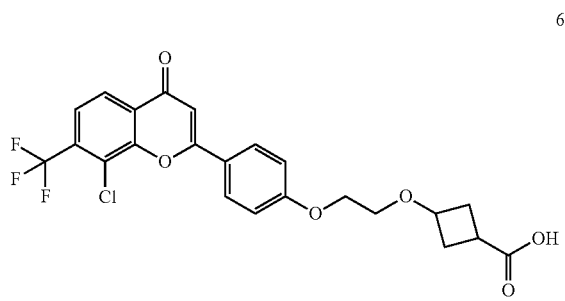

69

Step 1: Preparation of 7-bromo-8-chloro-2-(4-hydroxyphenyl)chromen-4-one

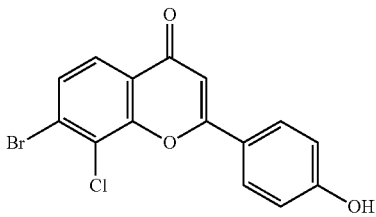

69a

Compound 69a was prepared in analogy to the procedure described for the preparation of compound 66a by using 7-bromo-8-chloro-2-(4-methoxyphenyl)chromen-4-one as the starting materials instead of 6-bromo-8-chloro-2-(4-methoxyphenyl)chromen-4-one in Step 1.

Step 2: Preparation of methyl 3-[2-[4-(7-bromo-8-chloro-4-oxo-chromen-2-yl)phenoxy]ethoxy]cyclobutanecarboxylate

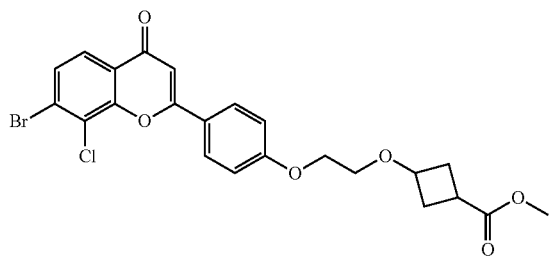

69b

Compound 69b was prepared in analogy to the procedure described for the preparation of compound 66b by using 7-bromo-8-chloro-2-(4-hydroxyphenyl)chromen-4-one as the starting materials instead of 6-bromo-8-chloro-2-(4-hydroxyphenyl)chromen-4-one in Step 2.

Step 3: Preparation of 3-[2-[4-[8-chloro-4-oxo-7-(trifluoromethyl)chromen-2-yl]phenoxy]ethoxy]cyclobutanecarboxylic acid

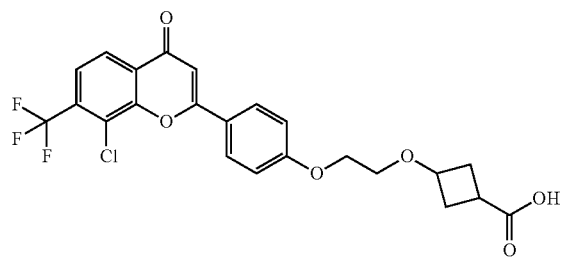

69

Example 69 was prepared in analogy to the procedure described for the preparation of example 66 by using methyl 3-[2-[4-(7-bromo-8-chloro-4-oxo-chromen-2-yl)phenoxy]

ethoxy]cyclobutanecarboxylate as the starting materials instead of methyl 3-[2-[4-(6-bromo-8-chloro-4-oxo-chromen-2-yl)phenoxy]ethoxy]cyclobutanecarboxylate in Step 3.

Example 69: $^1$H NMR (DMSO-d$_6$, 400 MHz): δ ppm 8.05-8.17 (m, 3H), 7.83-7.95 (m, 1H), 7.14-7.23 (m, 3H), 4.13-4.25 (m, 3H), 3.62-3.71 (m, 2H), 2.87-2.97 (m, 1H), 2.39 (m, 2H), 2.10-2.22 (m, 2H). MS obsd. (ESI$^+$) [(M+H)$^+$]: 482.9.

Example 70

3-[2-[4-(8-chloro-7-cyclopropyl-4-oxo-chromen-2-yl)phenoxy]ethoxy]cyclobutanecarboxylic acid

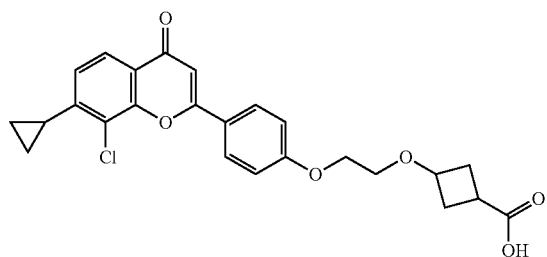

Example 70 was prepared in analogy to the procedure described for the preparation of example 67 by using methyl 3-[2-[4-(7-bromo-8-chloro-4-oxo-chromen-2-yl)phenoxy]ethoxy]cyclobutanecarboxylate as the starting materials instead of methyl 3-[2-[4-(6-bromo-8-chloro-4-oxo-chromen-2-yl)phenoxy]ethoxy]cyclobutanecarboxylate in Step 1. The solid of 3-[2-[4-(8-chloro-7-cyclopropyl-4-oxo-chromen-2-yl)phenoxy]ethoxy]cyclobutanecarboxylic acid (130 mg, mmol) was further purified by supercritical fluid chromatography (SFC) to give two diastereomers with cis- and trans-configuration, one of which is characterized as Example 70-A (45 mg, 17.8%) and the other is Example 70-B (30 mg, 27.7%) as white solid.

Example 70: $^1$H NMR (DMSO-d$_6$, 400 MHz): δ ppm 12.19 (br s, 1H), 8.09 (d, J=8.9 Hz, 2H), 7.90-7.83 (m, 1H), 7.18 (d, J=8.9 Hz, 2H), 7.08 (d, J=8.4 Hz, 1H), 7.02 (s, 1H), 4.14-4.22 (m, 2H), 3.87-4.11 (m, 1H), 3.64-3.71 (m, 2H), 2.86-2.96 (m, 1H), 2.56-2.67 (m, 1H), 2.37-2.43 (m, 2H), 2.12-2.20 (m, 1H), 1.95-2.05 (m, 1H), 1.24-1.14 (m, 2H), 0.95-0.86 (m, 2H). MS obsd. (ESI$^+$) [(M+H)$^+$]: 455.1.

Example 70-A: $^1$H NMR (DMSO-d$_6$, 400 MHz): δ ppm 8.18-8.02 (m, 2H), 7.77-7.95 (m, 1H), 7.17 (d, J=8.9 Hz, 2H), 7.08 (d, J=8.4 Hz, 1H), 7.01 (s, 1H), 4.12-4.24 (m, 3H), 3.63-3.72 (m, 2H), 2.88-2.92 (m, 1H), 2.35-2.43 (m, 3H), 2.11-2.21 (m, 1H), 1.15-1.22 (m, 2H), 0.87-0.93 (m, 2H). MS obsd. (ESI$^+$) [(M+H)$^+$]: 455.1.

Example 70-B: $^1$H NMR (DMSO-d$_6$, 400 MHz): δ ppm 8.10 (d, J=8.9 Hz, 2H), 7.87 (d, J=8.4 Hz, 1H), 7.18 (d, J=9.0 Hz, 2H), 7.09 (d, J=8.4 Hz, 1H), 7.02 (s, 1H), 4.13-4.23 (m, 2H), 3.89-4.03 (m, 1H), 3.63-3.73 (m, 2H), 2.55-2.62 (m, 1H), 2.36-2.44 (m, 3H), 1.90-2.05 (m, 2H), 1.13-1.24 (m, 2H), 0.87-0.95 (m, 2H). MS obsd. (ESI$^+$) [(M+H)$^+$]: 455.1.

Example 71 ethyl 2-[2-[4-(7-bromo-8-chloro-4-oxo-chromen-2-yl)phenoxy]ethoxy]acetate

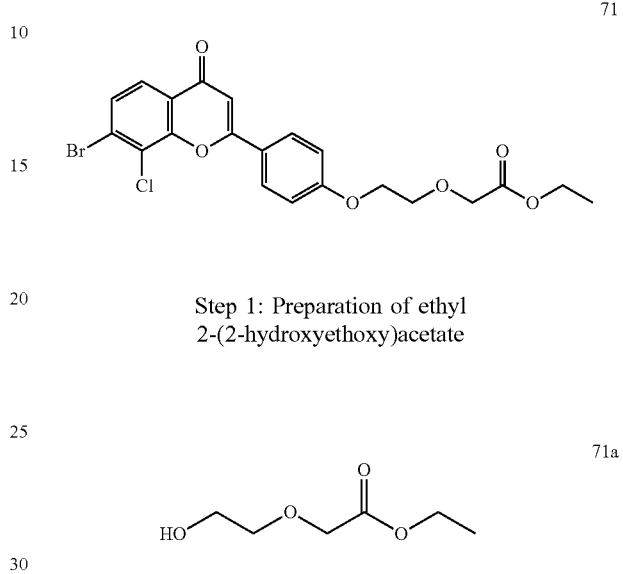

Step 1: Preparation of ethyl 2-(2-hydroxyethoxy)acetate

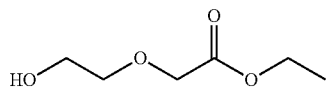

To a solution of ethyl 2-(2-benzyloxyethoxy)acetate (2.0 g, 8.39 mmol) in ethanol (20 mL) was added palladium hydroxide (1.18 g, 8.39 mmol) and the mixture was then hydrogenated under H$_2$ atmosphere at room temperature overnight. After the reaction was completed, the reaction was filtered through silica gel pad and the filtrate was concentrated in vacuo to give ethyl 2-(2-hydroxyethoxy) acetate (1.1 g, 7.42 mmol, 44.23% yield) as a colorless oil.

Step 2: Preparation of ethyl 2-[2-(p-tolylsulfonyloxy)ethoxy]acetate

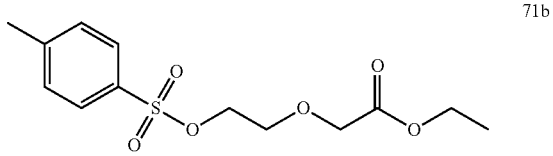 [SMILES: CCOC(=O)COCCOS(=O)(=O)c1ccc(C)cc1]

To a solution of ethyl 2-(2-hydroxyethoxy)acetate (1.1 g, 7.42 mmol) in DCM (20 mL) at room temperature was added triethylamine (2.07 mL, 14.85 mmol), m-toluene-sulfonyl chloride (1.7 g, 8.91 mmol) and the reaction mixture was stirred at room temperature for 12 hours. After the reaction was completed, the mixture was concentrated in vacuo and the residue was purified by column chromatography on silica gel (elution with PE:EtOAc=50:1-10:1) to give ethyl 2-[2-(p-tolylsulfonyloxy)ethoxy]acetate (0.400 g, 1.32 mmol) as a colorless oil. MS obsd. (ESI$^+$) [(M+H)$^+$]: 303.1.

Step 3: Preparation of ethyl 2-[2-[4-(7-bromo-8-chloro-4-oxo-chromen-2-yl)phenoxy]ethoxy]acetate

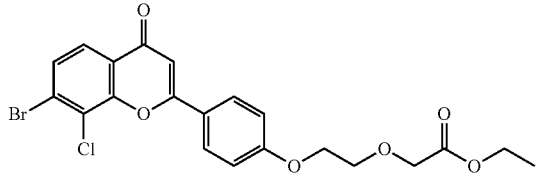

71

To a mixture of 7-bromo-8-chloro-2-(4-hydroxyphenyl)chromen-4-one (3.0 g, 8.53 mmol) and ethyl 2-[2-(p-tolylsulfonyloxy)ethoxy]acetate (3.1 g, 10.24 mmol) in DMF (30 mL) was added potassium carbonate (1.77 g, 12.8 mmol) and the mixture was stirred at 80° C. for 16 hours. After the reaction was completed, the mixture was poured into water (50 mL) and extracted with EtOAc (100 mL) twice. The combined organic phase was washed with brine, dried over $Na_2SO_4$ and concentrated in vacuo. The residue was then triturated in EtOAc (15 mL) and the mixture was then filtered. The solid was collected and dried in vacuo to give ethyl 2-[2-[4-(7-bromo-8-chloro-4-oxo-chromen-2-yl)phenoxy]ethoxy]acetate (3.5 g, 58.23% yield) as a yellow solid. $^1$H NMR (DMSO-$d_6$, 400 MHz): δ ppm 8.08 (br d, J=9.05 Hz, 2H), 7.81-7.94 (m, 2H), 7.16 (br d, J=9.17 Hz, 2H), 7.08 (s, 1H), 4.17-4.29 (m, 4H), 4.06-4.15 (m, 2H), 3.82-3.92 (m, 2H), 1.21 (t, J=7.15 Hz, 3H). MS obsd. (ESI$^+$) [(M+H)$^+$]: 482.1.

Example 72

3-[2-[4-[8-chloro-4-oxo-7-(trifluoromethyl)chromen-2-yl]-2-methyl-phenoxy]ethoxy]cyclobutanecarboxylic acid

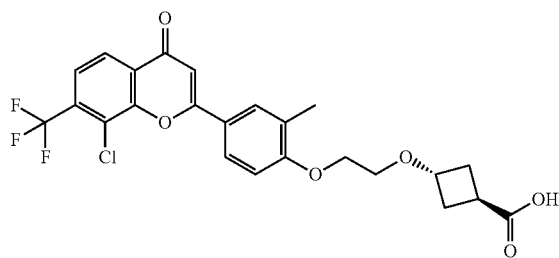

72

Step 1: Preparation of 4-(methoxymethoxy)-3-methyl-benzaldehyde

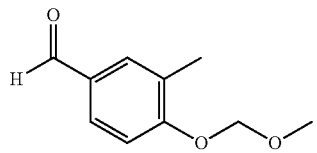

72a

To a solution of 4-hydroxy-3-methyl-benzaldehyde (3000.0 mg, 22.03 mmol) and chloromethyl methyl ether (2.01 mL, 26.44 mmol) in THF (40 mL) cooled at 0° C. was added and sodium hydride (634.59 mg, 26.44 mmol), the mixture was stirred at 0° C. for 30 minutes. After the reaction was completed, the mixture was quenched by water (30 mL) and the resulting mixture was extracted with EtOAc (20 mL) twice. The combined organic layer was dried over Na2SO4 and concentrated in vacuo. The residue was purified by column chromatography on silica gel (elution with PE:EtOAc 10:1-5:1) to give 4-(methoxymethoxy)-3-methyl-benzaldehyde as a yellow liquid. MS obsd. (ESI$^+$) [(M+H)$^+$]: 181.1.

Step 2: Preparation of (E)-1-(4-bromo-3-chloro-2-hydroxy-phenyl)-3-[4-(methoxymethoxy)-3-methyl-phenyl]prop-2-en-1-one

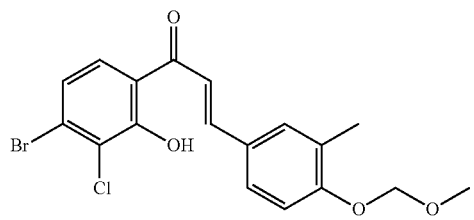

72b

A mixture of 1-(4-bromo-3-chloro-2-hydroxy-phenyl)ethanone (2870.0 mg, 11.5 mmol), potassium hydroxide (3227.3 mg, 57.52 mmol) and 4-(methoxymethoxy)-3-methyl-benzaldehyde (2487.51 mg, 13.8 mmol) in ethanol (120 mL) was stirred at 30° C. for 16 hours. After the reaction was completed, the mixture was adjusted to pH~4.0 with 1N HCl solution. The resulting suspension was then filtered and solid was washed by water (200 mL) and EtOH (100 mL) in sequence. The solid was concentrated in vacuo to give the crude product of (E)-1-(4-bromo-3-chloro-2-hydroxy-phenyl)-3-[4-(methoxymethoxy)-3-methyl-phenyl]prop-2-en-1-one (4.0 g, 43% yield) as a yellow solid. MS obsd. (ESI$^+$) [(M+H)$^+$]: 411.1.

Step 3: Preparation of 7-bromo-8-chloro-2-(4-hydroxy-3-methyl-phenyl)chromen-4-one

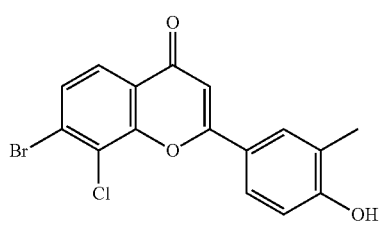

72c

To a solution of (E)-1-(4-bromo-3-chloro-2-hydroxy-phenyl)-3-[4-(methoxymethoxy)-3-methyl-phenyl]prop-2-en-1-one (600.0 mg, 1.46 mmol) in DMSO (6 mL) was added iodine (36.99 mg, 0.150 mmol) and the mixture was stirred at 140° C. for 4 hours. After the reaction was completed, the mixture was poured into water (60 mL). The resulting suspension was then filtered and solid was washed by Na$_2$SO$_3$ solution (2 mol/L, 10 mL) and water (50 mL) in sequence. The solid was concentrated in vacuo to give the crude product of 7-bromo-8-chloro-2-(4-hydroxy-3-methyl-phenyl)chromen-4-one (430 mg, 44% yield,) as a yellow solid. MS obsd. (ESI$^+$) [(M+H)$^+$]: 365.0.

Step 4: Preparation of methyl 3-[2-[4-(7-bromo-8-chloro-4-oxo-chromen-2-yl)-2-methyl-phenoxy]ethoxy]cyclobutanecarboxylate

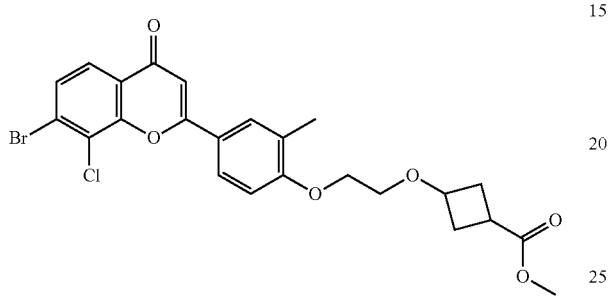

72d

To a solution of 7-bromo-8-chloro-2-(4-hydroxy-3-methyl-phenyl)chromen-4-one (340.0 mg, 0.930 mmol, 1 eq), potassium carbonate (385.59 mg, 2.79 mmol, 3 eq) in DMF (10 mL) was added methyl 3-[2-(p-tolylsulfonyloxy)ethoxy]cyclobutanecarboxylate (335.92 mg, 1.02 mmol, 1.1 eq) and the mixture was stirred at 80° C. for 4 hours. After the reaction was complete, the mixture was diluted with water (50 mL) and the resulting mixture was extracted with EtOAc (30 mL) three times. The combined organic layer was washed with brine, dried over Na$_2$SO$_4$ and concentrated in vacuo. The residue was purified by preparative HPLC to give two diastereomers of the methyl 3-[2-[4-(7-bromo-8-chloro-4-oxo-chromen-2-yl)-2-methyl-phenoxy]ethoxy]cyclobutanecarboxylate with cis- and trans-configuration, one of which is appointed as 72d-A (82 mg, 14% yield, purity 100%) and the other is 72d-B (170 mg, 19% yield, purity 63.69%). MS obsd. (ESI$^+$) [(M+H)$^+$]: 520.9.

Step 5: Preparation of methyl 3-[2-[4-[8-chloro-4-oxo-7-(trifluoromethyl)chromen-2-yl]-2-methyl-phenoxy]ethoxy]cyclobutanecarboxylate

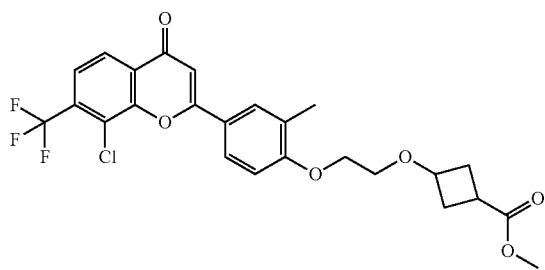

72e

To a solution of methyl 3-[2-[4-(7-bromo-8-chloro-4-oxo-chromen-2-yl)-2-methyl-phenoxy]ethoxy]cyclobutanecarboxylate (72d-A, 82.0 mg, 0.160 mmol) in DMF (5 mL) was added iodocopper (59.86 mg, 0.310 mmol), methyl 2,2-difluoro-2-(fluorosulfonyl)acetate (150.95 mg, 0.790 mmol) and the mixture was then stirred at 120° C. for 6 hours. After the reaction was completed, the reaction was diluted with water (20 mL) and the resulting mixture was extracted with EtOAc (20 mL) three times. The combined organic layer was washed with brine, dried over Na$_2$SO$_4$ and concentrated in vacuo to give the crude of methyl 3-[2-[4-[8-chloro-4-oxo-7-(trifluoromethyl)chromen-2-yl]-2-methyl-phenoxy]ethoxy]cyclobutanecarboxylate (62 mg, 48% yield, purity 33.91%) as a yellow solid, which was used in the next step directly without further purification. MS obsd. (ESI$^+$) [(M+H)$^+$]: 511.1

Step 6: Preparation of 3-[2-[4-[8-chloro-4-oxo-7-(trifluoromethyl)chromen-2-yl]-2-methyl-phenoxy]ethoxy]cyclobutanecarboxylic acid

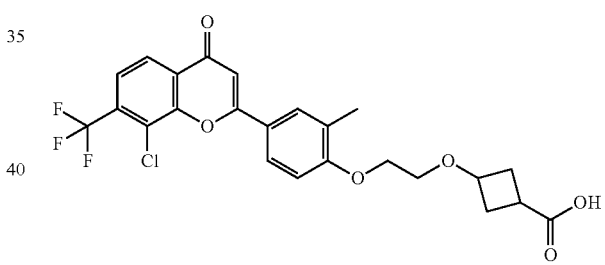

72

To a solution of methyl 3-[2-[4-[8-chloro-4-oxo-7-(trifluoromethyl)chromen-2-yl]-2-methyl-phenoxy]ethoxy]cyclobutanecarboxylate (62.0 mg, 0.120 mmol) in the mixed solvent of THF (1 mL) and water (0.5 mL) was added lithium hydroxide (4.36 mg, 0.180 mmol) and the mixture was stirred at room temperature for 2 hours. After the reaction was completed, the mixture was adjusted to pH~5 by addition of HCl solution (2M). The resulting mixture was extracted with EtOAc (20 mL) three times. The combined organic layer was concentrated in vacuo and the residue was purified by preparative HPLC to give 3-[2-[4-[8-chloro-4-oxo-7-(trifluoromethyl)chromen-2-yl]-2-methyl-phenoxy]ethoxy]cyclobutanecarboxylic acid (9.5 mg, 14% yield). $^1$H NMR (DMSO-d$_6$, 400 MHz): δ ppm 12.18 (br s, 1H), 8.13 (d, J=8.31 Hz, 1H), 7.81-8.06 (m, 3H), 7.09-7.21 (m, 2H), 4.13-4.27 (m, 3H), 3.70 (br s, 2H), 2.87-3.00 (m, 1H), 2.40 (ddd, J=3.48, 6.82, 12.93 Hz, 2H), 2.26 (s, 3H), 2.09-2.19 (m, 2H). MS obsd. (ESI$^+$) [(M+H)$^+$]: 497.0.

Example 73

Cis-3-[2-[2-chloro-4-[8-chloro-4-oxo-7-(trifluoromethyl)chromen-2-yl]phenoxy]ethoxy]cyclobutanecarboxylic acid

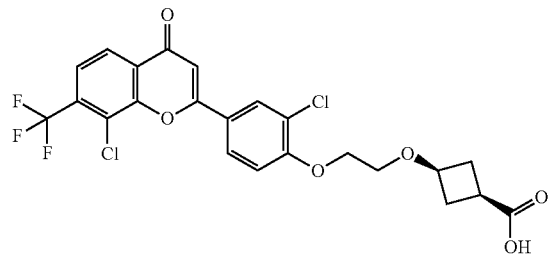

Step 1: Preparation of 2-benzyloxyethyl trifluoromethanesulfonate

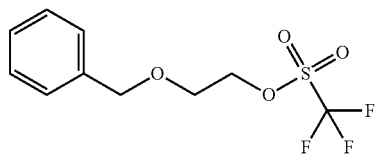

To a solution of 2-benzyloxyethanol (2.0 g, 13.4 mmol) and 2,6-dimethylpyridine (2.8 g, 26.8 mmol) in dichloromethane (40 mL) was added trifluoromethanesulfonic anhydride (7.4 g, 26.8 mmol) at −30° C. and the mixture was then stirred at 0° C. for 1 hour. The mixture was then washed with 1 N HCl (20 mL) twice, water (20 mL) twice, brine (20 mL), dried over anhydrous $Na_2SO_4$ and concentrated in vacuo to give the crude of 2-benzyloxyethyl trifluoromethanesulfonate (4.0 g, 100% yield), which was used in the next step directly without further purification. MS obsd. (ESI$^+$) [(M+H)$^+$]: 307.3.

Step 2: Preparation of cis-tert-butyl 3-(2-benzyloxyethoxy)cyclobutanecarboxylate

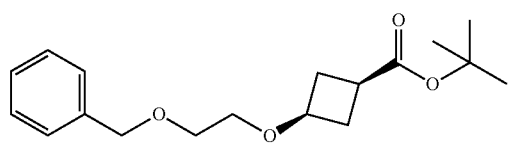

To a solution of cis-tert-butyl 3-hydroxycyclobutanecarboxylate (CAS #: 939768-64-6, Cat. #: B253665, from BePharm Ltd, 2.26 g, 18 mmol) in THF (20 mL) was added NaH (315 mg, 7.9 mmol) portion wise at 0° C. and the mixture was then stirred at 0° C. for 30 minutes. Then to the resulting mixture was added the solution of 2-benzyloxyethyl trifluoromethanesulfonate (4.0 g, 13.4 mmol, crude) in THF (40 mL) dropwise at 0° C. After addition, the mixture was poured into ice-water (50 mL) and extracted with dichloromethane (50 mL) three times. The combined organic layer was washed with brine, dried over anhydrous $Na_2SO_4$ and concentrated in vacuo. The residue was purified by column chromatography on silica gel (elution with PE:EtOAc=100:1 to 3:1) to give cis-tert-butyl 3-(2-benzyloxyethoxy)cyclobutanecarboxylate (1.5 g, 37.3% yield) as a yellow oil. MS obsd. (ESI$^+$) [(M+Na)$^+$]: 329.2.

Step 3: Preparation of cis-tert-butyl 3-(2-hydroxyethoxy)cyclobutanecarboxylate

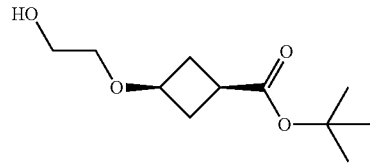

Compound 73c was prepared in analogy to the procedure described for the preparation of Int-1 by using cis-tert-butyl 3-(2-benzyloxyethoxy)cyclobutanecarboxylate as the starting materials instead of methyl 3-(2-hydroxyethoxy)cyclobutanecarboxylate in Step 2.

Step 4: Preparation of cis-tert-butyl 3-[2-(p-tolylsulfonyloxy)ethoxy]cyclobutanecarboxylate

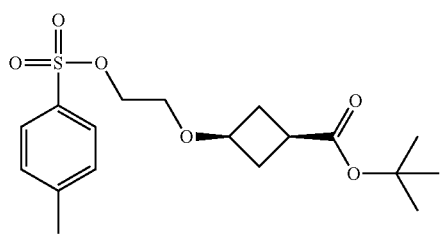

Compound 73d was prepared in analogy to the procedure described for the preparation of intermediate Int-2 by using cis-tert-butyl 3-(2-hydroxyethoxy)cyclobutanecarboxylate as the starting materials instead of methyl 3-(2-hydroxyethoxy)cyclobutanecarboxylate.

Step 5: Preparation of 8-chloro-2-(3-chloro-4-hydroxy-phenyl)-7-(trifluoromethyl)chromen-4-one

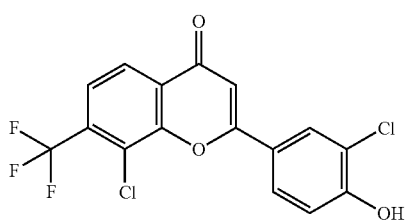

Compound 73e was prepared in analogy to the procedure described for the preparation of compound 72c by using 3-chloro-4-hydroxy-benzaldehyde as the starting materials instead of 4-hydroxy-3-methyl-benzaldehyde in the step 1.

Step 6: Preparation of cis-tert-butyl 3-[2-[4-(7-bromo-8-chloro-4-oxo-chromen-2-yl)-2-chloro-phenoxy]ethoxy]cyclobutanecarboxylate 73f

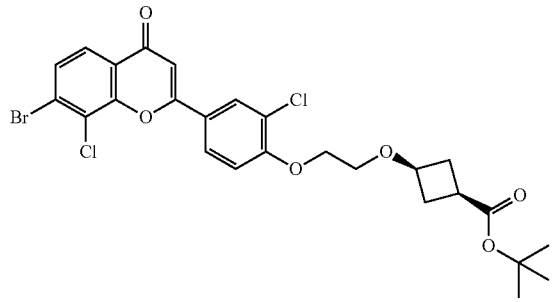

Compound 73f was prepared in analogy to the procedure described for the preparation of compound 72d by using 8-chloro-2-(3-chloro-4-hydroxy-phenyl)-7-(trifluoromethyl)chromen-4-one and cis-tert-butyl 3-[2-(p-tolylsulfonyloxy)ethoxy]cyclobutanecarboxylate as the starting material instead of 7-bromo-8-chloro-2-(4-hydroxy-3-methyl-phenyl)chromen-4-one and methyl 3-[2-(p-tolylsulfonyloxy)ethoxy]cyclobutanecarboxylate in the step 4.

Step 7: Preparation of cis-3-[2-[2-chloro-4-[8-chloro-4-oxo-7-(trifluoromethyl)chromen-2-yl]phenoxy]ethoxy]cyclobutanecarboxylic acid

73

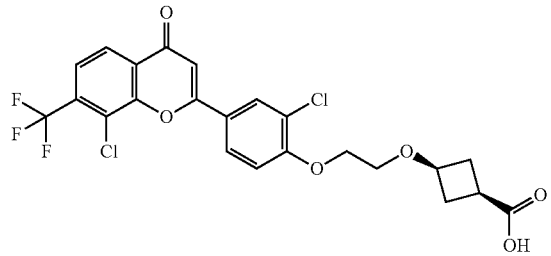

Example 73 was prepared in analogy to the procedure described for the preparation of example 72 by using cis-tert-butyl 3-[2-[4-(7-bromo-8-chloro-4-oxo-chromen-2-yl)-2-chloro-phenoxy]ethoxy]cyclobutanecarboxylate as the starting materials instead of methyl 3-[2-[4-(7-bromo-8-chloro-4-oxo-chromen-2-yl)-2-methyl-phenoxy]ethoxy]cyclobutanecarboxylate in the step 5.

Example 73: $^1$H NMR (DMSO-$d_6$, 400 MHz): δ ppm 9.03 (s, 1H), 8.63 (d, J=5.7 Hz, 1H), 7.98-8.06 (m, 2H), 7.51 (t, J=7.9 Hz, 1H), 7.34 (d, J=5.8 Hz, 1H), 7.16 (s, 1H), 4.36-4.40 (s, 2H), 3.92-3.97 (m, 1H), 3.72-3.76 (m, 2H), 2.38-2.40 (m, 3H), 1.96-1.98 (m, 2H). MS obsd. (ESI$^+$) [(M+H)$^+$]:517.1.

BIOLOGICAL EXAMPLES

Example 74: Engineered HepDES19 Primary Screen Assay

The assay was employed to screen for novel cccDNA inhibitors. HepDES19 is a cccDNA-producing cell line. In this cell line, HBeAg in the cell culture supernatant as surrogate marker, as HBeAg production depends on cccDNA level and activity. HepDES19 is an engineered cell line which contains a 1.1 unit length HBV genome, and pgRNA transcription from the transgene is controlled by Tetracycline (Tet). In the absence of Tet, pgRNA transcription will be induced, but HBV e antigen (HBeAg) could not be produced from this pgRNA due to very short leader sequence before the HBeAg start codon and the start codon is disrupted. Only after cccDNA is formed, the missing leader sequence and start codon mutation would be restored from the 3'-terminal redundancy of pgRNA, and then HBeAg could be synthesized. Therefore, HBeAg could be used as a surrogate marker for cccDNA (Zhou, T. et al., Antiviral Res. (2006), 72(2), 116-124; Guo, H. et al., J. Virol. (2007), 81(22), 12472-12484).

HepDES19 cells were seeded at 2×10$^6$ cells per T150 flask and cultured with the culture medium (Dulbecco's Modified Eagle Medium: Nutrient Mixture F-12 [DMEM-F12, Gibco Cat. 11320-82], 10% Fetal Bovine Serum [FBS, Clontech Cat. 631101], 0.1 mM Non-Essential Amino Acids Solution [NEAA, Gibco Cat. 11140-050], 50 μg/mL Penicillin-Streptomycin [PS, Invitrogen Cat. 15140-163], 500 μg/mL Geneticin [G418, Invitrogen Cat. 10131-027]) containing 3 μg/mL Tet (Sigma, Cat. 87128) for 5 days. Cells were then seeded at 4×10$^6$ cells per T150 in the same culture medium as described above in the absence of Tet for 8 days. Cells were then harvested and frozen at density of 2×10$^6$ cells per mL. For compound testing, the frozen cells were thawed and seeded into 96-well plates at a density of 6×10$^4$ cells per well. At 24 hrs after seeding, half log serial dilutions of compounds made with Dimethyl sulfoxide (DMSO, Sigma, Cat. D2650) were further diluted with the same culture medium as described above before they were added to the cells to reach desired final compound concentrations and 1% DMSO concentration. Plates were then incubated at 37° C. for another 5 days before measurement of HBeAg level and cell viability. Intracellular HBeAg level were measured with enzyme-linked immunosorbent assay (ELISA) kit (Shanghai Kehua Diagnostic Medical Products Co., Ltd). Cell viability was assessed using Cell Counting Kit-8 (Donjindo, Cat. CK04-20). IC$_{50}$ values were derived from the dose-response curve using 4 parameter logistic curve fit method.

The compounds of the present invention were tested for their capacity to inhibit extracellular HBeAg level as described herein. The compounds of this invention were found to have IC$_{50}$ below 50 μM. Particular compounds of formula (I) were found to have IC$_{50}$ below 5.0 μM. Results of HepDES19 primary screen assay are given in Table 1.

TABLE 1

| Activity data in HepDES19 primary screen assay | | | | | |
|---|---|---|---|---|---|
| Example No. | IC$_{50}$ (μM) | Example No. | IC$_{50}$ (μM) | Example No. | IC$_{50}$ (μM) |
| 1 | 0.14 | 25 | 1.05 | 56 | 29.55 |
| 1-A | 0.14 | 27 | 7.68 | 57 | 0.09 |
| 1-B | 0.14 | 28 | 2.80 | 58 | 0.52 |
| 2 | 2.48 | 29 | 0.21 | 59 | 20.21 |
| 3 | 0.15 | 30 | 0.13 | 60 | 4.84 |
| 4-A | 0.53 | 31 | 0.78 | 61 | 0.144 |

TABLE 1-continued

Activity data in HepDES19 primary screen assay

| Example No. | IC$_{50}$ (μM) | Example No. | IC$_{50}$ (μM) | Example No. | IC$_{50}$ (μM) |
|---|---|---|---|---|---|
| 4-B | 5.23 | 33 | 0.31 | 62-A | 1.013 |
| 5-A | 1.36 | 34 | 16.02 | 62-B | 1.325 |
| 5-B | 11.16 | 35 | 13.89 | 63 | 1.81 |
| 6 | 1.95 | 37 | 8.97 | 64 | 5.5 |
| 7-A | 15.43 | 38-A | 5.29 | 65 | 6.5 |
| 7-B | 19.66 | 38-B | 0.76 | 66-B | 13.184 |
| 8 | 1.34 | 39 | 9.01 | 67 | 14.132 |
| 9 | 2.46 | 40 | 1.61 | 68 | 10.099 |
| 10 | 0.79 | 41 | 12.76 | 69 | 10.739 |
| 11 | 0.57 | 42 | 0.61 | 70 | 17.2 |
| 12 | 1.07 | 43 | 0.25 | 70-A | 19.8 |
| 13 | 0.69 | 44 | 0.57 | 70-B | 2.144 |
| 14 | 20.41 | 45 | 13.20 | 71 | 9.304 |
| 15 | 10.33 | 46 | 16.01 | 72 | 14.4 |
| 19 | 22.15 | 47 | 0.04 | 73 | 15.4 |
| 20 | 0.70 | 48 | 7.68 | F-1 | >50 |
| 21 | 0.29 | 50 | 1.78 | F-2 | 16.3 |
| 22 | 13.04 | 51 | 0.86 | F-3 | >50 |
| 23 | 21.08 | 53 | 22.0 | | |
| 24 | 1.14 | 55 | 0.12 | | |

Example 75: cccDNA Southern Blot Assay

HepDES19 cells were seeded at 4×10$^6$ cells per T150 in the culture medium (Dulbecco's Modified Eagle Medium: Nutrient Mixture F-12 [DMEM-F12, Gibco Cat. 11320-82], 10% Fetal Bovine Serum [FBS, Clontech Cat. 631101], 0.1 mM Non-Essential Amino Acids Solution [NEAA, Gibco Cat. 11140-050], 50 μg/mL Penicillin-Streptomycin [PS, Invitrogen Cat. 15140-163], 500 μg/mL Geneticin [G418, Invitrogen Cat. 10131-027]) in the absence of Tet for 8 days. These cells were seeded at the density of 1×10$^6$ cells per well in 6-well plate. At 24 hrs after seeding, serial dilutions of compounds made with DMSO (Sigma, Cat. D2650) were further diluted with the same culture medium as described above before they were added to the cells to reach desired final compound concentrations and 1% DMSO concentration. After 5 days' compound treatment, the cells growing in one well from 6-well plate were re-suspended with 500 μL re-suspension buffer (50 mM tris[hydroxymethyl]amino methane pH 7.5), 10 mM ethylenediaminetetraacetic acid (EDTA), 50 μg/mL RNase A [Qiagen, Cat. 158922]. 500 μL of 1.2% sodium dodecyl sulfate (SDS) was then added into the re-suspended cells to lyse the cells. After 15 minutes' incubation, 700 μL precipitation buffer (3M cesium chloride, 1M potassium acetate, 0.67M acetic acid) was added and the lysate was incubated at 4° C. for 2 h. The lysate was centrifuged at 15000 revolutions per minute (RPM) at 4° C. for 15 minutes. The supernatant was collected and loaded onto Qiagen miniprep columns (QIAprep spin Mini prep kit, Cat. No. 27016). After centrifugation for 1 minute at 15000 RPM, the column was washed once with 750 μL wash buffer PE (QIAprep spin Mini prep kit, Cat. No. 27016). 80 μL of double distilled water was loaded to the columns to elute Hirt DNA.

Hirt DNA of each sample was loaded into 1.2% 1× tris-acetate electrophoresis (TAE) agarose gel and separated at 90 voltages for 3 hours. The gel was then treated in 50 mM NaAc-HAc, pH4.2 for 30 min at room temperature (RT), and then denatured by soaking in denaturation buffer (0.5 M sodium hydroxide, 1.5 M sodium chloride) at RT for 30-45 min. The gel was then treated with neutralization buffer (1M tris[hydroxymethyl]aminomethane pH7.4 and 1.5M NaCl) at RT for 30~45 min.

The gel was transferred onto a pre-wet Nylon membrane (GE life science, Hybond N+) by capillary transfer method overnight, followed by UV crosslinking. The membrane was transferred into a hybridization tube, then rinsed with double distilled water at 60° C. for 5 min. 10 mL of hybridization buffer (Lab kits, China) was added, the resulting sample was rotated in hybridization oven at 60° C. for 1 hour. Digoxigenin (DIG)-labelled HBV probe was denatured at 95° C. for 10 minutes, and then 7 μL of denatured probe was added to the hybridization tube, which was rotated in hybridization oven at 60° C. overnight.

On the second day, the membrane was washed according to the procedure of DIG wash and block buffer set kit (Roche, Cat. 11 585 762 001), and then incubated with 50 mL antibody solution (Antibody anti-Digoxigenin-AP Fab fragment [Roche Cat. 11093274910] diluted in fresh 1× blocking buffer at 1:10,000) for 1 hour. The membrane was washed with 50 mL washing buffer (1× Maleic buffer with 0.3% Tween-20) for 15 minutes twice, and equilibrated with 20 mL detection buffer (0.1M tris[hydroxymethyl]aminomethane pH9.5, 0.1M sodium chloride) for 5 minutes. CDP-Star substrate (Roche, Cat. 12041677001) was added to the membrane for 5 minutes, and then the membrane was scanned by Bio-Rad Visualize Image System (Biorad, ChemiDoc-MP, Serial No. 731BR00916).

Results of cccDNA Southern Blot assay are given in FIG. 1. The results indicate that the compounds of this invention dose-dependently reduced cccDNA level in HepDES19 cells.

Example 76: Cryopreserved Primary Human Hepatocytes (PHH) Assay

This assay is used to confirm the anti-HBV effect of the compounds in HBV PHH infection assay. Cryopreserved PHH (BioreclamationIVT, Lot YJM) was thawed at 37° C. and gently transferred into pre-warmed InVitroGRO HT medium (BioreclamationIVT, Cat. S03317). The mixture was centrifuged at 70 relative centrifugal force (RCF) for 3 minutes at RT, and the supernatant was discarded. Pre-warmed InVitroGRO CP medium (BioreclamationIVT, Cat #S03316) was added to the cell pellet to gently re-suspend cells. The cells were seeded at the density of 5.8×10$^4$ cells per well to collagen I coated 96-well plate (Gibco, Cat. A1142803) with the InVitroGRO CP medium. All plates were incubated at 37° C. with 5% CO$_2$ and 85% humidity.

At 20 hours after plating, the medium was changed to PHH culture medium (Dulbecco's Modified Eagle Medium (DMEM)/F12 (1:1) (Gibco, Cat. 11320-033), 10% fetal bovine serum (Gibco Cat. 10099141), 100 U/mL penicillin, 100 μg/mL streptomycin (Gibco, Cat. 151401-122), 5 ng/mL human epidermal growth factor (Invitrogen Cat. PHG0311L), 20 ng/mL dexamethasone (Sigma, Cat. D4902) and 250 ng/mL human recombinant insulin (Gibco, Cat. 12585-014)). And the cells were incubated at 37° C. with 5% CO$_2$ and 85% humidity for 4 hours. The medium was then changed to pre-warmed PHH culture medium containing 4% polyethylene glycol (PEG) MW8000 (Sigma, Cat. P1458-50ML) and 1% DMSO (Sigma, Cat. D2650). 5.8×10$^6$ genomic equivalents of HBV were added into the medium.

At 24 hours post-infection, the cells were gently washed with PBS and refreshed with PHH culture medium supplemented with 1% DMSO, and 0.25 mg/mL Matrix gel (Corning, Cat. 356237) at 200 μL per well. All plates were immediately placed in at 37° C. CO$_2$ incubator.

24 hours later, serial dilutions of compounds made with DMSO were further diluted with the same culture medium (PHH culture medium supplemented with 1% DMSO and 0.25 mg/mL Matrix gel as described above) before they were added to the cells to reach desired final compound concentrations and 1% DMSO concentration. The medium containing the compounds were refreshed every three days.

At 9 days post-compound treatment, extracellular HBsAg level were measured with Chemiluminescence Immuno Assay (CLIA) kit (Autobio, HBsAg Quantitative CLIA). Extracellular HBV DNA was extracted by MagNA Pure 96 system (Roche) and then determined by quantitative PCR with the following primers and probe:

```
HBV-Forward Primer (SEQ ID NO: 1):
AAGAAAAACCCCGCCTGTAA (5' to 3');

HBV-Reverse Primer (SEQ ID NO: 2):
CCTGTTCTGACTACTGCCTCTCC (5' to 3');

HBV-Probe: 5' + tetramethylrhodamine +
SEQ ID NO: 3 + black hole quencher 2-3', wherein
SEQ ID NO: 3 is CCTGATGTGATGTTCTCCATGTTCAGC.
```

HBsAg $IC_{50}$ and HBV DNA $IC_{50}$ values were derived from the dose-response curve using 4 parameter logistic curve fit method. The compounds of formula (I) have HBsAg $IC_{50}$<20 μM, particularly <1 μM; and HBV DNA $IC_{50}$<50 μM. Test results of the compounds of this invention as well as the reference compounds in Cryopreserved PHH assay are given in Table 2 and Table 3.

TABLE 2

HBsAg $IC_{50}$ data in Cryopreserved PHH assay

| Example No. | HBsAg $IC_{50}$ (μM) | Example No. | HBsAg $IC_{50}$ (μM) | Example No. | HBsAg $IC_{50}$ (μM) |
|---|---|---|---|---|---|
| F-1 | 61.7 | 15 | 0.28 | 45 | 0.53 |
| F-2 | 46.5 | 19 | 1.51 | 46 | 0.13 |
| F-3 | >100 | 21 | 5.10 | 47 | 0.24 |
| 1 | 0.13 | 23 | 7.11 | 50 | 10.24 |
| 1-A | 0.72 | 23-B | 6.89 | 51 | 0.94 |
| 1-B | 0.08 | 24 | 4.83 | 53 | 4.01 |
| 2 | 0.19 | 25 | 0.93 | 55 | 9.50 |
| 3 | 12.53 | 28 | 1.92 | 57 | 0.14 |
| 4-A | 6.34 | 29 | 0.90 | 58 | 0.57 |
| 4-B | 0.51 | 30 | 7.29 | 62-A | 4.22 |
| 5-B | 1.78 | 33 | 0.68 | 63 | 5.36 |
| 6 | 0.86 | 38-A | 0.46 | 66-B | 4.78 |
| 8 | 0.12 | 38-B | 0.88 | 67 | 2.77 |
| 10 | 2.72 | 39 | 5.74 | 69 | 2.01 |
| 11 | 12.47 | 40 | 7.12 | 70-B | 4.79 |
| 12 | 0.21 | 42 | 0.58 | 72 | 7.41 |
| 13 | 1.27 | 43 | 0.22 | 73 | 6.77 |
| 14 | 19.25 | 44 | 0.04 | | |

TABLE 3

HBV DNA $IC_{50}$ in Cryopreserved PHH assay

| Example No. | $IC_{50}$ (μM) |
|---|---|
| Example 3 | 35.7 |

The invention claimed is:
1. A compound of formula (I)

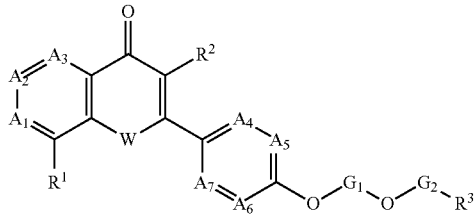

wherein:
W is O or S;
$A_1$ is CH or $CR^4$;
$A_2$ is CH or $CR^4$;
$A_3$ is CH or $CR^4$;
$A_4$ is N, CH or $CR^4$;
$A_5$ is N, CH or $CR^4$;
$A_6$ is CH;
$A_7$ is N or CH;
$R^1$ is halogen, $C_{1-6}$alkyl or $C_{3-7}$cycloalkyl;
$R^2$ is H, OH, halogen, $C_{1-6}$alkoxy, halo$C_{1-6}$alkoxy or phenyl$C_{1-6}$alkoxy;
$R^3$ is carboxy or $C_{1-6}$alkoxycarbonyl;
$R^4$ is halogen, OH, CN, $C_{1-6}$alkyl, $C_{3-7}$cycloalkyl, $C_{1-6}$alkoxy, oxopyrrolidinyl, morpholinyl or halo$C_{1-6}$alkyl;
$G_1$ is $C_{1-6}$alkylenyl, hydroxy$C_{1-6}$alkylenyl or $C_{3-7}$cycloalkyl$C_{1-6}$alkylenyl; and
$G_2$ is $C_{1-6}$alkylenyl, $C_{3-7}$cycloalkylenyl or phenylene;
or a pharmaceutically acceptable salt, or enantiomer, or diastereomer thereof.
2. A compound according to claim 1, wherein:
$R^1$ is Cl, Br, methyl or cyclopropyl;
$R^2$ is H, OH, Cl, Br, methoxy, trifluoromethoxy or benzyloxy;
$R^3$ is carboxy, methoxycarbonyl or ethoxycarbonyl;
$R^4$ is F, Cl, Br, OH, CN, methyl, isopropyl, cyclopropyl, methoxy, ethoxy, isopropoxy, oxopyrrolidinyl, morpholinyl or trifluoromethyl;
$G_1$ is cyclobutylmethylene, ethylenyl, hydroxypropylenyl, isopropylenyl or propylenyl; and
$G_2$ is cyclobutylenyl, cyclohexylenyl, cyclopentylenyl, cyclopropylenyl, isopropylenyl, ethylenyl, methylene and phenylene;
or a pharmaceutically acceptable salt, or enantiomer, or diastereomer thereof.
3. A compound according to claim 1, wherein $A_1$ is CH.
4. A compound according to claim 1, wherein $A_4$ is CH or $CR^4$.
5. A compound according to claim 1, wherein $A_5$ is CH or $CR^4$.
6. A compound according to claim 1, wherein $A_7$ is CH.
7. A compound according to claim 1, wherein $R^1$ is halogen.
8. A compound according to claim 1, wherein $R^2$ is H.
9. A compound according to claim 1, wherein $R^3$ is carboxy.
10. A compound according to claim 1, wherein $R^4$ is halogen, $C_{1-6}$alkyl or $C_{1-6}$alkoxy.
11. A compound according to claim 1, wherein $G_1$ is $C_{1-6}$alkylenyl.
12. A compound according to claim 1, wherein $G_2$ is $C_{1-6}$alkylenyl or $C_{3-7}$cycloalkylenyl.
13. A compound according to claim 1, wherein:
$R^1$ is halogen;
$R^2$ is H;
$R^3$ is carboxy;
$R^4$ is halogen, $C_{1-6}$alkyl or $C_{1-6}$alkoxy;
$G_1$ is $C_{1-6}$alkylenyl; and
$G_2$ is $C_{1-6}$alkylenyl or $C_{3-7}$cycloalkylenyl.
14. A compound according to claim 13, wherein:
$R^4$ is F, Cl, Br, methyl, ethoxy or methoxy;
$G_1$ is ethylenyl or isopropylenyl; and
$G_2$ is cyclobutylenyl or methylene.
15. A compound according to claim 1, selected from:
3-[2-[4-(8-chloro-4-oxo-chromen-2-yl)phenoxy]ethoxy]cyclobutanecarboxylic acid;
ethyl 3-[2-[4-(8-chloro-4-oxo-chromen-2-yl)phenoxy]ethoxy]cyclobutanecarboxylate;
3-[2-[4-(8-chloro-4-oxo-chromen-2-yl)phenoxy]ethoxy]benzoic acid;
ethyl 2-[2-[4-(8-chloro-4-oxo-chromen-2-yl)phenoxy]ethoxy]cyclopropanecarboxylate;
cis-2-[2-[4-(8-chloro-4-oxo-chromen-2-yl)phenoxy]ethoxy]cyclopropanecarboxylic acid;
trans-2-[2-[4-(8-chloro-4-oxo-chromen-2-yl)phenoxy]ethoxy]cyclopropanecarboxylic acid;
3-[2-[4-(8-chloro-4-oxo-chromen-2-yl)phenoxy]ethoxy]cyclopentanecarboxylic acid;
cis-4-[2-[4-(8-chloro-4-oxo-chromen-2-yl)phenoxy]ethoxy]cyclohexanecarboxylic acid;
trans-4-[2-[4-(8-chloro-4-oxo-chromen-2-yl)phenoxy]ethoxy]cyclohexanecarboxylic acid;
2-[3-[[4-(8-chloro-4-oxo-chromen-2-yl)phenoxy]methyl]cyclobutoxy]acetic acid;
2-[2-[4-(8-chloro-4-oxo-chromen-2-yl)phenoxy]ethoxy]acetic acid;
3-[2-[4-(8-chloro-4-oxo-chromen-2-yl)phenoxy]ethoxy]propanoic acid;
3-[2-[4-(8-chloro-4-oxo-chromen-2-yl)phenoxy]ethoxy]-2,2-dimethyl-propanoic acid;
3-[2-[4-(8-chloro-4-oxo-chromen-2-yl)phenoxy]-1-methyl-ethoxy]cyclobutanecarboxylic acid;
3-[3-[4-(8-chloro-4-oxo-chromen-2-yl)phenoxy]propoxy]cyclobutanecarboxylic acid;
3-[3-[4-(8-chloro-4-oxo-chromen-2-yl)phenoxy]-2-hydroxy-propoxy]benzoic acid;

3-[2-[4-(8-chloro-7-fluoro-4-oxo-chromen-2-yl)phenoxy]ethoxy]cyclobutanecarboxylic acid;
3-[2-[4-(8-chloro-7-methoxy-4-oxo-chromen-2-yl)phenoxy]ethoxy]cyclobutanecarboxylic acid;
3-[2-[4-(8-chloro-6-fluoro-4-oxo-chromen-2-yl)phenoxy]ethoxy]cyclobutanecarboxylic acid;
3-[2-[4-(7,8-dichloro-4-oxo-chromen-2-yl)phenoxy]ethoxy]cyclobutanecarboxylic acid;
3-[2-[4-(8-chloro-6-cyano-4-oxo-chromen-2-yl)phenoxy]ethoxy]cyclobutanecarboxylic acid;
3-[2-[4-(8-chloro-7-cyano-4-oxo-chromen-2-yl)phenoxy]ethoxy]cyclobutanecarboxylic acid;
cis-3-[2-[4-(8-chloro-5-hydroxy-4-oxo-chromen-2-yl)phenoxy]ethoxy]cyclobutanecarboxylic acid;
cis-3-[2-[4-(8-chloro-5-methoxy-4-oxo-chromen-2-yl)phenoxy]ethoxy]cyclobutanecarboxylic acid;
cis-3-[2-[4-(8-chloro-5-isopropoxy-4-oxo-chromen-2-yl)phenoxy]ethoxy]cyclobutanecarboxylic acid;
cis-3-[2-[4-(5-bromo-8-chloro-4-oxo-chromen-2-yl)phenoxy]ethoxy]cyclobutanecarboxylic acid;
cis-3-[2-[4-(5,8-dichloro-4-oxo-chromen-2-yl)phenoxy]ethoxy]cyclobutanecarboxylic acid;
cis-3-[2-[4-(8-chloro-5-cyclopropyl-4-oxo-chromen-2-yl)phenoxy]ethoxy]-cyclobutanecarboxylic acid;
cis-3-[2-[4-(8-chloro-5-methyl-4-oxo-chromen-2-yl)phenoxy]ethoxy]cyclobutanecarboxylic acid;
cis-3-[2-[4-(8-bromo-4-oxo-chromen-2-yl)phenoxy]ethoxy]cyclobutanecarboxylic acid;
cis-3-[2-[4-(8-cyclopropyl-4-oxo-chromen-2-yl)phenoxy]ethoxy]cyclobutanecarboxylic acid;
cis-3-[2-[4-(8-methyl-4-oxo-chromen-2-yl)phenoxy]ethoxy]cyclobutanecarboxylic acid;
2-[2-[4-(8-chloro-5-fluoro-4-oxo-chromen-2-yl)phenoxy]ethoxy]acetic acid;
cis-3-[2-[[5-(8-chloro-4-oxo-chromen-2-yl)-2-pyridyl]oxy]ethoxy]cyclobutanecarboxylic acid;
trans-3-[2-[[5-(8-chloro-4-oxo-chromen-2-yl)-2-pyridyl]oxy]ethoxy]cyclobutanecarboxylic acid;
cis-3-[2-[5-(8-chloro-4-oxo-chromen-2-yl)pyrazin-2-yl]oxyethoxy]cyclobutanecarboxylic acid;
cis-methyl 3-[2-[5-(8-chloro-4-oxo-chromen-2-yl)pyrazin-2-yl]oxyethoxy]-cyclobutanecarboxylate;
cis-methyl 3-[2-[6-(8-chloro-4-oxo-chromen-2-yl)pyridazin-3-yl]oxyethoxy]-cyclobutanecarboxylate;
cis-3-[2-[4-(8-chloro-4-oxo-chromen-2-yl)-2-fluoro-phenoxy]ethoxy]cyclobutanecarboxylic acid;
cis-3-[2-[2-chloro-4-(8-chloro-4-oxo-chromen-2-yl)phenoxy]ethoxy]cyclobutanecarboxylic acid;
cis-3-[2-[2-bromo-4-(8-chloro-4-oxo-chromen-2-yl)phenoxy]ethoxy]cyclobutanecarboxylic acid;
cis-3-[2-[4-(8-chloro-4-oxo-chromen-2-yl)-2-cyclopropyl-phenoxy]ethoxy]-cyclobutanecarboxylic acid;
3-[2-[4-(8-chloro-4-oxo-chromen-2-yl)-2-cyano-phenoxy]ethoxy]cyclobutanecarboxylic acid;
3-[2-[4-(8-chloro-4-oxo-chromen-2-yl)-2-methyl-phenoxy]ethoxy]cyclobutanecarboxylic acid;
3-[2-[4-(8-chloro-4-oxo-chromen-2-yl)-2-isopropyl-phenoxy]ethoxy]cyclobutanecarboxylic acid;
3-[2-[4-(8-chloro-4-oxo-chromen-2-yl)-3-methoxy-phenoxy]ethoxy]cyclobutanecarboxylic acid;
3-[2-[4-(8-chloro-4-oxo-chromen-2-yl)-3-ethoxy-phenoxy]ethoxy]cyclobutanecarboxylic acid;
3-[2-[4-(3,8-dichloro-4-oxo-chromen-2-yl)phenoxy]ethoxy]cyclobutanecarboxylic acid;
cis-3-[2-[4-(8-chloro-3-hydroxy-4-oxo-chromen-2-yl)phenoxy]ethoxy]cyclobutanecarboxylic acid;
cis-3-[2-[4-(8-chloro-3-methoxy-4-oxo-chromen-2-yl)phenoxy]ethoxy]cyclobutanecarboxylic acid;
3-[2-[4-(8-chloro-4-oxo-thiochromen-2-yl)phenoxy]ethoxy]cyclobutanecarboxylic acid;
2-[2-[4-(8-chloro-4-oxo-thiochromen-2-yl)phenoxy]ethoxy]acetic acid;
2-[2-[4-(8-chloro-3-hydroxy-4-oxo-chromen-2-yl)phenoxy]ethoxy]acetic acid;
3-[2-[4-(8-chloro-4-oxo-chromen-2-yl)-3-morpholino-phenoxy]ethoxy]cyclobutanecarboxylic acid;
2-[2-[4-(8-chloro-4-oxo-chromen-2-yl)phenoxy]ethoxy]acetamide;
methyl 3-[2-[4-[8-chloro-6-fluoro-4-oxo-3-(trifluoromethoxy)chromen-2-yl]phenoxy]ethoxy]cyclobutanecarboxylate;
3-[2-[4-[8-chloro-6-fluoro-4-oxo-3-(trifluoromethoxy)chromen-2-yl]phenoxy]ethoxy]cyclobutanecarboxylic acid;
3-[2-[4-(3-bromo-8-chloro-4-oxo-chromen-2-yl)phenoxy]ethoxy]cyclobutanecarboxylic acid;
3-[2-[4-(3-benzyloxy-8-chloro-4-oxo-chromen-2-yl)phenoxy]ethoxy]cyclobutanecarboxylic acid;
3-[2-[4-[8-chloro-4-oxo-6-(trifluoromethyl)chromen-2-yl]phenoxy]ethoxy]-cyclobutanecarboxylic acid;
3-[2-[4-(8-chloro-6-cyclopropyl-4-oxo-chromen-2-yl)phenoxy]ethoxy]cyclobutanecarboxylic acid;
3-[2-[4-[8-chloro-4-oxo-6-(2-oxopyrrolidin-1-yl)chromen-2-yl]phenoxy]ethoxy]-cyclobutanecarboxylic acid;
3-[2-[4-[8-chloro-4-oxo-7-(trifluoromethyl)chromen-2-yl]phenoxy]ethoxy]-cyclobutanecarboxylic acid;
3-[2-[4-(8-chloro-7-cyclopropyl-4-oxo-chromen-2-yl)phenoxy]ethoxy]cyclobutanecarboxylic acid;
ethyl 2-[2-[4-(7-bromo-8-chloro-4-oxo-chromen-2-yl)phenoxy]ethoxy]acetate;
3-[2-[4-[8-chloro-4-oxo-7-(trifluoromethyl)chromen-2-yl]-2-methyl-phenoxy]-ethoxy]cyclobutanecarboxylic acid; and
Cis-3-[2-[2-chloro-4-[8-chloro-4-oxo-7-(trifluoromethyl)chromen-2-yl]phenoxy]-ethoxy]cyclobutanecarboxylic acid;
or a pharmaceutically acceptable salt, or enantiomer, or diastereomer thereof.

16. A compound according to claim 13, selected from:
3-[2-[4-(8-chloro-4-oxo-chromen-2-yl)phenoxy]ethoxy]cyclobutanecarboxylic acid;
cis-3-[2-[4-(8-chloro-4-oxo-chromen-2-yl)phenoxy]ethoxy]cyclobutanecarboxylic acid;
trans-3-[2-[4-(8-chloro-4-oxo-chromen-2-yl)phenoxy]ethoxy]cyclobutanecarboxylic acid;
3-[2-[4-(8-chloro-4-oxo-chromen-2-yl)phenoxy]-1-methyl-ethoxy]cyclobutanecarboxylic acid;
3-[2-[4-(8-chloro-6-fluoro-4-oxo-chromen-2-yl)phenoxy]ethoxy]cyclobutanecarboxylic acid;
cis-3-[2-[4-(8-chloro-5-methoxy-4-oxo-chromen-2-yl)phenoxy]ethoxy]cyclobutanecarboxylic acid;
cis-3-[2-[4-(5,8-dichloro-4-oxo-chromen-2-yl)phenoxy]ethoxy]cyclobutanecarboxylic acid;
cis-3-[2-[4-(8-bromo-4-oxo-chromen-2-yl)phenoxy]ethoxy]cyclobutanecarboxylic acid;
cis-3-[2-[4-(8-chloro-4-oxo-chromen-2-yl)-2-fluoro-phenoxy]ethoxy]cyclobutanecarboxylic acid;
cis-3-[2-[2-chloro-4-(8-chloro-4-oxo-chromen-2-yl)phenoxy]ethoxy]cyclobutanecarboxylic acid;
cis-3-[2-[2-bromo-4-(8-chloro-4-oxo-chromen-2-yl)phenoxy]ethoxy]cyclobutanecarboxylic acid;

3-[2-[4-(8-chloro-4-oxo-chromen-2-yl)-2-methyl-phenoxy]ethoxy]cyclobutanecarboxylic acid;

3-[2-[4-(8-chloro-4-oxo-chromen-2-yl)-3-ethoxy-phenoxy]ethoxy]cyclobutanecarboxylic acid;

3-[2-[4-(8-chloro-4-oxo-thiochromen-2-yl)phenoxy]ethoxy]cyclobutanecarboxylic acid;

2-[2-[4-(8-chloro-4-oxo-thiochromen-2-yl)phenoxy]ethoxy]acetic acid; and

2-[2-[4-(8-chloro-4-oxo-chromen-2-yl)phenoxy]ethoxy]acetamide;

or a pharmaceutically acceptable salt, or enantiomer, or diastereomer thereof.

17. A pharmaceutical composition comprising a compound in accordance with claim 1 and a therapeutically inert carrier.

18. A method for the treatment of HBV infection, which method comprises:

administering an effective amount of a compound as defined in claim 15 to a patient in need thereof.

19. A pharmaceutical composition comprising a compound in accordance with claim 15 and a therapeutically inert carrier.

\* \* \* \* \*

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aagaaaaacc ccgcctgtaa                                             20

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctgttctga ctactgcctc tcc                                         23

<210> SEQ ID NO 3
<211> LENGTH: 27
<212> TYPE: DNA
<213> ORGANISM: Artificial Sequence

```
<220> FEATURE:
<223> OTHER INFORMATION: Description of Artificial Sequence: Synthetic
      probe

<400> SEQUENCE: 3
cctgatgtga tgttctccat gttcagc                                     27
```